(12) United States Patent
Larson et al.

(10) Patent No.: US 8,886,287 B2
(45) Date of Patent: Nov. 11, 2014

(54) TISSUE-STABILIZATION DEVICE AND METHOD FOR MEDICAL PROCEDURES

(75) Inventors: Blake Timothy Larson, Saint Paul, MN (US); Arthur Guy Erdman, New Brighton, MN (US)

(73) Assignee: MRI Robotics LLC, Saint Paul, MN (US)

(*) Notice: Subject to any disclaimer, the term of this patent is extended or adjusted under 35 U.S.C. 154(b) by 1565 days.

(21) Appl. No.: 12/423,798

(22) Filed: Apr. 14, 2009

(65) Prior Publication Data

US 2010/0069740 A1 Mar. 18, 2010

Related U.S. Application Data

(60) Provisional application No. 61/124,057, filed on Apr. 14, 2008, provisional application No. 61/124,058, filed on Apr. 14, 2008, provisional application No. 61/168,559, filed on Apr. 11, 2009.

(51) Int. Cl.
| | |
|---|---|
| *A61B 5/05* | (2006.01) |
| *A61B 5/055* | (2006.01) |
| *A61B 19/00* | (2006.01) |
| *A61B 17/34* | (2006.01) |
| *A61B 8/00* | (2006.01) |
| *A61B 10/02* | (2006.01) |
| *A61B 6/04* | (2006.01) |
| *B29C 65/78* | (2006.01) |
| *B23Q 39/00* | (2006.01) |

(52) U.S. Cl.
CPC ....... *A61B 5/0555* (2013.01); *A61B 2017/3409* (2013.01); *A61B 8/406* (2013.01); *A61B 10/0233* (2013.01); *A61B 6/0435* (2013.01); *B29C 65/7802* (2013.01); *B23Q 39/00* (2013.01); *A61B 19/201* (2013.01); *B65D 2519/00059* (2013.01); *A61B 2019/205* (2013.01)
USPC .............. 600/415; 600/407; 600/421; 29/469

(58) Field of Classification Search
None
See application file for complete search history.

(56) References Cited

U.S. PATENT DOCUMENTS

| | | | |
|---|---|---|---|
| 23,503 | A | 4/1859 | Selden |
| 244,215 | A | 7/1881 | Fenby |

(Continued)

OTHER PUBLICATIONS

Bosscher, Paul, et al., "A Novel Mechanism for Implementing Multiple Collocated Spherical Joints", "Proceedings of the 2003 IEEE International Conference on Robotics & Automation", Sep. 14-19, 200, pp. 336-341.

(Continued)

*Primary Examiner* — Jonathan Cwern
*Assistant Examiner* — Shahdeep Mohammed
(74) *Attorney, Agent, or Firm* — Charles A. Lemaire; Jonathan M. Rixen; Lemaire Patent Law Firm, P.L.L.C.

(57) ABSTRACT

A method and apparatus for designing and fabricating a pantomesh. The pantomesh includes a plurality of pantomesh elements each including a pairs of links connected to one another by a revolute joint at points between their ends. Each of a plurality of the pantomesh elements is connected using spherical joints to a plurality of neighboring pantomesh elements, wherein a first line that extends along one side of a first pantomesh element forms a first variable angle with a second line that extends along an opposite side of the first pantomesh element. In some embodiments, at least some of the pantomesh elements of the pantomesh are not isosceles trapezoidal elements. In some embodiments, the pantomesh is used to compress breast tissue during an MRI procedure. In some embodiments, the pantomesh is connected to one or more actuators that facilitate remote control of the amount of compression provided.

20 Claims, 32 Drawing Sheets

(56) References Cited

U.S. PATENT DOCUMENTS

| | | |
|---|---|---|
| 764,224 A | 7/1904 | Brown |
| 3,124,387 A | 3/1964 | Maclaren |
| 3,672,104 A | 6/1972 | Luckey |
| 4,193,415 A | 3/1980 | Hermanson |
| 4,942,700 A | 7/1990 | Hoberman |
| 5,024,031 A | 6/1991 | Hoberman |
| 5,657,584 A | 8/1997 | Hamlin |
| 5,761,871 A | 6/1998 | Atake |
| 2007/0250047 A1* | 10/2007 | Harter ............................. 606/1 |

OTHER PUBLICATIONS

Buhl, Thomas, et al., "Shape optimization of cover plates for retractable roof structures", "Computers and Structures", 2004, pp. 1227-1236, vol. 82.

Dai, Jian S., et al., "Mobility analysis of a complex structured ball based on mechanism decomposition and equivalent screw system analysis", "Mechanism and Machine Theory", 2004, pp. 445-458, vol. 39.

Escrig, F., "Expandable space structures", "Space Structures", 1985, pp. 79-91, vol. 1.

Gantes, Charis J., et al., "Structural Analysis and Design of Deployable Structures", 1989, pp. 661-669, vol. 32, No. 3/4.

Jensen, F., et al., "Expandable Structures formed by Hinged Plates", "Fifth International Conference on Space Structures", Aug. 19-21, 2002.

Jensen, F., et al., "Expandable 'Blob' Structures", "Journal of the International Association for Shell and Spatial Structures: IASS", 2004, pp. 151-158, vol. 46, No. 3.

Kaveh, A., et al., "Analysis of pantograph foldable structures", "Computers & Structures", 1996, pp. 131-140, vol. 59, No. 1.

Kaveh, A., et al., "Optimal design of pantograph foldable structures", "International Journal of Space Structures", 1999, pp. 295-302, vol. 14, No. 4.

You, Zhong, "Motion structures extend their reach", "Materials Today", Dec. 2007, p. 52 vol. 10, No. 12.

* cited by examiner

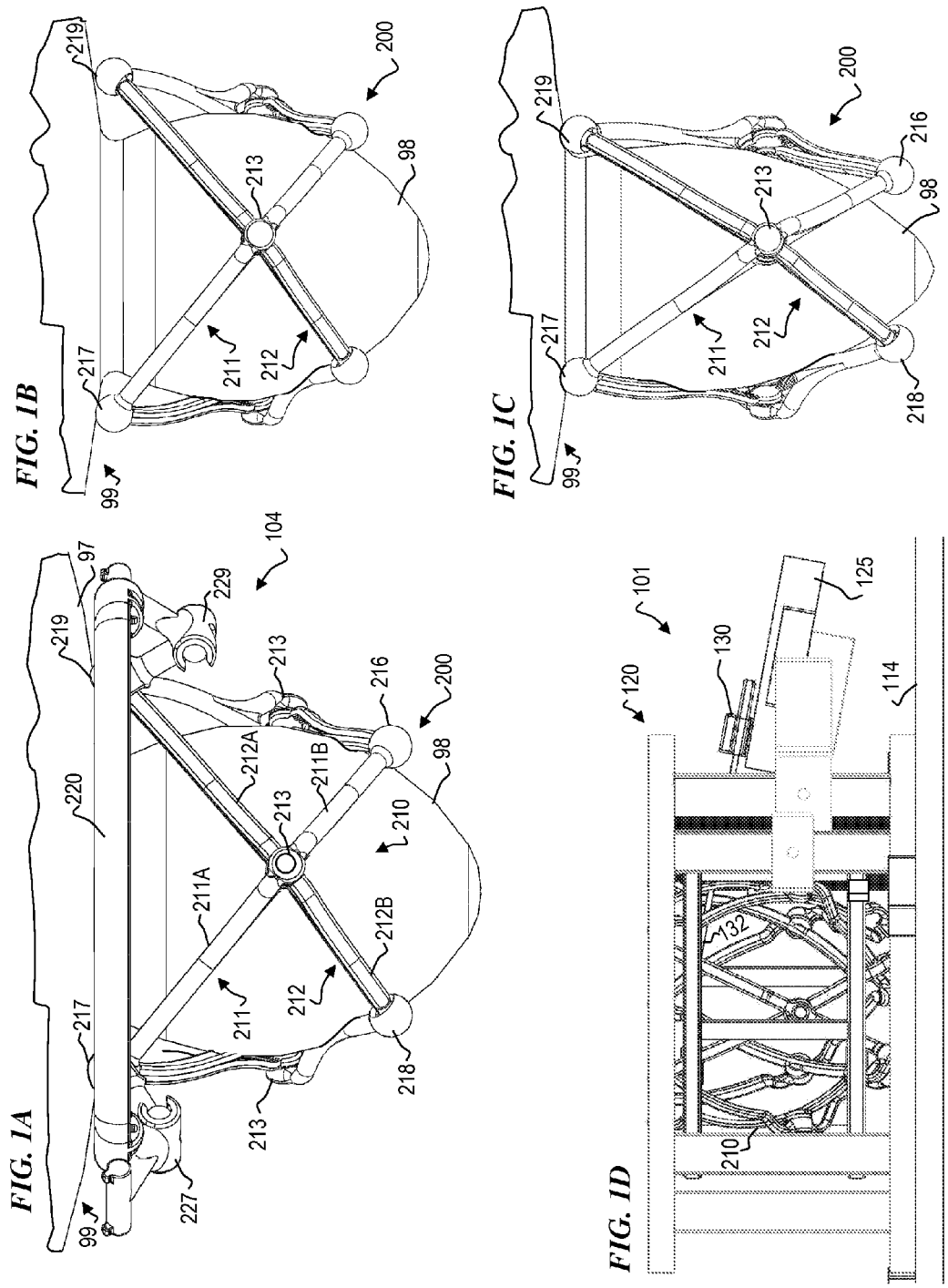

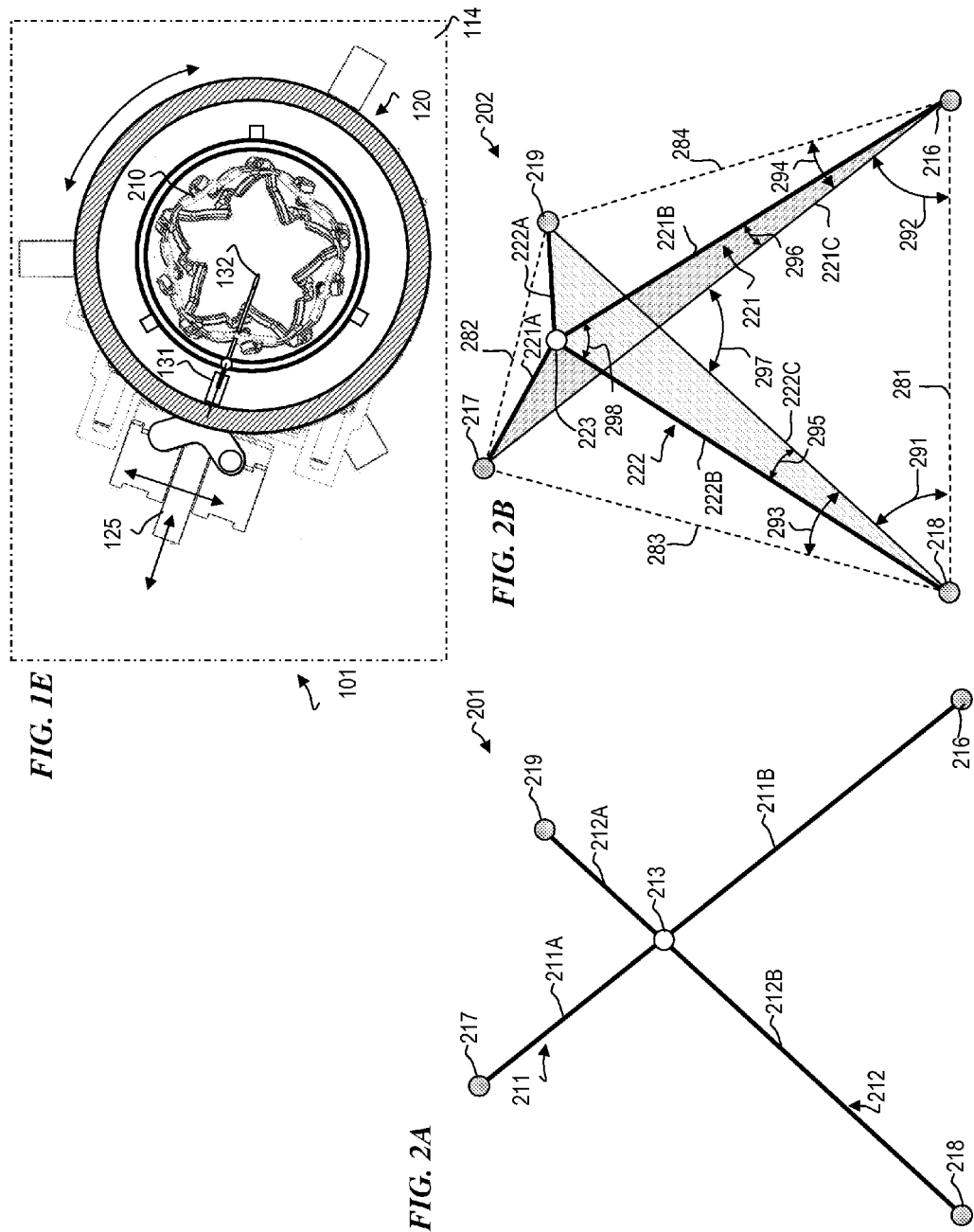

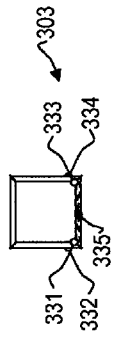
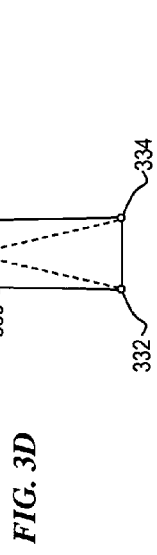
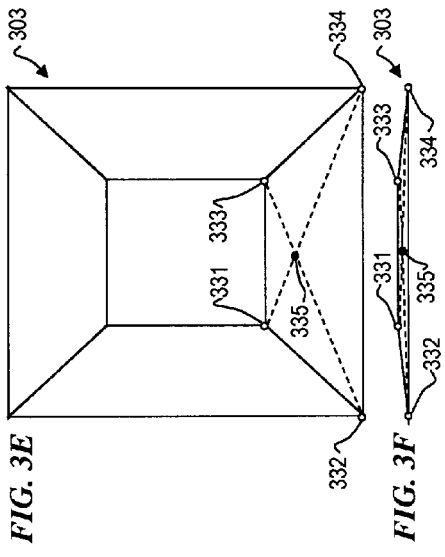
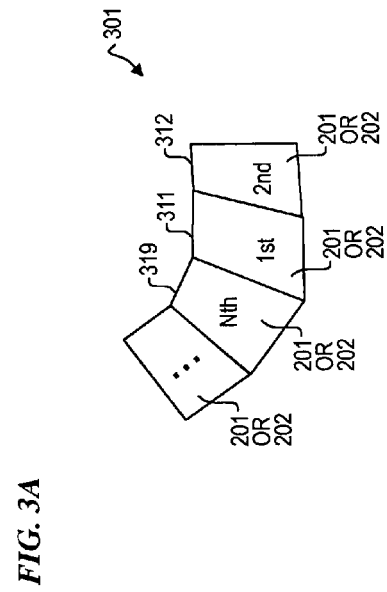
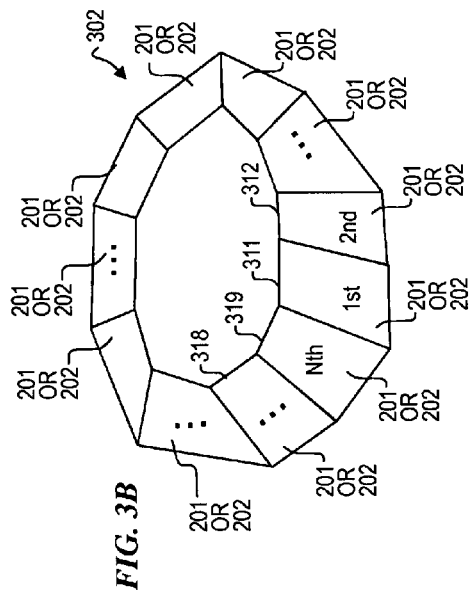
*FIG. 3A*
*FIG. 3B*
*FIG. 3C*
*FIG. 3D*
*FIG. 3E*
*FIG. 3F*

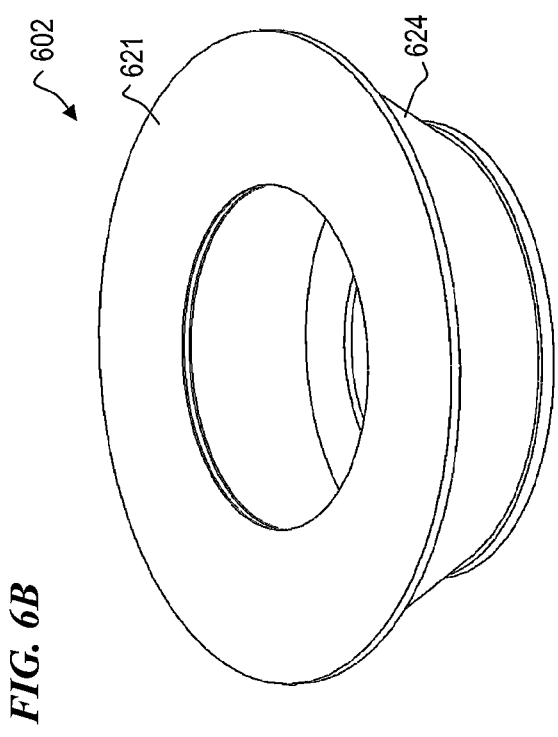
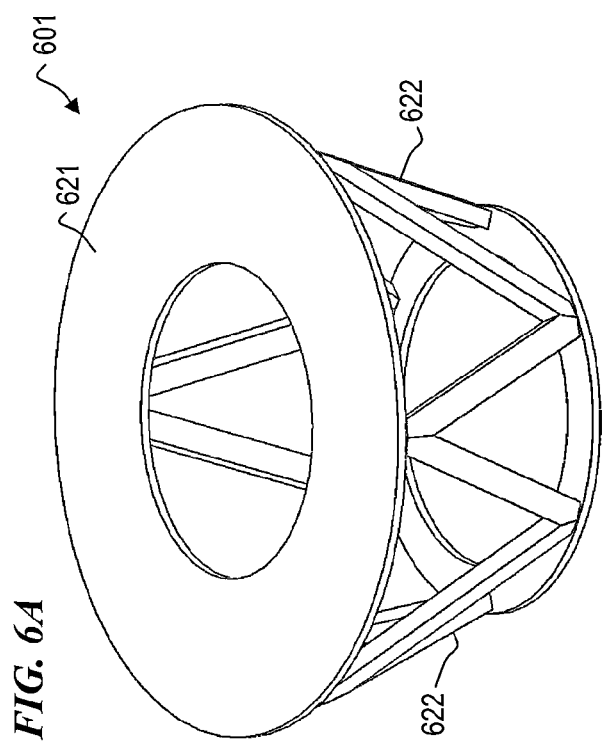

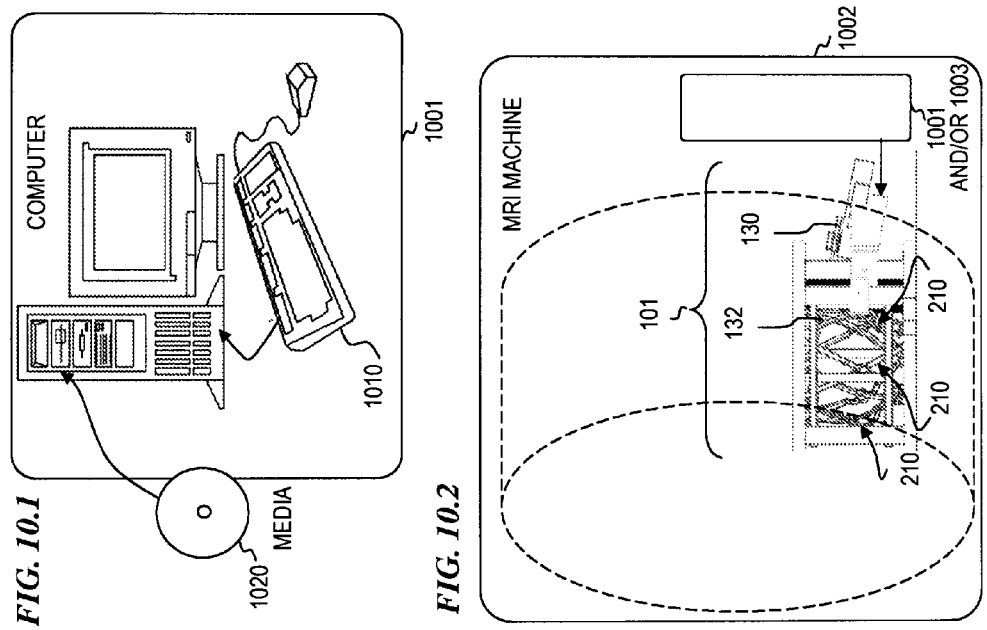
FIG. 9
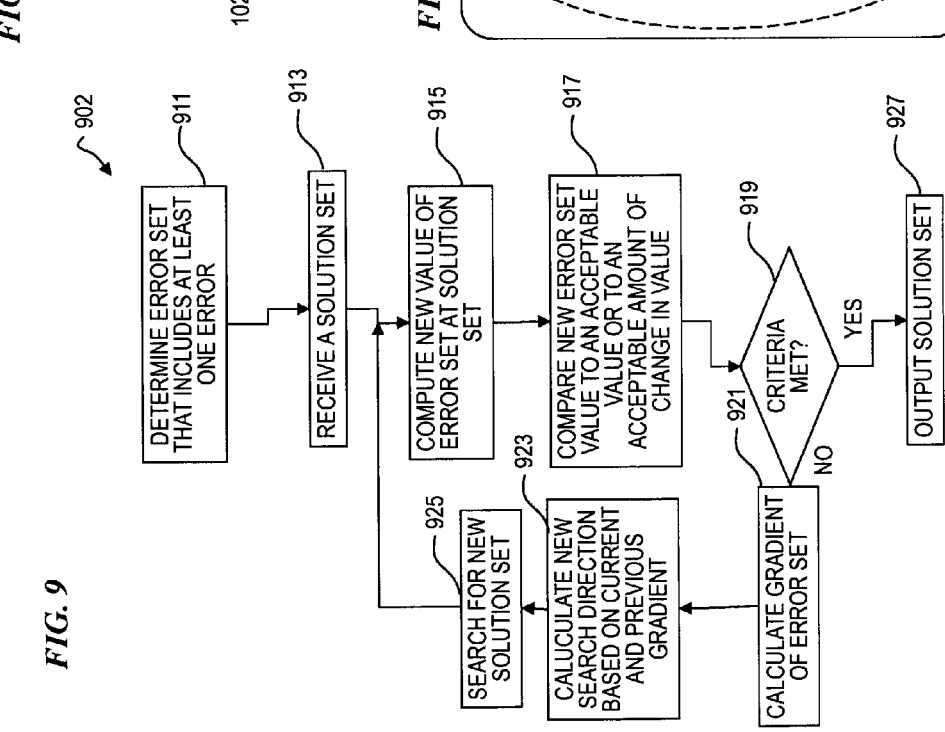
FIG. 10.1
FIG. 10.2

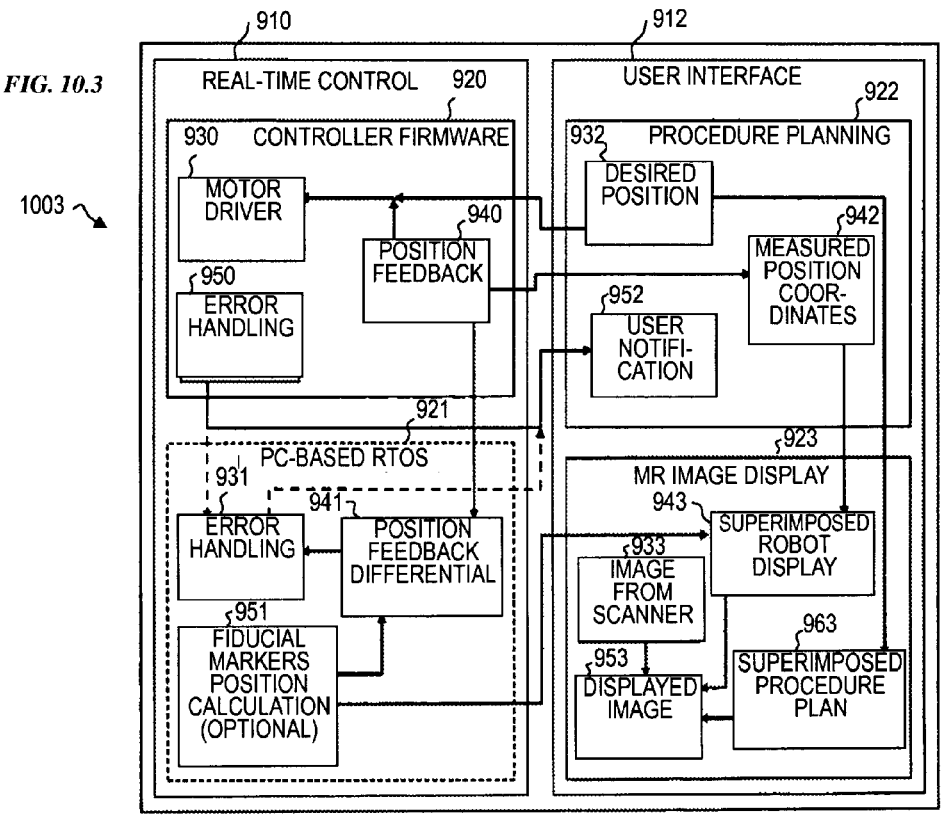
FIG. 10.3
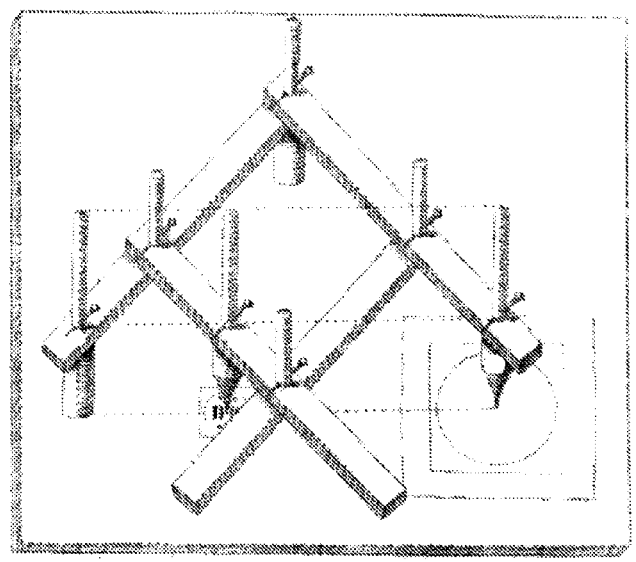
FIG. 11.1
PRIOR ART

FIG. 11.2 PRIOR ART
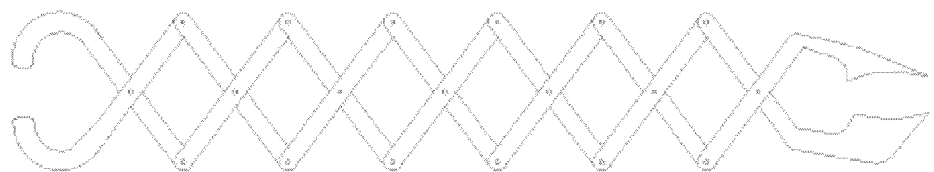
FIG. 11.3 PRIOR ART
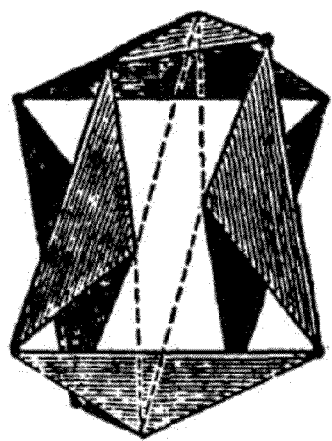

*FIG. 11.4 PRIOR ART*
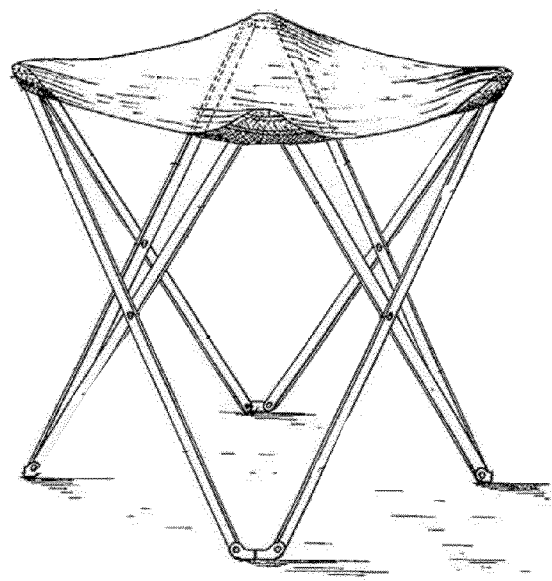
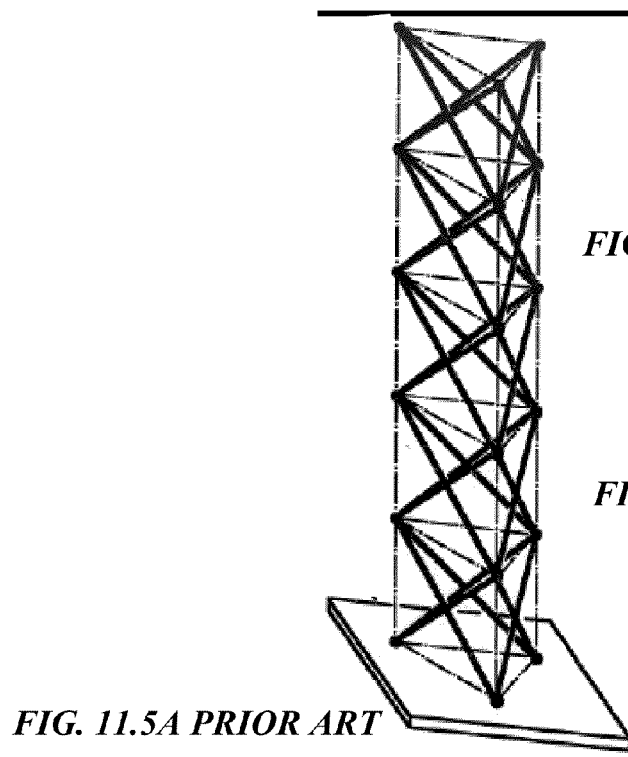
*FIG. 11.5B PRIOR ART*
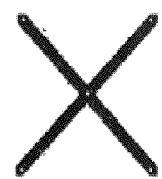
*FIG. 11.5C PRIOR ART*
*FIG. 11.5A PRIOR ART*
*FIG. 11.5D PRIOR ART*

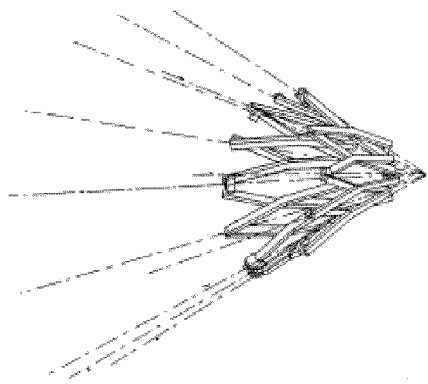
FIG. 11.7B PRIOR ART
FIG. 11.6B PRIOR ART
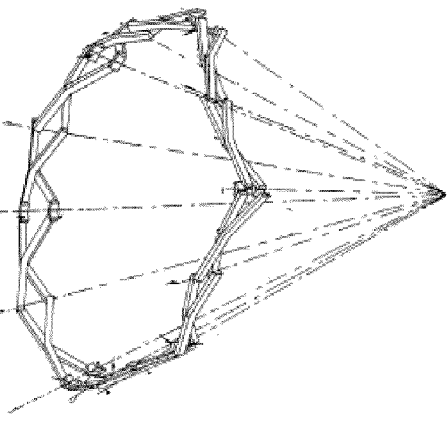
FIG. 11.7A PRIOR ART
FIG. 11.6A PRIOR ART FIG. 11.8A PRIOR ART
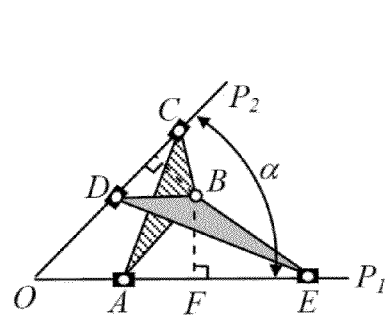
FIG. 11.8B PRIOR ART
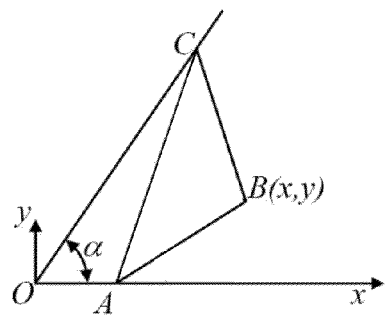
FIG. 11.9A PRIOR ART
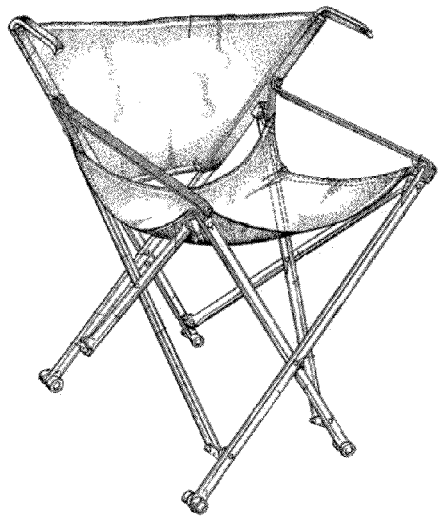
FIG. 11.9B PRIOR ART
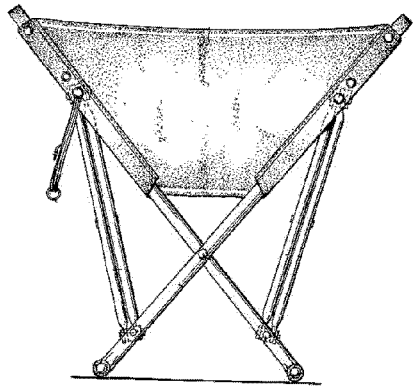

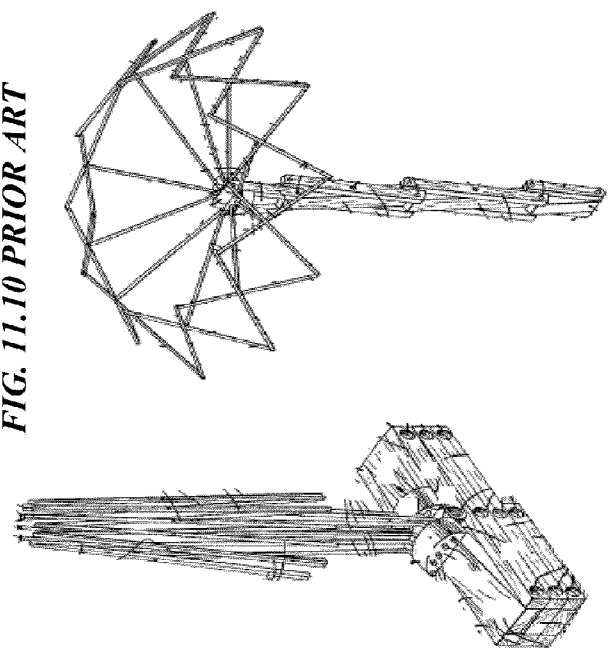
*FIG. 11.10 PRIOR ART*
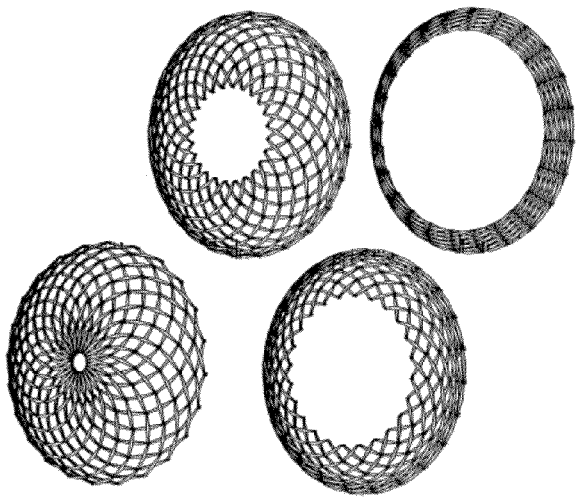
*FIG. 11.11 PRIOR ART*

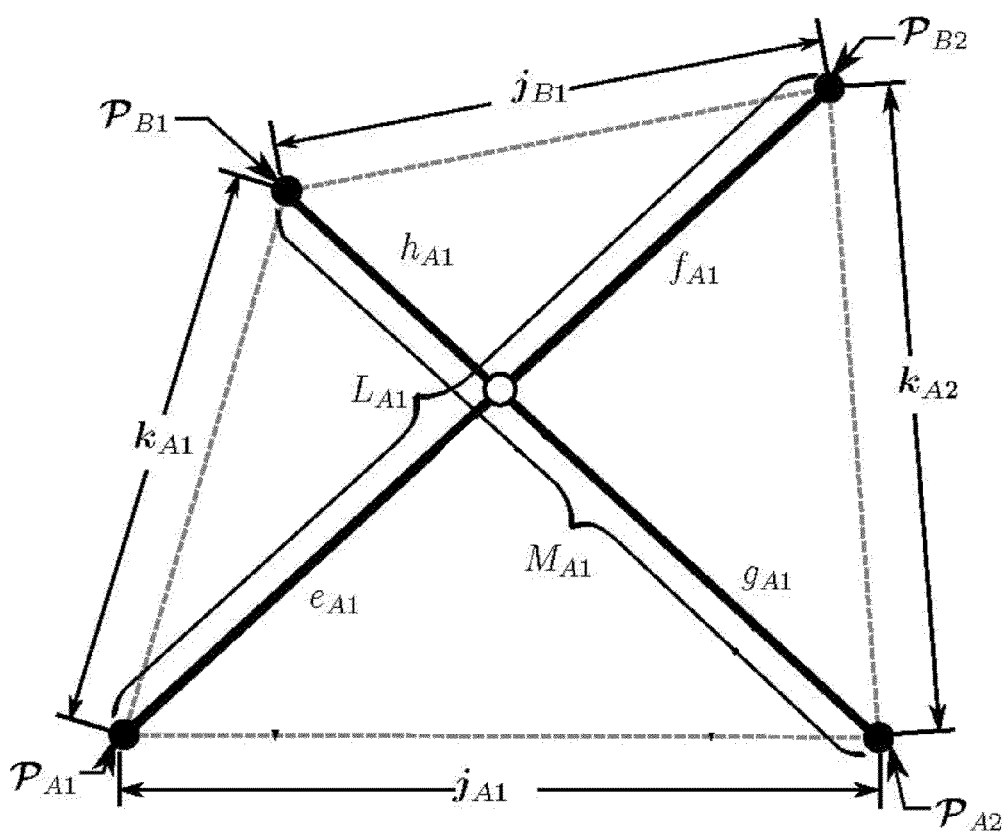
*FIG. 12.1*

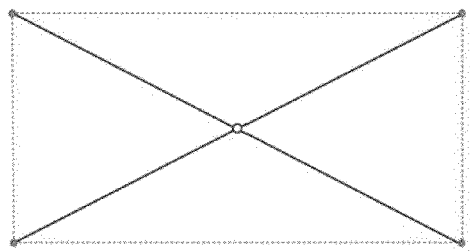
FIG. 12.2A
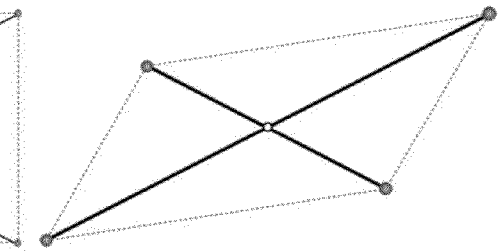
FIG. 12.2B
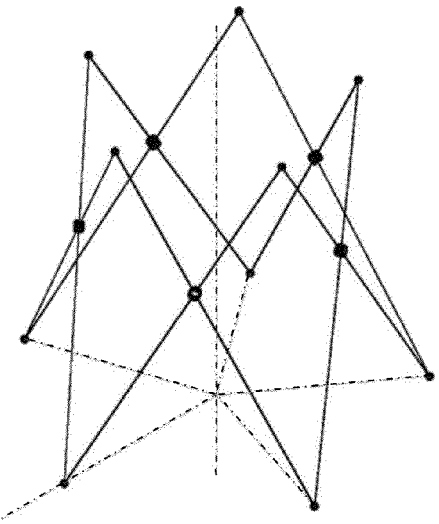
FIG. 12.3A
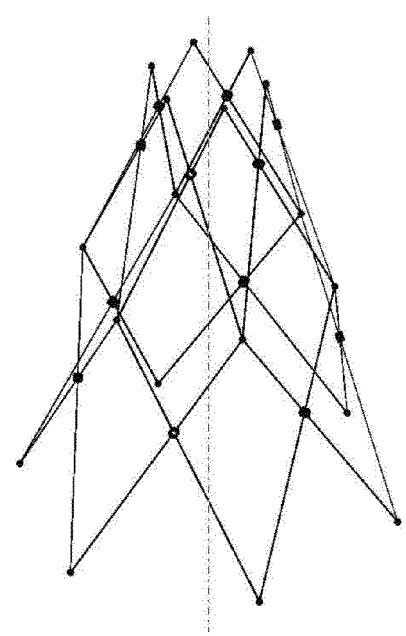
FIG. 12.3B

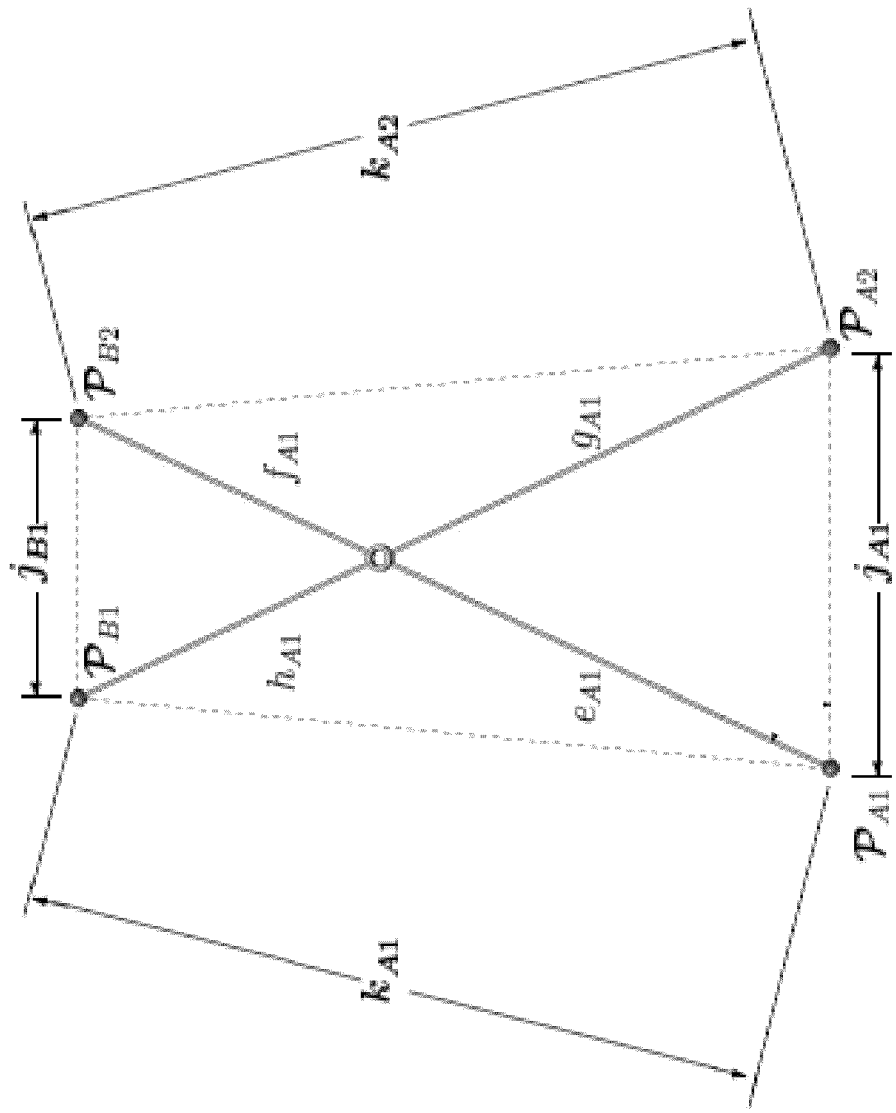
FIG. 12.4

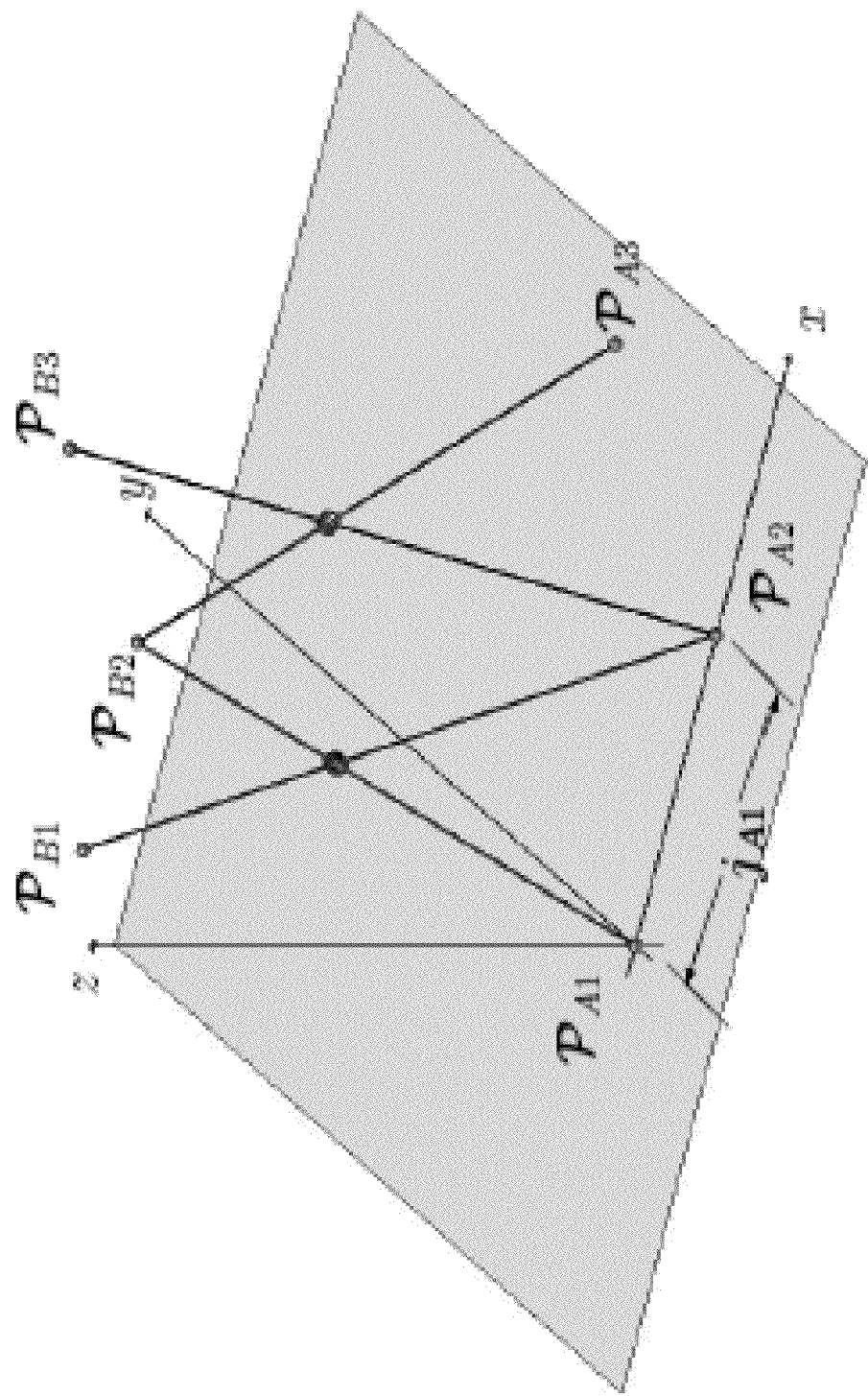
FIG. 12.5

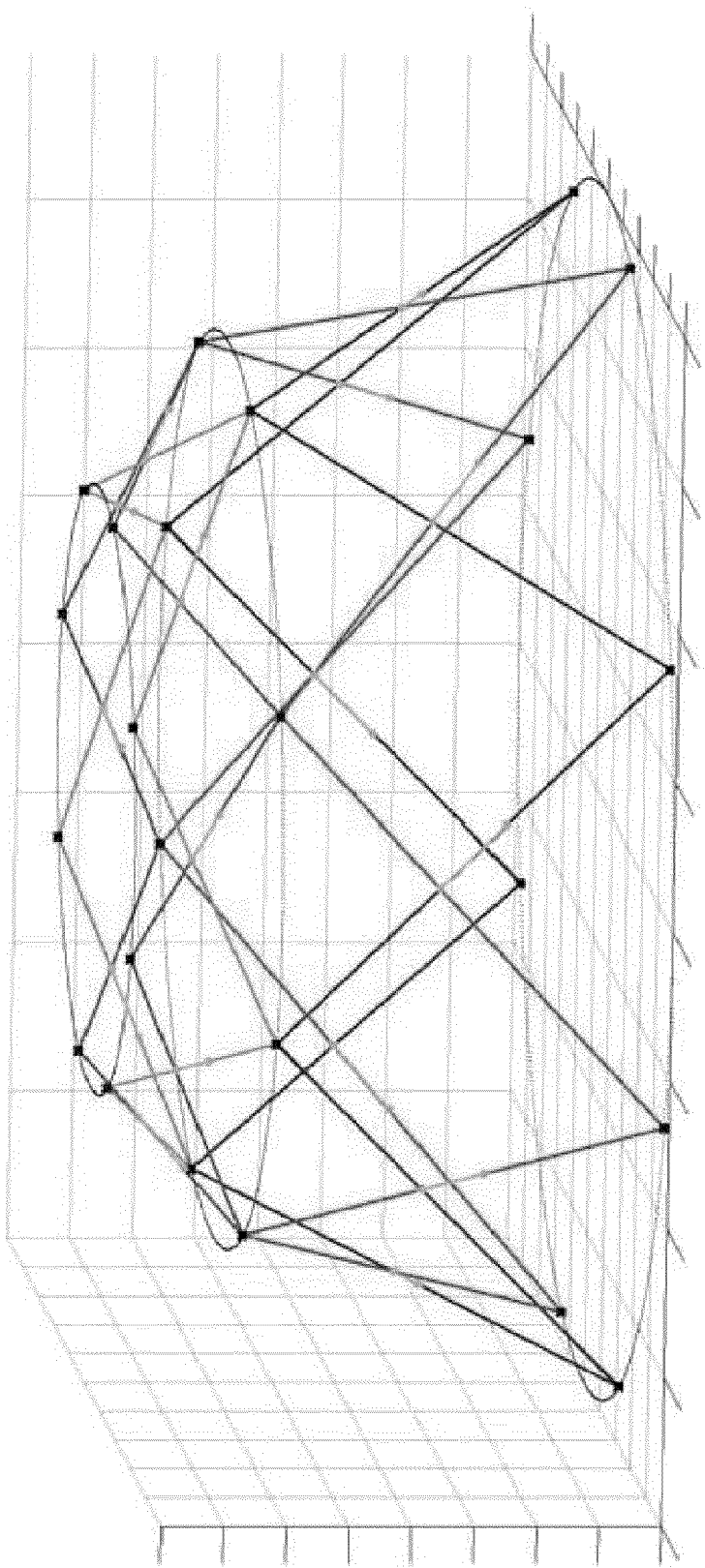
FIG. 13.1

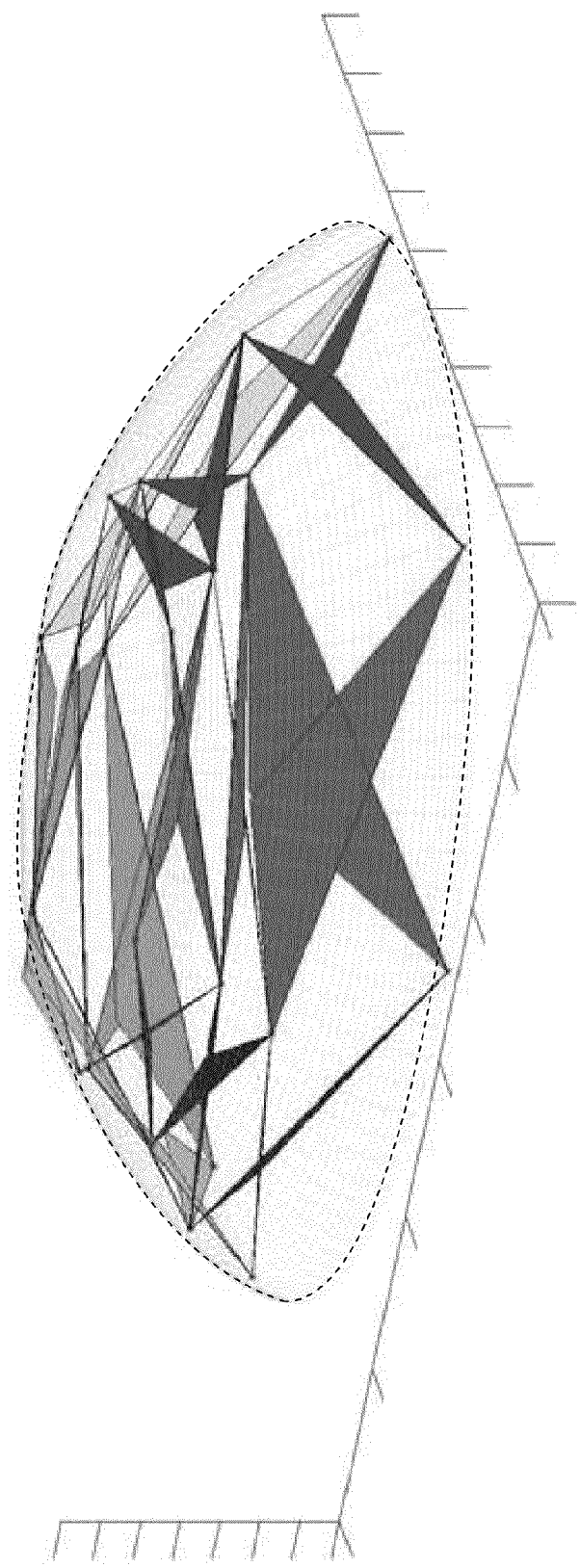
FIG. 13.2A

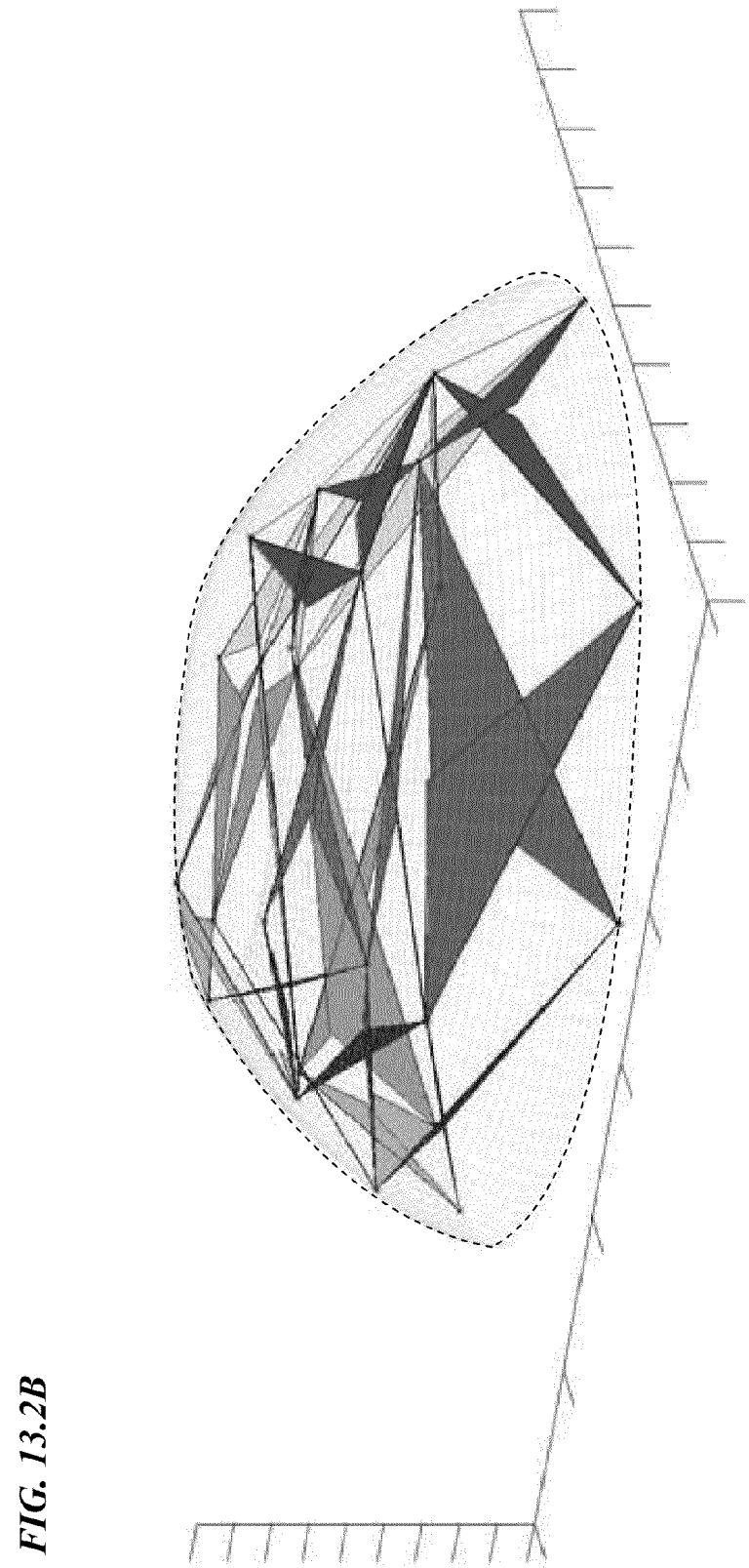
FIG. 13.2B

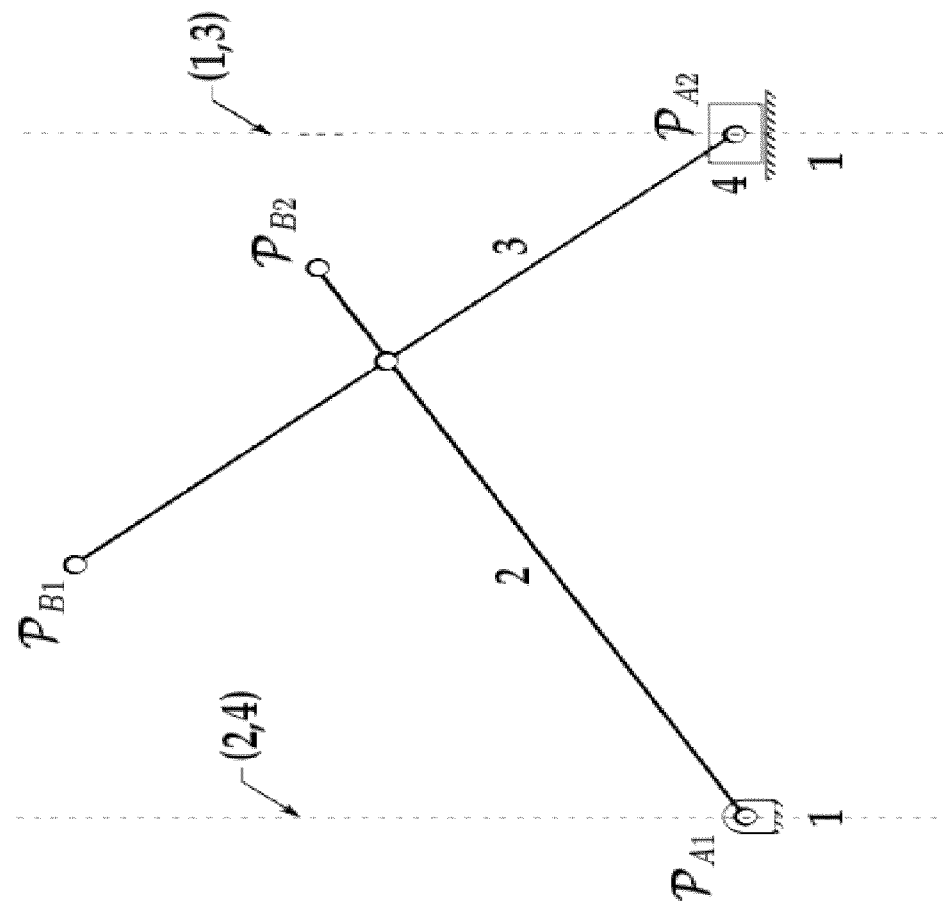
FIG. 13.3

*FIG. 13.4*
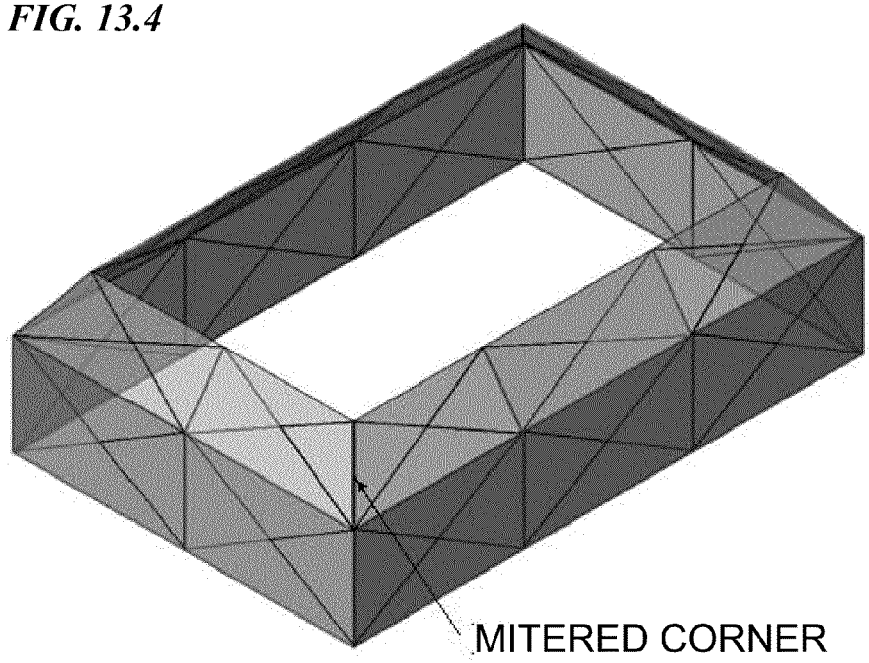

FIG. 13.5A
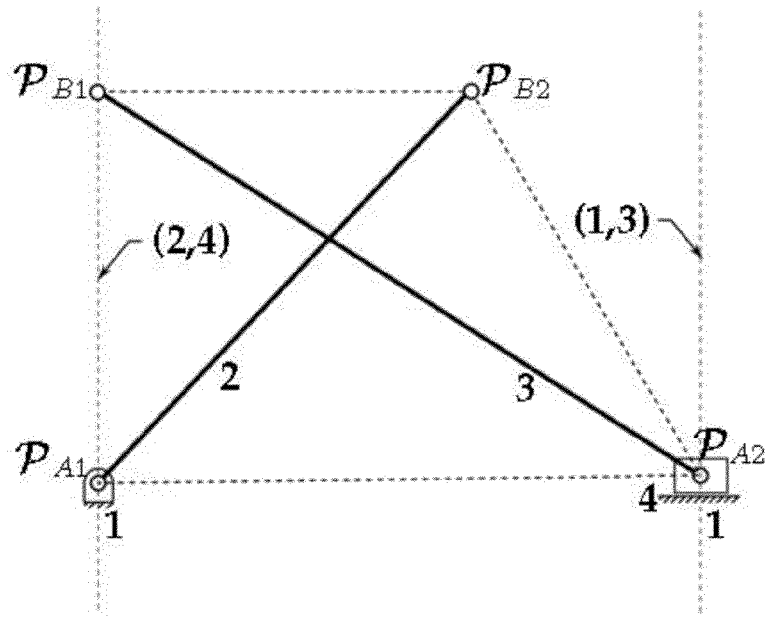
FIG. 13.5B
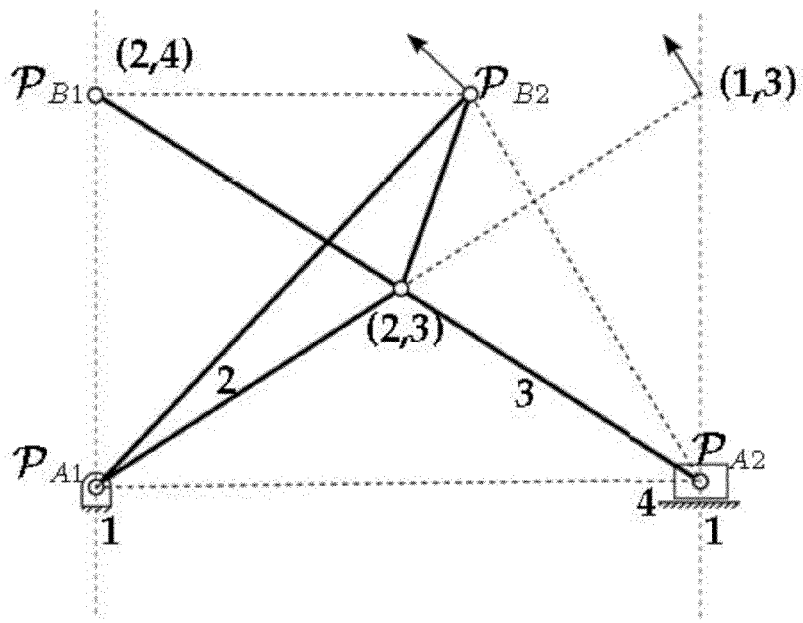

FIG. 13.6A
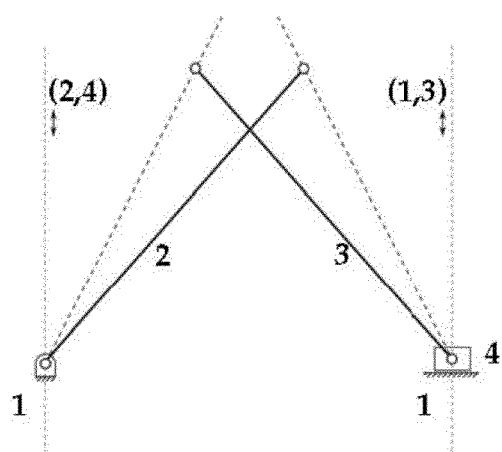
FIG. 13.6B
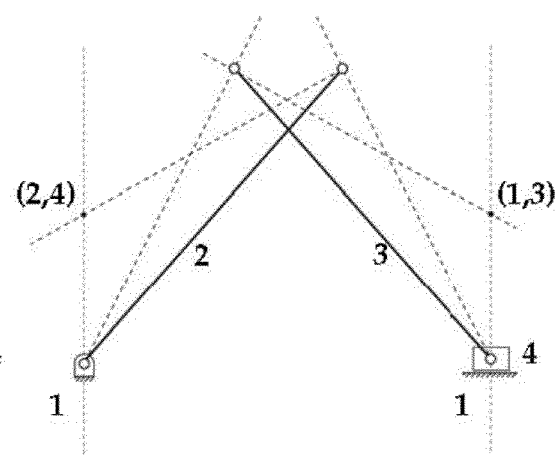
FIG. 13.6C
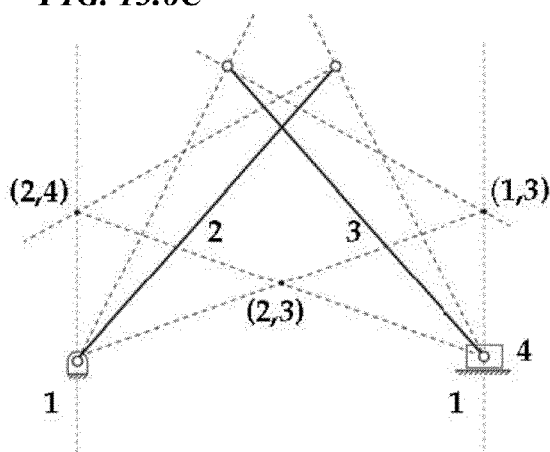
FIG. 13.6D
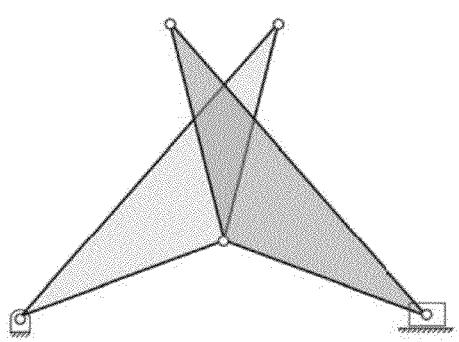

*FIG. 13.7*
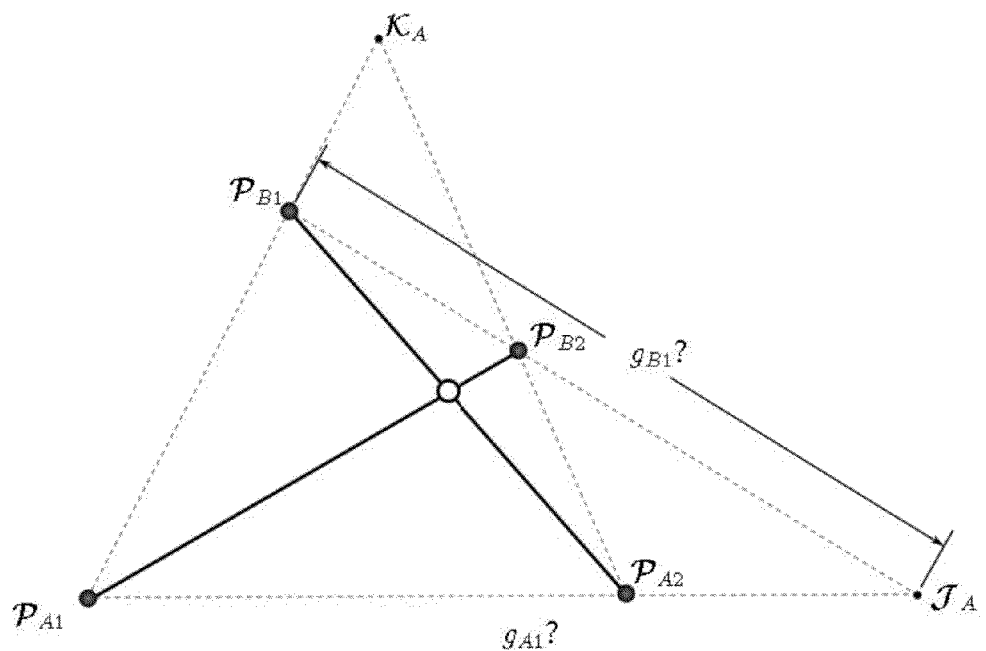

TISSUE-STABILIZATION DEVICE AND METHOD FOR MEDICAL PROCEDURES

CROSS-REFERENCE TO RELATED APPLICATIONS

This invention claims benefit of U.S. Provisional Patent Application 61/124,057 titled "Breast Stabilization Device" and filed Apr. 14, 2008, and of U.S. Provisional Patent Application No. 61/168,559, filed Apr. 11, 2009, which are each hereby incorporated herein in their entirety by reference.

This invention is related to and claims benefit of U.S. Provisional Patent Application 61/124,058 titled "Device for MRI-guided Breast Intervention" and filed Apr. 14, 2008, which is hereby incorporated by reference in its entirety.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of grant number DAMD1703-10397 awarded under the U.S. Army Breast Cancer Research Program.

FIELD OF THE INVENTION

This invention relates to the field of mechanical positioners, and more specifically to a method and apparatus for holding, immobilizing and positioning biological tissue (such as a human breast) to stabilize the tissue during a medical procedure (such as a magnetic-resonance imaging (MRI)-guided biopsy and related interventions).

BACKGROUND OF THE INVENTION

The pantograph has a long history in kinematics; it is one of the oldest multi-link examples of displacement magnification. Early uses were for transcription, then for collapsible structures, and even for children's toys. Many pantograph-style linkages have been developed using multiple pantograph-like units that obey certain geometric restrictions, but have yet to be described in a general fashion.

U.S. Pat. No. 244,215 titled "Camp stool" by inventor Joseph Beverley Fenby issued Jul. 12, 1881, and is incorporated herein by reference. This patent describes rectangular pantograph elements used to construct a camp stool.

U.S. Pat. No. 764,224 titled "Trolley" by inventor John Quincy Brown issued Jul. 5, 1904, and is incorporated herein by reference. The patent describes a pantograph used for electrical power transmission from overhead lines for electric trains.

U.S. Pat. No. 3,672,104 titled "Nesting Three Dimensional Lazy Tong Structure" by inventor George R. Luckey issued Jun. 27, 1972, and is incorporated herein by reference. The patent describes a nesting three-dimensional lazy tong structure of hollow polygonal cross-section having tapered sides provided by lazy tong frames whose hinged links are pivotally joined and cross-over one another in a manner such that the successive link sets or tiers of the structure nest one within the other when the structure is retracted to its contracted configuration to provide the structure with a contracted length approximating the contracted dimension of a single link set or tier. A lazy tong frame and link pair for the structure.

U.S. Pat. No. 4,942,700 titled "Reversibly expandable doubly-curved truss structure" by inventor Charles Hoberman issued Jul. 24, 1990, and is incorporated herein by reference. This patent describes a loop-assembly is disclosed which is comprised of at least three scissors-pairs, at least two of the pairs comprising: two essentially identical rigid angulated strut elements each having a central and two terminal pivot points with centers which do not lie in a straight line, each strut being pivotally joined to the other of its pair by their central pivot points, each pair being pivotally joined by two terminal pivot points to two terminal pivot points of another pair in that, (a) the terminal pivot points of each of the scissors-pairs are pivotally joined to the terminal pivot points of the adjacent pair such that both scissors-pairs lie essentially in the same plane, or (b) the terminal pivot points of a scissors-pair are each pivotally joined to a hub element which is small in diameter relative to the length of a strut element, and these hub elements are in turn joined to the terminal pivot points of another scissors-pair, such that the plane that one scissors-pair lies in forms an angle with the plane that the other scissors-pair lies in, the axes passing through the pivot points of one of the scissors-pair not being parallel to the axes of the other scissors-pair, where a closed loop-assembly is thus formed of scissors-pairs, and this loop-assembly can freely fold and unfold without bending or distortion of any of its elements, and a line that intersects and is perpendicular to the axes of any two terminal pivot points is non-parallel with at least two other similarly formed lines in the assembly, the angles formed between said lines remaining constant as the loop-assembly is folded and unfolded.

U.S. Pat. No. 3,124,387 titled "Seating structures" by inventor Owen Finlay Maclaren issued Mar. 10, 1964, and is incorporated herein by reference. This patent describes the use of pantograph elements with offset pin joints to construct a folding seating structure.

U.S. Pat. No. 4,193,415 titled "Umbrella canopy frame and staff construction" by inventor Terry Hermanson issued Mar. 18, 1980, and is incorporated herein by reference. This patent describes umbrella construction comprising first and second hub members in combination with a canopy frame member and a staff member, the hub members being spaced-apart from each other on opposite sides of the staff member, independent of each other, and provided with a plurality of holes, the staff member including two series of links forming a lazy-tong device adapted to fold together into closed condition and to unfold into opened condition, the two series of links each having an upper link unit pivotally connected to the upper link unit of the other at the upper ends thereof when the staff means is in opened condition, one of the hub members being secured to the upper link unit of one of the series of links adjacent the upper end thereof, the other of the hub members being secured to the upper link unit of the other of the series of links adjacent the upper end thereof and on a side of the staff member opposite from the one of the hub members. The canopy frame member includes a circumferentially extending series of pairs of ribs, each rib of the pairs being pivotally connected to the other at a point intermediate the opposite ends thereof. A plurality of spokes each have a radially inner end extending in a separate one of the holes of the hub members and a radially outer end pivotally secured to a separate pair of the ribs at the intermediate point thereof.

U.S. Pat. No. 23,503 titled "Umbrella" by inventor L. K. Selden issued Apr. 5, 1859, and is incorporated herein by reference. This patent describes a folding umbrella frame.

U.S. Pat. No. 5,761,871 titled "Framework structure" by inventor Katsuhito Atake issued Jun. 9, 1998, and is incorporated herein by reference. This patent describes a framework structure comprises three or more primary constituent units each including two rigid diagonal members constituting the diagonals of a quadrangular lateral face of a solid and coupled together for relative rotation about a first rotation axis passing through the intersection of the diagonals. The primary constituent units are coupled to one another via second and third rotation axes into a ring-like form. A more complicated framework structure can be obtained by using a plurality of these framework structures as secondary constituent units which are coupled to one another with a coupler or a primary constituent unit used in common between adjacent ones of the secondary constituent units. The framework structure can provide one which is capable of being expanded and contracted in three-dimensional directions and which has rigidity in any directions.

U.S. Pat. No. 5,024,031 titled "Radial expansion/retraction truss structures" by inventor Charles Hoberman issued Jun. 18, 1991, and is incorporated herein by reference. This patent describes a loop-assembly is disclosed which is comprised of at least three scissors-pairs, at least two of the pairs comprising: two essentially identical rigid angulated strut elements, each having a central and two terminal pivot points which do not lie in a straight line, each strut being pivotally joined to the other of its pair by their central pivot points, each pair being pivotally joined by two terminal pivot points to two terminal pivot points of another pair such that both scissors pairs lie essentially in the same plane, or each pair being pivotally joined by two terminal pivot points to two terminal pivot points of another pair in that the terminal points of a scissors-pair are each pivotally joined to a hub element, and these hub elements are in turn joined to the terminal pivot points of another scissors-pair, whereby a closed loop-assembly is thus formed of scissors pairs, and this loop-assembly can fold and unfold, and a line that intersects and is perpendicular to the axes of any two terminal pivot points is non-parallel with at least two other similarly formed lines in the assembly, the angles formed between said lines remaining constant as the loop assembly is folded and unfolded.

U.S. Pat. No. 5,657,584 titled "Concentric joint mechanism" by inventor Gregory J. Hamlin issued Aug. 19, 1997, and is incorporated herein by reference. This patent describes a joint mechanism having a movement between relative members about a center of rotation located at a point where a first line extends from one of the members intersects a second line extending from the opposite member is disclosed. Multiple joint mechanisms may be aligned together along with common lines being the axis of rotation of each joint mechanism to provide a concentric spherical joint mechanism. Concentric spherical joint mechanism may be used to assemble truss frame structures.

SUMMARY OF THE INVENTION

In some embodiments, the present invention provides a method and apparatus for designing and fabricating a pantomesh, and/or provides the resulting pantomesh. The pantomesh includes a plurality of pantomesh elements each including a pairs of links connected to one another by a revolute joint at points between their ends. Each of a plurality of the pantomesh elements is connected using spherical joints to a plurality of neighboring pantomesh elements, wherein a first line that extends along one side of a first pantomesh element forms a first variable angle with a second line that extends along an opposite side of the first pantomesh element. In some embodiments, at least some of the pantomesh elements of the pantomesh are not isosceles trapezoidal elements. In some embodiments, the pantomesh is used to compress breast tissue during an MRI procedure. In some embodiments, the pantomesh is connected to one or more MRI-compatible actuators that facilitate remote control of the amount of compression provided. In some embodiments, the breast-tissue-compression pantomesh is operably connected to a computer that calculates and/or controls the positions and orientations of a plurality of the elements that make up the pantomesh. In some embodiments, the system displays such element positions relative to an MRI image of the patient. In some embodiments, the system calculates and/or controls the position(s) and orientation(s) of one or more medical-procedure probes (e.g., such as a biopsy needle, minimally invasive (e.g., laparoscopic or the like) surgical instrument, treatment-placement devices or the like). In some embodiments, the positions and orientations of the breast-compression cradle relative to the positions and orientations of the medical-procedure probes are used to control the display and/or user-interface controls that block or enable the movement of the various parts of the cradle and/or probe.

BRIEF DESCRIPTION OF THE DRAWINGS

FIG. 1A is a perspective view of a tissue-stabilization device 104 having a tissue-compression cradle 200, according to some embodiments of the present invention.

FIG. 1B is a perspective view of tissue-compression cradle 200 in a relatively open and uncompressed configuration.

FIG. 1C is a perspective view of tissue-compression cradle 200 in a relatively snug compressed configuration.

FIG. 1D is a side (elevational) view of system 101 for MRI guided breast intervention, according to some embodiments of the present invention.

FIG. 1E is a top-down (plan) view of system 101 for MRI guided breast intervention, according to some embodiments of the present invention.

FIG. 2A is a schematic plan view of a pantomesh element 201 (also called a pantomesh cell 201), wherein pantomesh element 201 includes a pair of straight links 211 and 212.

FIG. 2B is a schematic plan view of a pantomesh element 202, wherein pantomesh element 202 includes a pair of bent links 221 and 222.

FIG. 3A is a schematic diagram of a single row pantomesh 301.

FIG. 3B is a schematic diagram of a single row closed pantomesh 302.

FIG. 3C is a schematic diagram of a top view of a four element closed row pantomesh 303.

FIG. 3D is a schematic diagram of the side view of a single row closed pantomesh 303, in the tall and narrow configuration.

FIG. 3E is a schematic diagram of the top view of a single row closed pantomesh 303, in the short and wide configuration.

FIG. 3F is a schematic diagram of the side view of a single row closed pantomesh 303, in the short and wide configuration.

FIG. 5C-2 is a perspective schematic view of a breast-compression cradle 503 having a plurality of tissue-compression members 593, wherein cradle 503 is in an open configuration.

FIG. 6A is a perspective schematic view of an outer ring 601 having a larger-diameter upper ring 621 and alternating diagonal braces 622.

FIG. 6B is a perspective schematic view of an outer ring 602 having a larger-diameter upper ring 621 and a closed conical support brace 624.

FIG. 9 a block diagram of a method 902

FIG. 10.1 is block diagram of a computer 1001.

FIG. 10.2 is block diagram of an MRI machine 1002.

FIG. 10.3 is block diagram of an MRI machine control unit 1003.

FIG. 11.1 is an original drawing of a pantograph.

FIG. 11.2 is a schematic view of lazy tongs.

FIG. 11.3 is a schematic view of Kempe's eight-bar linkage.

FIG. 11.4 is a perspective view of a Camp stool with a four link pair collapsible mechanism.

FIG. 11.5A is a perspective schematic view of deployable antenna mast.

FIG. 11.5B is a perspective schematic view of a single module of a deployable antenna mast.

FIG. 11.5C is a schematic view of a pantograph element used to construct a deployable antenna mast.

FIG. 11.5D is a top schematic view of deployable antenna mast.

FIG. 11.6A is perspective view of a collapsed Hoberman Sphere® toy.

FIG. 11.6B is perspective view of an expanded Hoberman Sphere® toy.

FIG. 11.7A is a perspective schematic view of an expanded radially-collapsing ring of links.

FIG. 11.7B is a perspective schematic view of a collapsed radially-collapsing ring of links.

FIG. 11.8A is a schematic view of pair of general PRRP linkages, as an example of a kinematic interpretation of Hoberman's angulated element.

FIG. 11.8B is a schematic view of a PRRP linkage and its coupler point, as an example of a kinematic interpretation of Hoberman's angulated element.

FIG. 11.9A is a perspective view of a collapsible chair with angled supports.

FIG. 11.9B is a rear view of a collapsible chair with angled supports.

FIG. 11.10 is perspective schematic view of an umbrella.

FIG. 11.11 is a perspective schematic view of an expandable dome.

FIG. 12.1 is a schematic view of straight-link pantograph element.

FIG. 12.2A is a schematic view of a rectangular pantograph element.

FIG. 12.2B is a schematic view of a parallelogram pantograph element.

FIG. 12.3A is a perspective schematic view of five pantograph elements in a closed chain.

FIG. 12.3B is a perspective schematic view of two rows of six pantograph elements in a closed chain.

FIG. 12.4 is a schematic view of an isosceles-trapezoidal, straight-line pantograph element.

FIG. 12.5 is a perspective schematic view of a 2×1 open isosceles pantomesh.

FIG. 13.1 is a perspective schematic view of a solution for a two-row, six-column straight-line pantograph mesh.

FIG. 13.2A is a perspective schematic view of a solution for a pantograph mesh with two specified shapes, in position 1 (wider and shorter).

FIG. 13.2B is a perspective schematic view of a solution for a pantograph mesh with two specified shapes, in position 2 (thinner and taller).

FIG. 13.3 is a schematic view of a four bar analogy to a planar pantograph element.

FIG. 13.4 is a perspective schematic view of a two-row closed chain of quadrilaterals that requires mitered corners in the upper row.

FIG. 13.5A is a schematic view of the first operation of a proof of an impossible pantograph element.

FIG. 13.5B is a schematic view of the final operation of a proof of an impossible pantograph element.

FIG. 13.6A is a schematic view of operation 1 of fixed-angle pantograph-element synthesis.

FIG. 13.6B is a schematic view of operation 2 of fixed-angle pantograph element synthesis.

FIG. 13.6C is a schematic view of operation 3 of fixed-angle pantograph element synthesis.

FIG. 13.6D is a schematic view of operation 4 of fixed-angle pantograph element synthesis.

FIG. 13.7 is a schematic view of opposite-side intersections for a general straight-line pantograph element.

DESCRIPTION OF PREFERRED EMBODIMENTS

Figure 2C:
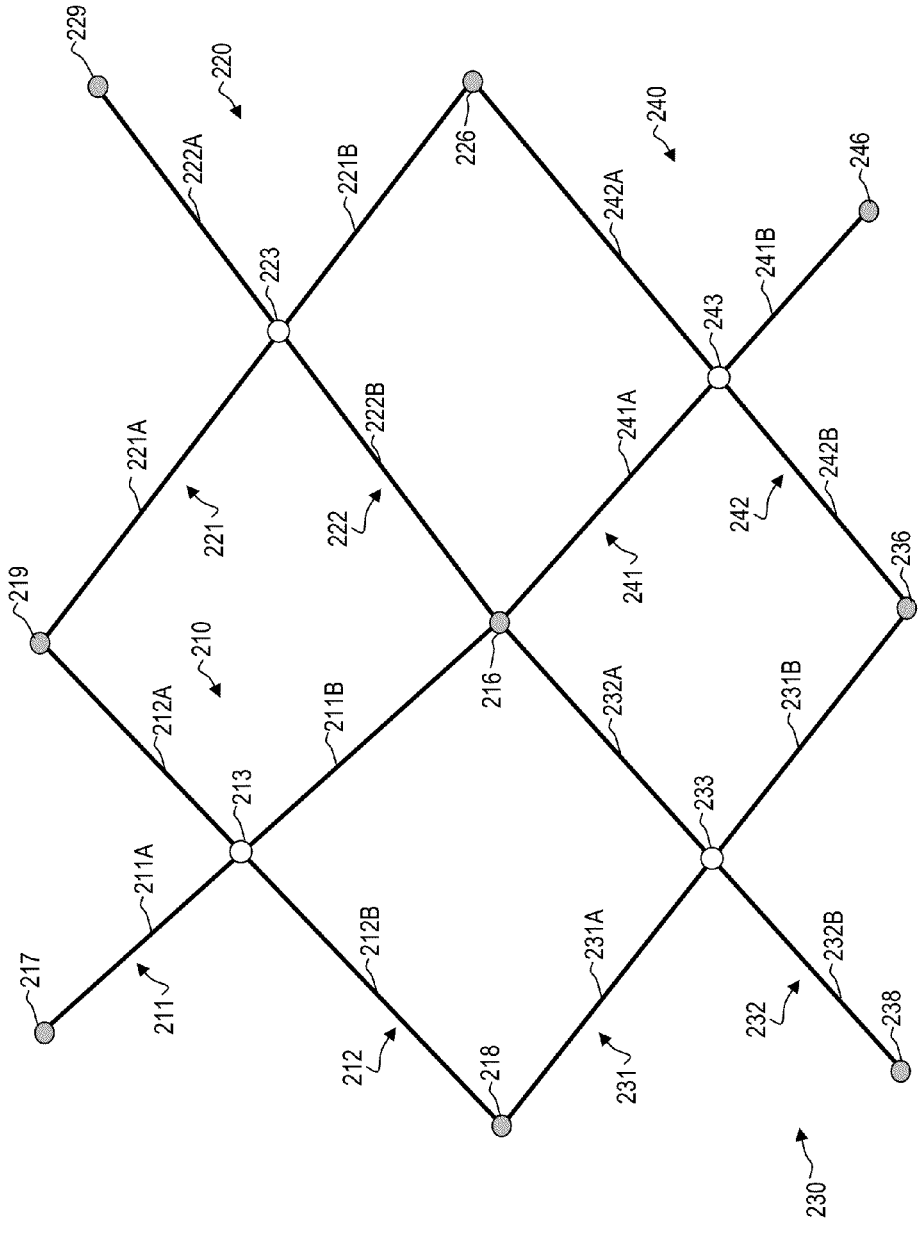
FIG. 2C is a schematic diagram of a pantomesh 203.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

FIG. 1A shows one embodiment of a breast-compression fixture 104 that includes an outer frame 220, a plurality of actuators including a first actuator 227 and a second actuator 229. The breast-compression fixture 104 includes a breast-compression cradle 200, including a plurality of pantomesh elements 210 (in some embodiments, one or more rows of pantomesh elements are connected to one another to form a closed ring (also called a closed pantomesh)), each pantomesh element 210 having two compression members 211 and 212. When in use as an aid to a breast-intervention medical procedure, the chest wall 97 of the patient 99 rests on the breast-compression fixture 104 (or on a platform (not shown here) located just above fixture 104) such that the breast 98 hangs down due to gravity and is surrounded by the closed pantomesh that includes compression members 211 and 212.

In some embodiments of this invention, the closed pantomesh includes four pantomesh elements 210, wherein each pantomesh element 210 includes a pair of links, wherein the pair of links includes a first link 211 and a second link 212, wherein each link has a first end (e.g., the lower ends in FIG. 1A) and a second end (e.g., the upper ends in FIG. 1A). Each pantomesh element 210 also includes a revolute joint 213 that connects a location between the first end and the second end of the first link 211 of the pantomesh element 210 to a location between the first end and the second end of the second link 212 of the pantomesh element 210; and a plurality of spherical joints that includes a first spherical joint 216, second spherical joint 217, spherical third spherical joint 218, and a fourth spherical joint 219. The first spherical joint 216 connects the first end of the first link 211 of the first pantomesh element 210 (e.g., the pantomesh element seen in the center of FIG. 1A); to the first end of the second link of a second pantomesh element 210 (e.g., the pantomesh element seen end-on at the right of FIG. 1A); the second spherical joint 217 connects the second end of the first link 211 of the first pantomesh element to the second end of the second link of the third pantomesh element 210 (e.g., the pantomesh element seen edge-on at the left of FIG. 1A); the third spherical joint 218 connects the first end of the second link 212 of the first pantomesh element to the first end of the first link of the third pantomesh element; and the fourth spherical joint 219 connects the second end of the second link 212 of the first pantomesh element to the second end of the first link of the second pantomesh element. In a similar manner, if four pantomesh elements are implemented, spherical joints connect corresponding links of the second, third and fourth pantomesh elements, not fully visible in FIG. 1A. In other embodiments, this invention includes a plurality of a different number of pantomesh elements, where the number is not equal to four.

FIG. 1B shows the breast compression cradle 200, also shown in FIG. 1A, in an expanded relatively open and uncompressed configuration. In this view, the ring 220 and actuators 227 and 229 are not shown. To achieve this configuration, the actuators 227 and 229 would pull each of a plurality of the spherical joints 227 and 229 in an outward direction (e.g., in some embodiments, in a radially outward direction from a virtual centerline of the breast 98 that extends outward from the patient through a central (e.g., vertical in this view) axis of cradle 200).

FIG. 1C shows the breast compression cradle 200, also shown in FIG. 1A, in a relatively snug compressed configuration. In this view, the ring 220 and actuators 227 and 229 are not shown. To achieve this configuration, the actuators 227 and 229 would push each of a plurality of the spherical joints 227 and 229 in an inward direction (e.g., in some embodiments, in a radially inward direction toward a virtual centerline of the breast 98 that extends outward from the patient through a central (e.g., vertical in this view) axis of cradle 200).

FIG. 1D is a side view of MRI-guided breast-intervention system 101 for MRI-guided breast intervention, according to some embodiments of the present invention. FIG. 1D shows intervention probe 130 in an angled-up position, such that there is an angle between the intervention probe 130 and the frame base 114. In some embodiments, a biopsy needle 132 is at the functional end of probe 130. An intervention probe 130 is attached to probe actuator 125 and arranged to travel inward and outward with respect to the breast-compression fixture 104. In some embodiments, probe actuator 125 is attached to one or more additional actuators to move it, for example up and down and back and forth as shown by the arrows in FIG. 1E.

FIG. 1E is a top-down view of MRI-guided breast-intervention system 101, according to some embodiments of the present invention. In some embodiments, the numbered elements of FIG. 1D are the same as or equivalent to the corresponding elements described for FIG. 1E. In some embodiments, intervention probe 130 further is configured to accept and hold a probe tip 132. In some embodiments, probe tip 132 is a biopsy needle used to take a biopsy sample from a breast 98 of a patient 99 (see FIG. 1B).

FIG. 2A is a schematic plan view of a pantomesh element 201 (also called a pantomesh cell 201), wherein pantomesh element 201 includes a pair of straight links, wherein each link has a first end and a second end, wherein the pair of links includes a first link 211 and a second link 212, a revolute joint 213 which connects a location between the first end and the second end of the first link 211 of the pantomesh element 201 to a location between the first end and the second end of the second link 212 of the pantomesh element 201; and a plurality of spherical joints that includes a first spherical joint 216, second spherical joint 217, spherical third spherical joint 218, and a fourth spherical joint 219. The first link 211 further includes a first segment 211A and a second segment 211B, and the second link 212 further includes a first segment 212A and a second segment 212B. In some embodiments, the first segment 211A of the first link 211 is collinear with the second segment 211B of the first link 211, and the first segment 212A of the second link 212 is collinear with the second segment 212B of the second link 212.

FIG. 2B is a schematic plan view of a pantomesh element 202, wherein pantomesh element 202 includes a pair of bent links, wherein each link has a first end and a second end, wherein the pair of links includes a first bent link 221 and a second bent link 222, a revolute joint 223 which connects a location between the first end and the second end of the first link 221 of the pantomesh element 202 to a location between the first end and the second end of the second link 222 of the pantomesh element 202; and a plurality of spherical joints that includes a first spherical joint 216, second spherical joint 217, spherical third spherical joint 218, and a fourth spherical joint 219. The first bent link 221 further includes a first segment 221A and a second segment 221B that are bent at a non-180-degree angle relative to one another (line segment 221C represents a straight line between the two ends of bent links 221—i.e., a straight line between spherical joints 216 and 217), and the second bent link 222 further includes a first segment 222A and a second segment 222B that, in some embodiments, are bent at a non-180-degree angle relative to one another (line segment 222C represents a straight line between the two ends of bent links 222—i.e., a straight line between spherical joints 218 and 219). In other words, in some embodiments, the first segment 221A of the first link 221 is not collinear with the second segment 221B of the first bent link 221, and/or the first segment 222A of the second bent link 222 is not collinear with the second segment 222B of the second link 222. In some such embodiments, all four segments 221A, 221B, 222A, and 222B are all coplanar. The virtual lines 281 and 282 define a bottom and top edge, respectively, of pantomesh element 202, while virtual lines 283 and 284 define a left and right edge, respectively, of pantomesh element 202. When all four segments 221A, 221B, 222A, and 222B are all coplanar, the various angles define motions of the pantomesh element 202. The angle 291 is between edge 281 and virtual line 222C, the angle 292 is between edge 281 and virtual line 221C, the angle 293 is between edge 283 and virtual line 222C, the angle 294 is between edge 284 and virtual line 221C, the angle 295 is between segment 222B and virtual line 222C, the angle 296 is between segment 221B and virtual line 221C, angle 297 is between virtual line 221C and virtual line 222C, and angle 298 is between segment 221B and segment 222B.

FIG. 2C is a schematic diagram of a pantomesh 203 that has a plurality of pairs of links, wherein each link has a first end and a second end, wherein each pair of links includes a first link and a second link, and wherein the plurality of pairs of links includes a first pair 210 and a second pair 220; a plurality of revolute joints, including a first revolute joint 213 and a second revolute joint 223. The first revolute joint 213 connects a location between the first end and the second end of the first link 211 of the first pair 210 to a location between the first end and the second end of the second link 212 of the first pair 210. The second revolute joint 223 connects a location between the first end and the second end of the first link 221 of the second pair 220 to a location between the first end and the second end of the second link 222 of the second pair 220. In some embodiments, pantomesh 203 further includes a plurality of spherical joints that includes a first spherical joint 216 and a second spherical joint 219, wherein the first spherical joint 216 connects the first end of the first link 211 of the first pair of links 210 to the first end of the second link 222 of the second pair of links 220, and the second spherical joint 219 connects the second end of the second link 212 of the first pair of links 210 to the second end of the first link 221 of the second pair of links 220.

In some embodiments of pantomesh 203, the plurality of pairs of links further includes a third pair 230 and a fourth pair 240, the plurality of revolute joints further includes a third revolute joint 233 and a fourth revolute joint 243, wherein the third revolute joint 233 connects a location between the first end and the second end of the first link 231 of the third pair 230 to a location between the first end and the second end of the second link 232 of the third pair 230, and the fourth revolute joint 243 connects a location between the first end and the second end of the first link 241 of the fourth pair 240 to a location between the first end and the second end of the second link 242 of the fourth pair 240, and the plurality of spherical joints further includes a third spherical joint 218, a fourth spherical joint 226 and a fifth spherical joint 236. The first spherical 216 joint also connects the first end of the second link 232 of the third pair of links to the first end of the first link 241 of the fourth pair of links, the third spherical joint 218 connects the second end of the first link 231 of the third pair of links to the first end of the second link 212 of the first pair of links 230, the fourth spherical joint 226 connects the second end of the second link 242 of the fourth pair 240 to the first end of the first link 221 of the second pair 220, and the fifth spherical joint 236 connects the first end of the first link 231 of the third pair 230 to the first end of the second link 242 of the fourth pair 240.

FIG. 3A shows a single row pantomesh 301 which in some embodiments includes a plurality of pantomesh elements 301, including a first pantomesh element 311, a second pantomesh element 312 and an Nth pantomesh element 319, wherein each pantomesh element is a pantomesh element such as the pantomesh element 201 in FIG. 2A, or the pantomesh element 202 in FIG. 2B. Each of the pantomesh elements is successively connected to the adjacent pantomesh element with corresponding spherical joints.

FIG. 3B shows a single row closed pantomesh 302 which in some embodiments includes a plurality of pantomesh elements including a first pantomesh element 311, a second pantomesh element 312, an $N^{th}$ pantomesh element 319, and an $N-1^{st}$ pantomesh element 318 wherein each pantomesh element is successively connected to the adjacent pantomesh element with corresponding spherical joints and wherein the $N-1^{st}$ pantomesh element further connects to the $N^{th}$ pantomesh element. Each pantomesh element is a pantomesh element such as the pantomesh element 201 in FIG. 2A, or the pantomesh element 202 in FIG. 2B.

In FIG. 3C shows a top view of four-element closed-row pantomesh 303, wherein each pantomesh element includes a first spherical joint 331, a second spherical joint 332, a third spherical joint 333 and a fourth spherical joint 334, and a revolute joint 335.

FIG. 3D shows the side view of a single row closed pantomesh 303, in the tall and narrow configuration.

FIG. 3E shows the top view of a single row closed pantomesh 303, in the short and wide configuration.

FIG. 3F shows the side view of a single row closed pantomesh 303, in the short and wide configuration.

Figure 4:
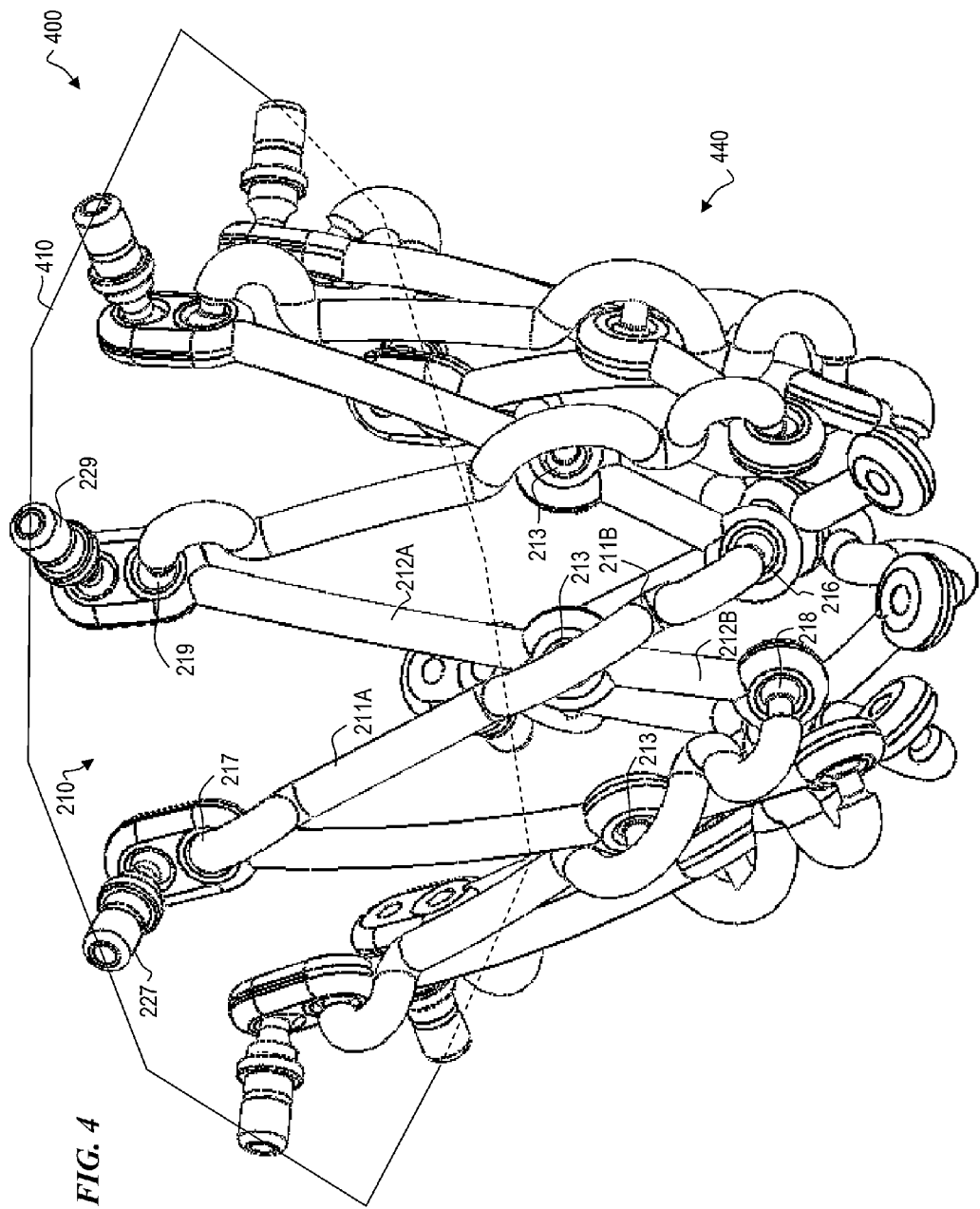
FIG. 4 is a perspective view of a single-row closed-pantomesh tissue-stabilization device 440 that is used for tissue-compression cradle 200, according to some embodiments of the present invention.

FIG. 4 is a perspective view of a single-row closed-pantomesh tissue-stabilization device 440 that is used for tissue-compression cradle 200, according to some embodiments of the present invention. Each element in this FIG. 4 corresponds to a corresponding like-numbered element in FIG. 1A.

Figure 5A:
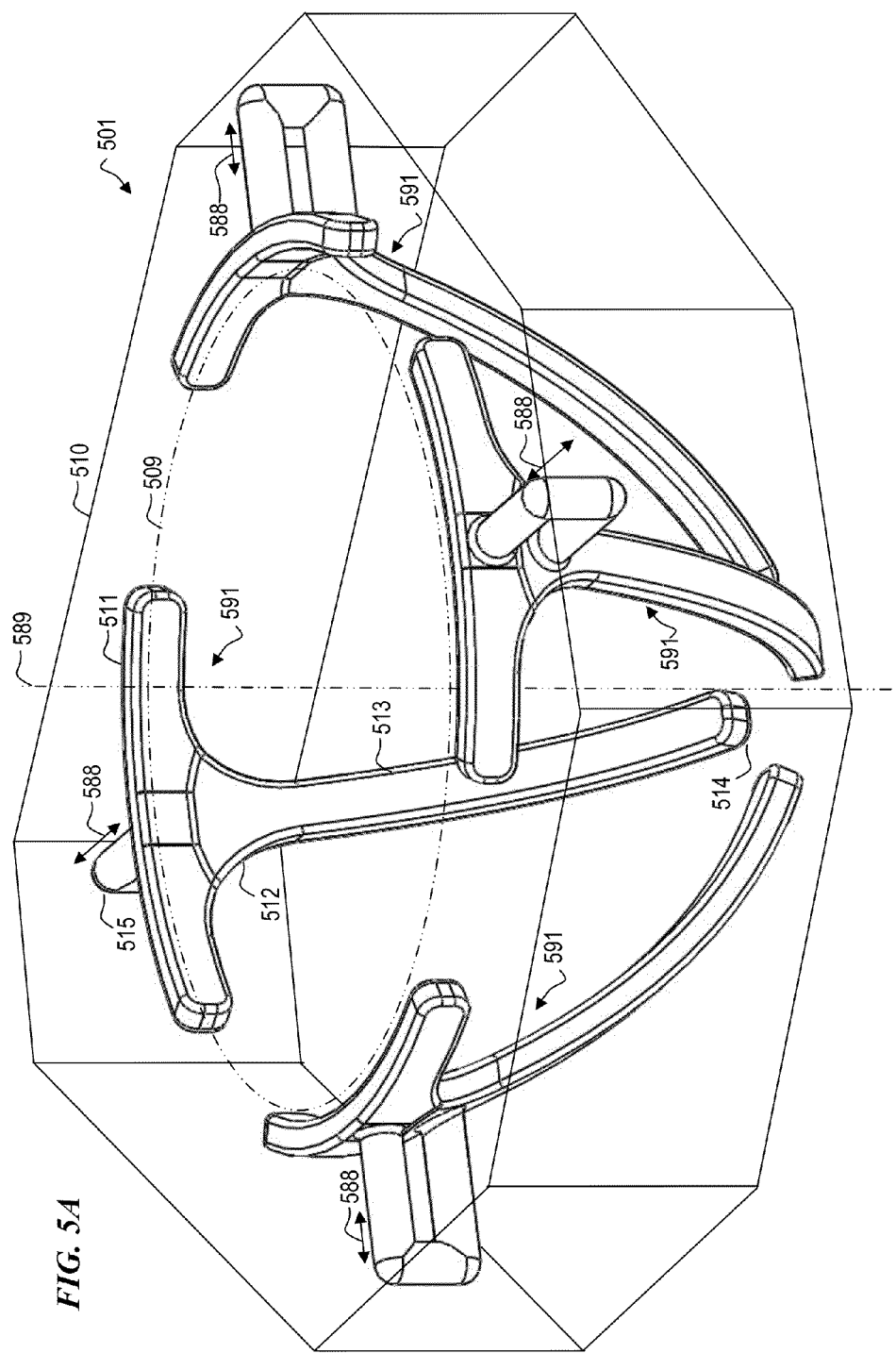
FIG. 5A is a perspective schematic view of a breast-compression cradle 501 having a plurality of tissue-compression members 591.

FIG. 5A is a perspective schematic view of a breast-compression cradle 501 having a plurality of tissue-compression members 591 (in the embodiment shown, four tissue-compression members 591 are used, while in other embodiments, other numbers of tissue-compression members 591 are used). In some embodiments, cradle 501 includes a plurality of three or more tissue-compression members 591 that are configured to be moved to compress bodily tissue of a portion of a patient (e.g., a breast). In some embodiments, breast-compression cradle 501 captures and compresses the patient's breast as the breast hangs down from the patient (due to gravity) when the patient is lying in a prone (face-down) position. In some embodiments, the plurality of tissue-compression members 591 are interconnected to one another via respective connections to cradle fixture 510, and cradle 501 compresses the patient's breast by moving the plurality of tissue-compression members 591 radially inward along a direction indicated by line 588 (away from the perimeter of cradle fixture 510 and toward a center line 589 that runs vertically through cradle 501). When the plurality of tissue-compression members 591 are moved radially outward, compression is removed and the breast is released. In some embodiments, tissue-compression members 591 are moved radially inward and outward along directions indicated by the respective lines 588 by actuators (in some embodiments, for example, piezoelectric actuators, not shown here) connected to tissue-compression members 591 via an actuator connection 515. In some embodiments, actuator connection 515 is a closed shape (e.g., approximately C-shaped), and each actuator connection 515 is connected to, and moved by a single actuator. In some embodiments, each actuator is independently moveable under computer control.

In some embodiments, each one of the plurality of tissue-compression members 591 includes a circumferential element 511 that curves around at least a portion of a circumference 509 formed by the plurality of tissue-compression members 591. In some embodiments, one or more of the tissue-compression members 591 can also be moved up and down in order to better conform to the patient's rib cage (e.g., in some such embodiments, one can be moved upward under the arm of the patient to better compress and obtain MRI images of breast and lymph tissue there). In some embodiments, one or more of the circumferential elements 511 is springy and/or pliable, in order to provide comfort and/or a snugger fit. In some embodiments, actuator connection 515 connects to circumferential element 511 such that circumferential element 511 moves radially inward during compression. In some embodiments, each one of the plurality of tissue-compression members 591 includes a stem-shaped compression element 513 that includes an upper end 512 (attached to a respective circumferential element 511) and a free lower end 514. In some embodiments, one or more of the stem elements 513 is springy and/or pliable, in order to provide comfort and/or a snugger fit. In some embodiments, each stem 513 has a curved configuration such that when cradle 501 is in a compressed state (as illustrated in FIG. 5A), the lower end 514 of stem 513 is closer to center line 589 than the upper end 512 of stem 513. In some embodiments, stem 513 connects to its corresponding circumferential element 511 at the center of circumferential element 511 such that tissue-compression member 591 forms a T-shape (as illustrated in FIG. 5A). In other embodiments (not shown), stem 513 connects to its corresponding circumferential element 511 at one end of circumferential element 511 such that tissue-compression member 591 forms an inverted L-shape, or connects to its corresponding circumferential element 511 at some other suitable location (e.g., between the center and the end) of circumferential element 511.

In some embodiments, each one of the plurality of tissue-compression members 591 is made of a magnetic-resonance imaging (MRI)-safe material (e.g., nitinol or polymer or other compatible material). In some embodiments, tissue-compression members 591 include embedded MRI coils or coil portions, or have such coil portions attached to them.

Figure 5B:
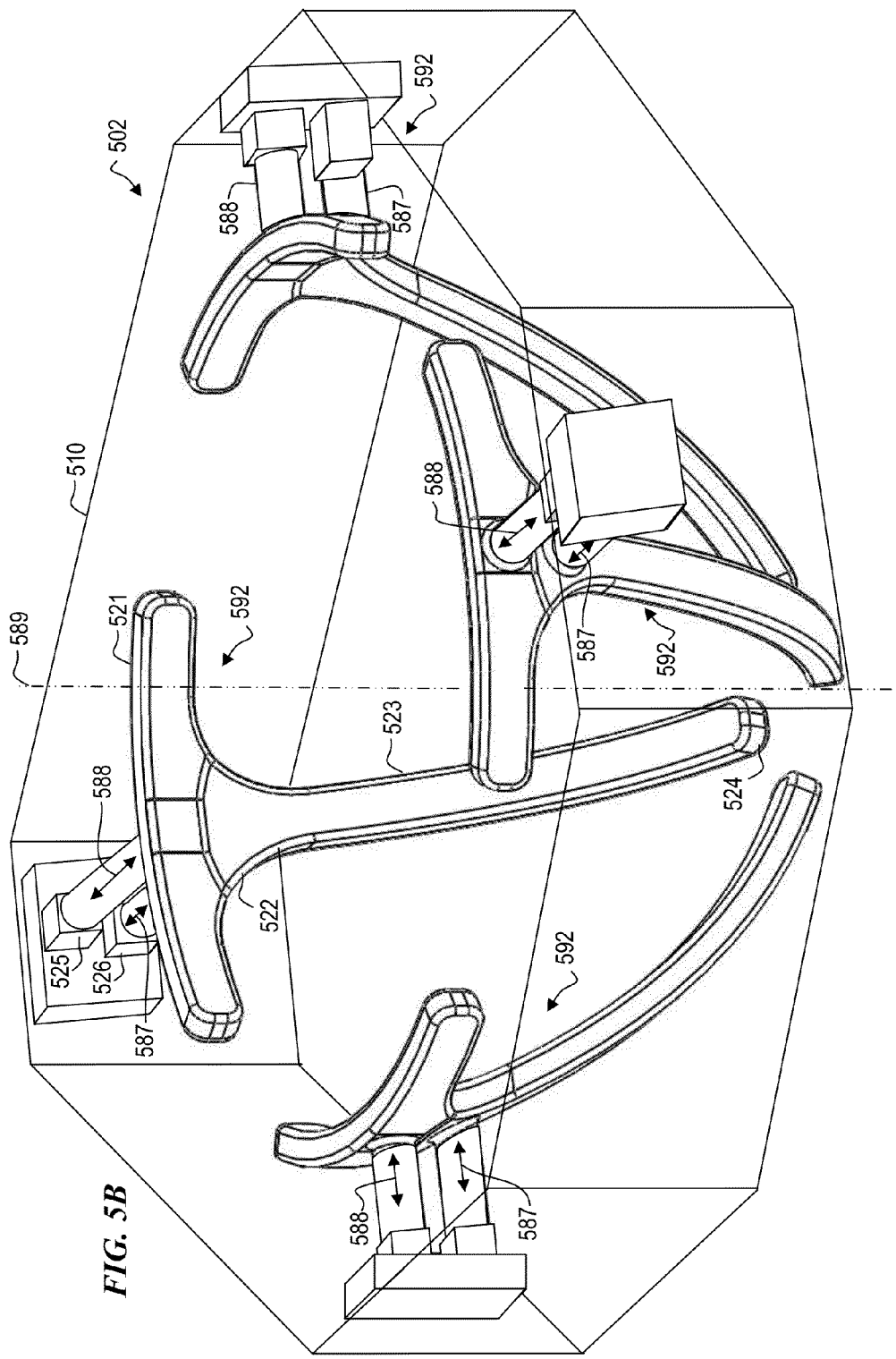
FIG. 5B is a perspective schematic view of a breast-compression cradle 502 having a plurality of tissue-compression members 592.

FIG. 5B is a perspective schematic view of a breast-compression cradle 502 having a plurality of tissue-compression members 592 (in the embodiment shown, four tissue-compression members 592 are used, while in other embodiments, other numbers of tissue-compression members 592 are used). In some embodiments, each one of the plurality of tissue-compression members 592 includes a circumferential element 521 that curves around at least a portion of a circumference 509 formed by the plurality of tissue-compression members 592. In some embodiments, one or more of the tissue-compression members 592 can also be moved up and down in order to better conform to the patient's rib cage (e.g., in some such embodiments, one can be moved upward under the arm of the patient to better compress and obtain MRI images of breast and lymph tissue there). In some embodiments, one or more of the circumferential elements 521 is springy and/or pliable, in order to provide comfort and/or a snugger fit. In some embodiments, each one of the plurality of tissue-compression members 592 includes a stem-shaped compression element 523 that includes an upper end 522 (attached to a respective circumferential element 521) and a free lower end 524. In some embodiments, each stem 523 has a curved configuration such that when cradle 502 is in a compressed state (as illustrated in FIG. 5B), the lower end 524 of stem 523 is closer to center line 589 than the upper end 522 of stem 523. In some embodiments, stem 523 connects to its corresponding circumferential element 521 at the center of circumferential element 521 such that tissue-compression member 592 forms a T-shape (as illustrated in FIG. 5B). In other embodiments (not shown), stem 523 connects to its corresponding circumferential element 521 at one end of circumferential element 521 such that tissue-compression member 592 forms an inverted L-shape, or connects to its corresponding circumferential element 521 at some other suitable location (e.g., between the center and the end) of circumferential element 521.

In some embodiments, at least one of the plurality of tissue-compression members 592 includes two actuators (in some embodiments, for example, piezoelectric actuators). In some embodiments, for example, at least one of the plurality of tissue-compression members 592 includes an upper actuator 525 and a lower actuator 526. In some embodiments, upper actuator 525 is configured to move radially inward and outward along a direction indicated by line 588 such that circumferential element 521 moves radially inward and outward. In some embodiments, lower actuator 526 is configured to move radially inward and outward along a direction indicated by line 587 such that stem 523 can be tilted relative to circumferential element 521.

In some embodiments, each one of the plurality of tissue-compression members 592 is made of a magnetic-resonance imaging (MRI)-safe material (e.g., nitinol or polymer or other compatible material). In some embodiments, tissue-compression members 592 include embedded MRI coils or coil portions, or have such coil portions attached to them.

Figures 1, 5C:
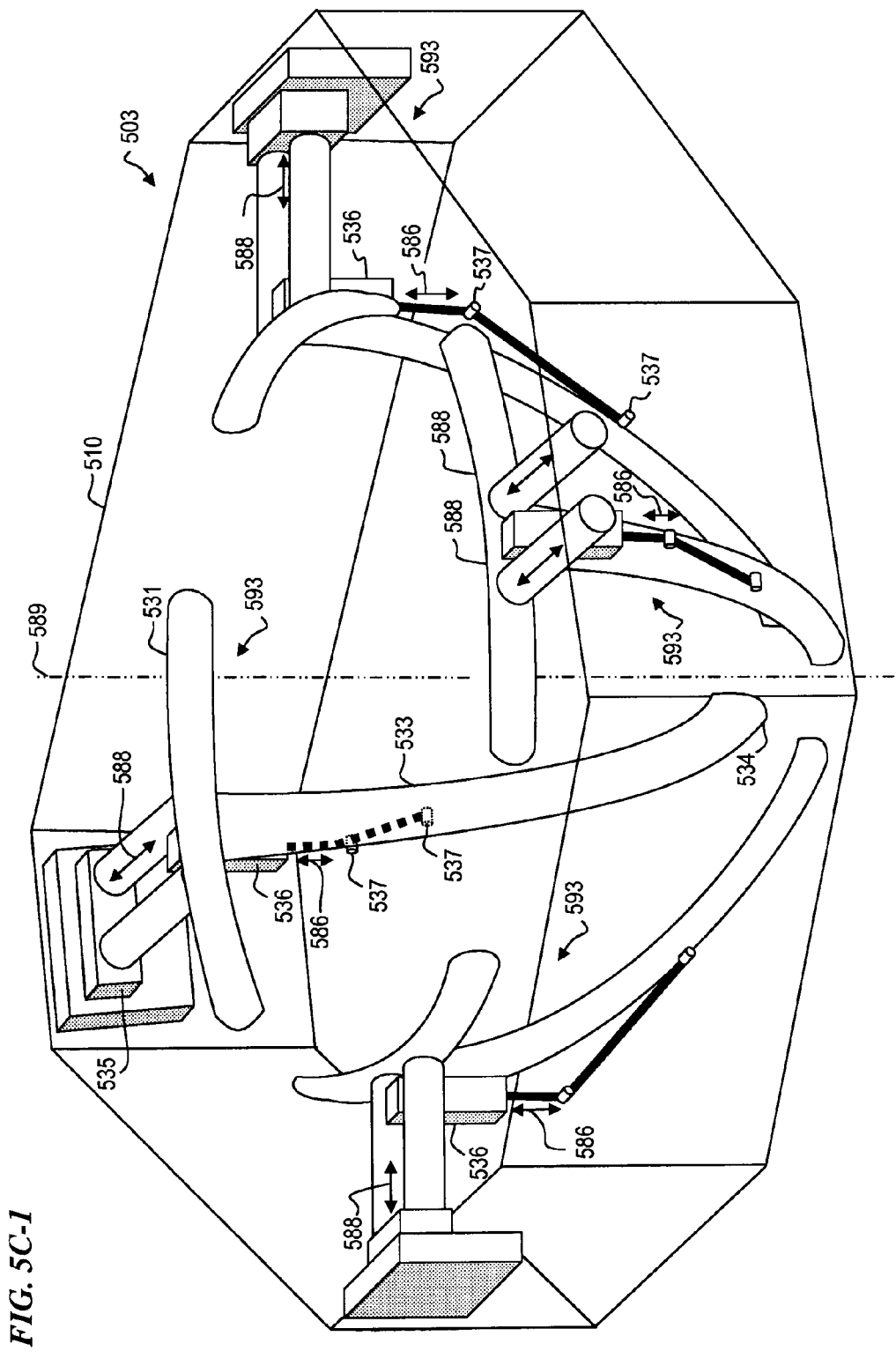
FIG. 5C-1 is a perspective schematic view of a breast-compression cradle 503 having a plurality of tissue-compression members 593, wherein cradle 503 is in a compressed configuration.
Figures 2, 5C:
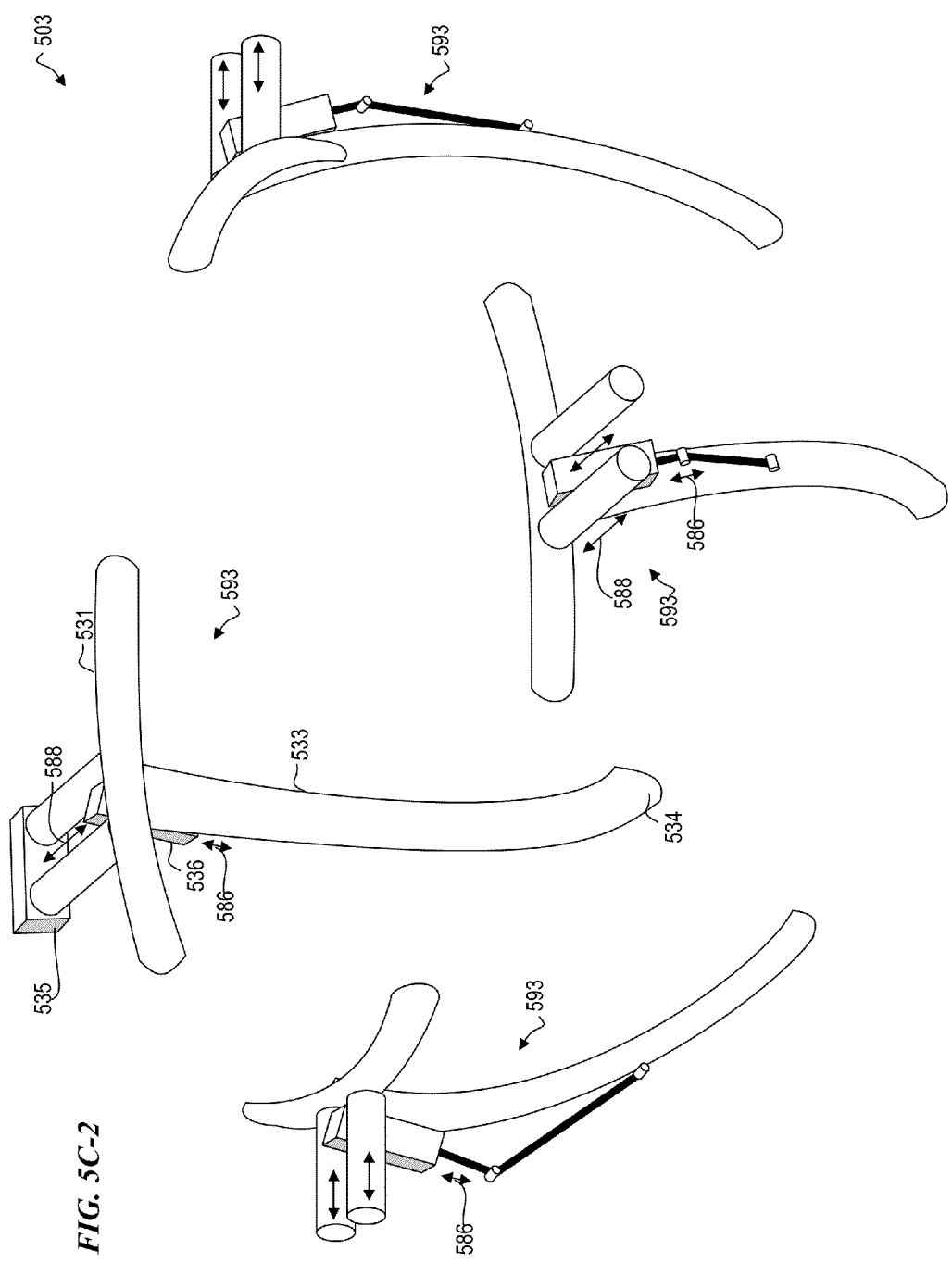

FIG. 5C-1 is a perspective schematic view of a breast-compression cradle 503 having a plurality of tissue-compression members 593 (in the embodiment shown, four tissue-compression members 593 are used, while in other embodiments, other numbers of tissue-compression members 593 are used). In some embodiments, each one of the plurality of tissue-compression members 593 includes a circumferential element 531 that curves around at least a portion of a circumference 509 formed by the plurality of tissue-compression members 593. In some embodiments, one or more of the tissue-compression members 593 can also be moved up and down in order to better conform to the patient's rib cage (e.g., in some such embodiments, one can be moved upward under the arm of the patient to better compress and obtain MRI images of breast and lymph tissue there). In some embodiments, one or more of the circumferential elements 531 is springy and/or pliable, in order to provide comfort and/or a snugger fit. In some embodiments, each one of the plurality of tissue-compression members 593 includes a stem-shaped compression element 533 that includes an upper end 532 (attached to a respective circumferential element 531) and a free lower end 534. In some embodiments, one or more of the stem elements 533 is springy and/or pliable, in order to provide comfort and/or a snugger fit. In some embodiments, stem 533 has a curved configuration such that when cradle 503 is in a compressed state (as illustrated in FIG. 5C-1), the lower end 534 of stem 533 is closer to center line 589 than the upper end 532 of stem 533. In some embodiments, stem 533 connects to its corresponding circumferential element 531 at the center of circumferential element 531 such that tissue-compression member 593 forms a T-shape (as illustrated in FIGS. 5C-1 and 5C-2). In other embodiments (not shown), stem 533 connects to its corresponding circumferential element 531 at one end of circumferential element 531 such that tissue-compression member 593 forms an inverted L-shape, or connects to its corresponding circumferential element. 531 at some other suitable location (e.g., between the center and the end) of circumferential element 531.

In some embodiments, at least one of the plurality of tissue-compression members 593 includes two actuators (in some embodiments, for example, piezoelectric actuators). In some embodiments, for example, at least one of the plurality of tissue-compression members 593 includes a first actuator 535 and a second actuator 536. In some embodiments, first actuator 535 is configured to move radially inward and outward along a direction indicated by line 588 such that circumferential element 531 moves radially inward and outward. In some embodiments, second actuator 536 includes a hinged mechanism 537 that connects actuator 536 to stem 533, and actuator 536 is configured to move vertically up and down along a direction indicated by line 586 such that stem 533 can be tilted relative to circumferential element 531. FIG. 5C-1 illustrates a compressed configuration of cradle 503; wherein actuator 525 is moved radially inward (toward center line 589) such that circumferential element 531 is moved radially inward toward center line 589 and actuator 536 is moved vertically downward such that stem 533 is tilted in toward center line 589. FIG. 5C-2 illustrates an open configuration of cradle 503, wherein actuator 525 is moved radially outward (away from center line 589) and actuator 536 is moved vertically upward such that circumferential element 531 and stem 533 are both moved radially outward from center line 589.

In some embodiments, each one of the plurality of tissue-compression members 593 are made of a magnetic-resonance imaging (MRI)-safe material (e.g., nitinol or polymer or other compatible material). In some embodiments, tissue-compression members 593 include embedded MRI coils or coil portions, or have such coil portions attached to them.

Figure 5D:
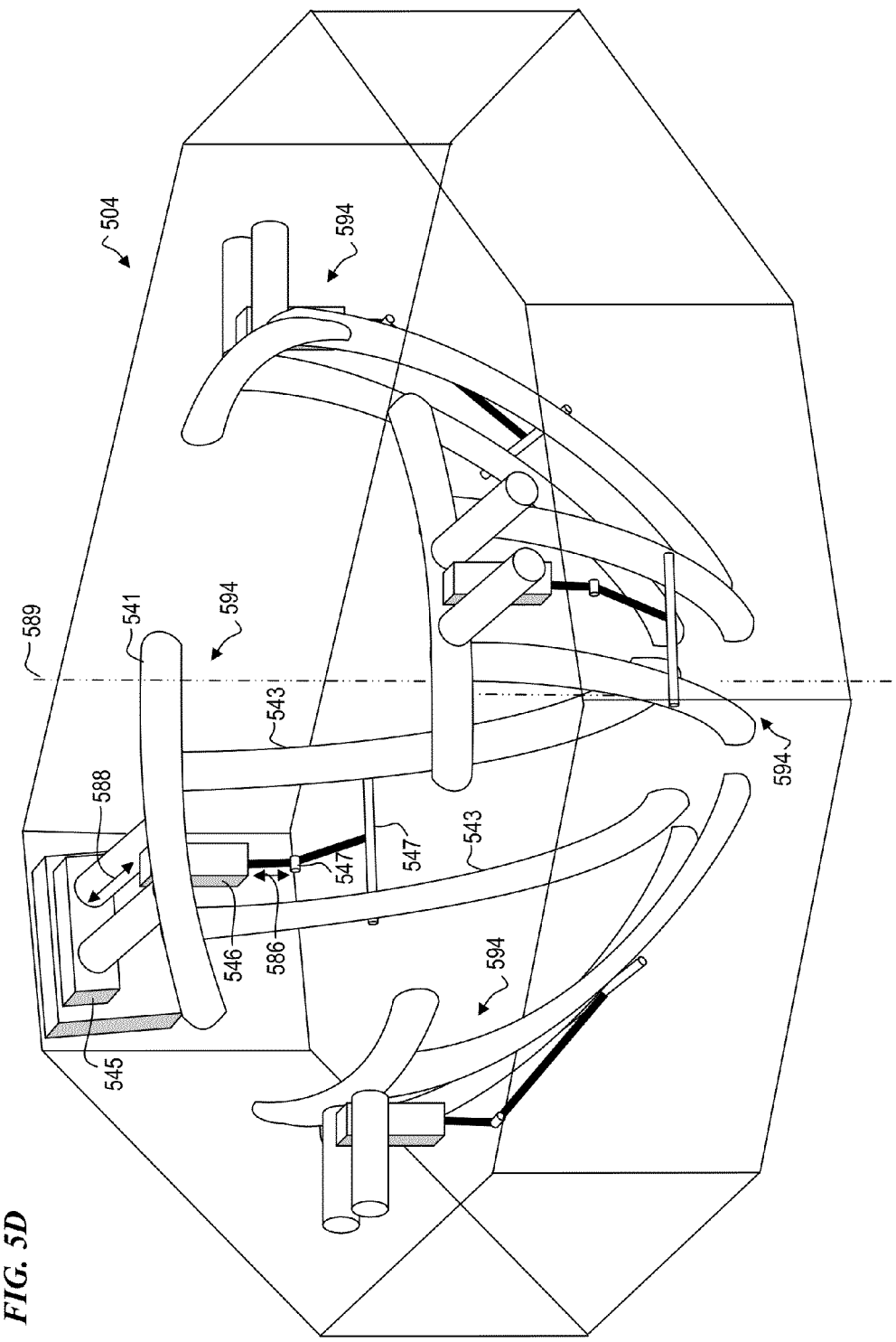
FIG. 5D is a perspective schematic view of a breast-compression cradle 504 having a plurality of tissue-compression members 594.

FIG. 5D is a perspective schematic view of a breast-compression cradle 504 having a plurality of tissue-compression members 594 (in the embodiment shown, four tissue-compression members 594 are used, while in other embodiments, other numbers of tissue-compression members 594 are used). In some embodiments, each one of the plurality of tissue-compression members 594 includes a circumferential element 541 that curves around at least a portion of a circumference 509 formed by the plurality of tissue-compression members 594. In some embodiments, one or more of the tissue-compression members 594 can also be moved up and down in order to better conform to the patient's rib cage (e.g., in some such embodiments, one can be moved upward under the arm of the patient to better compress and obtain MRI images of breast and lymph tissue there). In some embodiments, one or more of the circumferential elements 541 is springy and/or pliable, in order to provide comfort and/or a snugger fit.

In some embodiments, each one of the plurality of tissue-compression members 594 includes two or more stem-shaped compression elements 543, wherein each one of the two or more stems 543 includes an upper end 542 (attached to a respective circumferential element 541) and a free lower end 544. In some embodiments, one or more of the stem elements 543 is springy and/or pliable, in order to provide comfort and/or a snugger fit. In some embodiments, the two or more stems 543 connect to circumferential element 541 in an evenly-distributed manner (e.g., in some embodiments, as illustrated in FIG. 5D, tissue-compression member 594 includes a first stem 543 and a second stem 543, wherein first stem 543 is connected to circumferential element 541 at a location on the left side of circumferential element 541, wherein second stem 543 is connected to circumferential element 541 at a location on the right side of circumferential element 541, and wherein first stem 543 and second stem 543 are equidistant from the center of circumferential element 541). In other embodiments (not shown), the two or more stems 543 are connected to circumferential element 541 in some other suitable manner (e.g., both stems 543 are located on one side of circumferential element 541).

In some embodiments, stems 543 have a curved configuration such that when cradle 504 is in a compressed state (as illustrated in FIG. 5D), the lower end 544 of stems 543 is closer to center line 589 than the upper end 542 of stems 543. In some embodiments, at least one of the plurality of tissue-compression members 594 includes two actuators (in some embodiments, for example, piezoelectric actuators). In some embodiments, for example, at least one of the plurality of tissue-compression members 594 includes a first actuator 545 and a second actuator 546. In some embodiments, first actuator 545 is configured to move radially inward and outward along a direction indicated by line 588 such that circumferential element 541 moves radially inward and outward. In some embodiments, second actuator 546 includes a hinged mechanism 547 that connects actuator 546 to stems 543, and actuator 546 is configured to move vertically up and down along a direction indicated by line 586 such that stems 543 can be tilted relative to circumferential element 541.

In some embodiments, each one of the plurality of tissue-compression members 594 are made of a magnetic-resonance imaging (MRI)-safe material (e.g., nitinol or polymer or other compatible material). In some embodiments, tissue-compression members 594 include embedded MRI coils or coil portions, or have such coil portions attached to them.

Figure 5E:
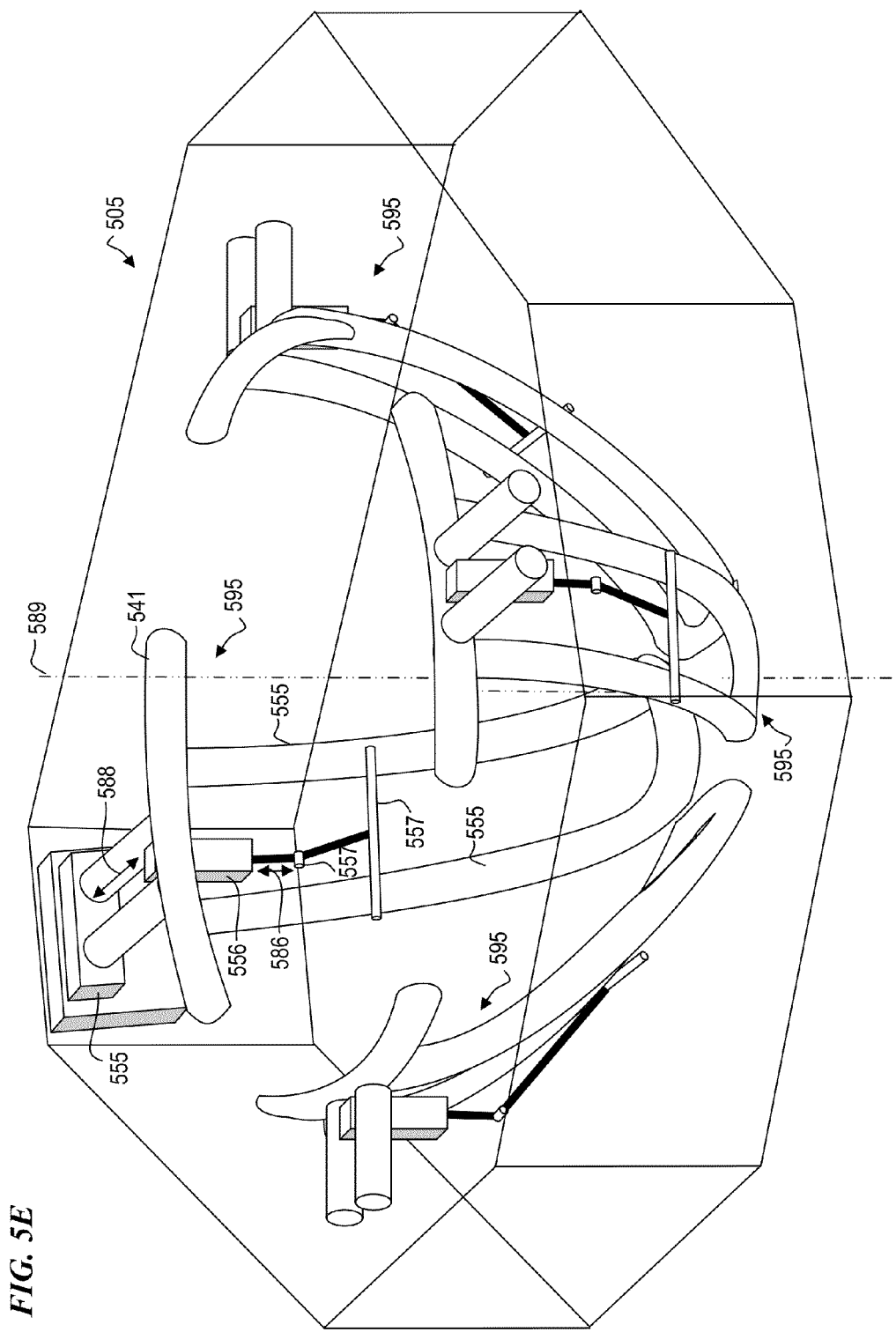
FIG. 5E is a perspective schematic view of a breast-compression cradle 505 having a plurality of tissue-compression members 595.

FIG. 5E is a perspective schematic view of a breast-compression cradle 505 having a plurality of tissue-compression members 595 (in the embodiment shown, four tissue-compression members 595 are used, while in other embodiments, other numbers of tissue-compression members 595 are used). In some embodiments, each one of the plurality of tissue-compression members 595 includes a circumferential element 551 that curves around at least a portion of a circumference 509 formed by the plurality of tissue-compression members 595. In some embodiments, one or more of the tissue-compression members 595 can also be moved up and down in order to better conform to the patient's rib cage (e.g., in some such embodiments, one can be moved upward under the arm of the patient to better compress and obtain MRI images of breast and lymph tissue there). In some embodiments, one or more of the circumferential elements 551 is springy and/or pliable, in order to provide comfort and/or a snugger fit. In some embodiments, each one of the plurality of tissue-compression members 595 includes a stem-shaped compression element 553, wherein stem 553 includes two upper ends 552 and a free lower end 554 such that stem 553 forms a U-Shape (in some embodiments, for example, upper ends 552 of the U-shaped stem 553 connect to circumferential element 551).

In some embodiments, stem 553 has a curved configuration such that when cradle 505 is in a compressed state (as illustrated in FIG. 5E), the lower end 554 of stem 553 is closer to center line 589 than the upper ends 552 of stem 553. In some embodiments, at least one of the plurality of tissue-compression members 595 includes two actuators (in some embodiments, for example, piezoelectric actuators). In some embodiments, for example, at least one of the plurality of tissue-compression members 595 includes a first actuator 555 and a second actuator 556. In some embodiments, first actuator 555 is configured to move radially inward and outward along a direction indicated by line 588 such that circumferential element 551 moves radially inward and outward. In some embodiments, second actuator 556 includes a hinged mechanism 557 that connects actuator 556 to stem 553, and actuator 556 is configured to move vertically up and down along a direction indicated by line 586 such that stem 553 can be tilted relative to circumferential element 551.

In some embodiments, each one of the plurality of tissue-compression members 595 are made of a magnetic-resonance imaging (MRI)-safe material (e.g., nitinol or polymer or other compatible material). In some embodiments, tissue-compression members 595 include embedded MRI coils or coil portions, or have such coil portions attached to them.

FIG. 6A is a perspective schematic view of an outer ring 601 having a larger-diameter upper ring 621 and alternating diagonal braces 622.

FIG. 6B is a perspective schematic view of an outer ring 602 having a larger-diameter upper ring 621 and a closed conical support brace 624.

Figure 7:
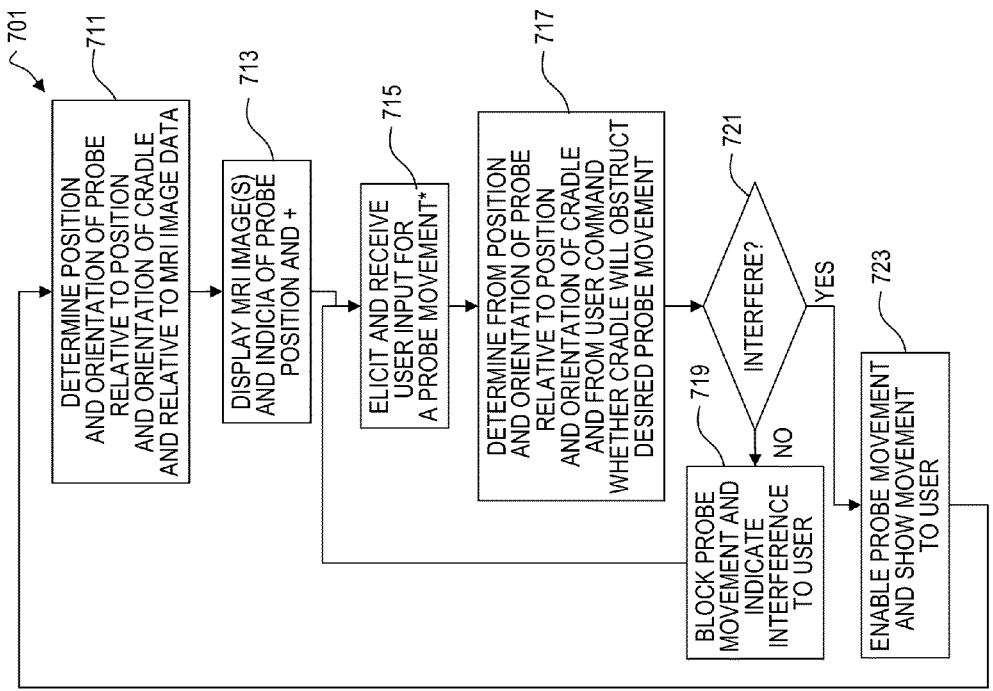
FIG. 7 is a flow-chart diagram of method 701 for performing an MRI-guided breast intervention, according to some embodiments of the present invention.

FIG. 7 is a flow-chart diagram of method 701 for performing an MRI-guided breast intervention, according to some embodiments of the present invention.

Figure 8:
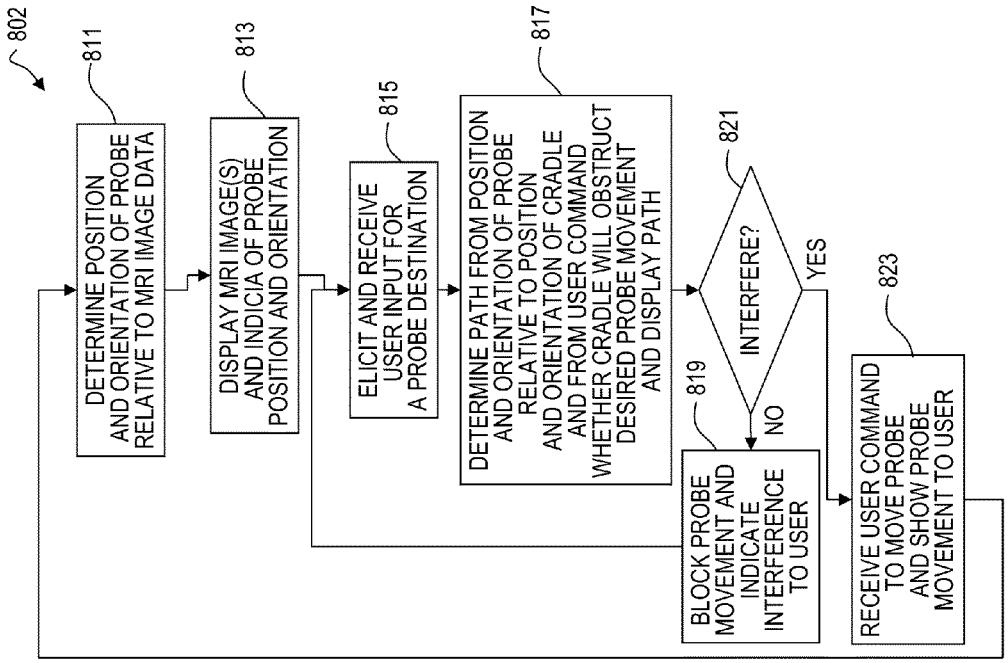
FIG. 8 is a flow-chart diagram of method 801 for performing an MRI-guided breast intervention, according to some embodiments of the present invention.

FIG. 8 is a flow-chart diagram of method 801 for performing an MRI-guided breast intervention, according to some embodiments of the present invention.

FIG. 9 a block diagram of a method 902 of computing the solution set of a pantomesh. A computer-readable medium having instructions stored thereon for causing a suitably programmed information processor to execute a method that comprises:
(a) determining an error set that includes at least one error 911, wherein the error-set value indicates at least one of
an error in a distance between two links of at least one of the pantomesh elements,
a mobility error of the pantomesh,
a bent-link bend angle, and
a link-length error;
(b) receiving a solution set 913 of a plurality of variables describing a pantomesh;
(c) computing a new value of the error set at the solution set 915;
(d) comparing 917 at least one of
(i) the new value of the error set relative to an acceptable value of the error set, and
(ii) a change in the new value of the error set relative to an acceptable amount of change in value of the error set; and
(e) if one or more criteria of the compare have been met 919, outputting the solution set 927,
(f) else:
calculating a gradient of the error set 921 at the solution set, calculating a new search direction based on a current and a previous gradient 923, and searching in the calculated new search direction to determine a new solution set 925 having a new lowest total error along the new search direction and iteratively going to (c) 915.

FIG. 10.1 is block diagram of a computer 1001 that includes an input unit 1010 and a display 1011. In some embodiments, the methods of the present invention are implemented at least partially as programs that execute on computer 1001. In some embodiments, the computer readable media 1020 includes instructions stored thereon for causing computer 1001 to execute the methods of some embodiments of the present invention.

FIG. 10.2 is block diagram of an MRI machine 1002, wherein a system 101 (see FIG. 1D and FIG. 1E described above) is used in MRI machine 1002, and includes at least a first, second and third pantomesh elements (each having a pair of pantomesh links) 210. In some embodiments, the MRI machine 1002 includes a computer 1001 such as shown in FIG. 10.1, and/or control unit 1003 as shown in FIG. 10.3.

FIG. 10.3 is a block diagram of a control unit 1003, according to some embodiments of the present invention. In some embodiments, control unit 1003 includes a real-time control system 910 having a controller firmware system 920 for controlling the actuators of an MRI-guided breast-intervention apparatus of the present invention and, optionally, a real-time operating system (RTOS) 921. In some embodiments, controller firmware system 920 includes a motor driver system 930, a position feedback system 940, and an error-handling system 950. In some embodiments, RTOS 921 includes an error-handling system 931, a position-feedback-differential system 941, and a fiducial-markers-position-calculation system 951. In some embodiments, control unit 1003 further includes a user interface system 912 having a procedure planning system 922 and a magnetic resonance (MR) image display system 923. In some embodiments, procedure planning system 922 includes a desired-position input system 932, a measured-position coordinate outputting system 942, and a user-notification outputting system 952. In some embodiments, MR-image-display system 923 includes an image-from-scanner inputting system 933, a robot-display inputting system 943, a procedure-plan inputting system 963, and an image-display system 953 configured to display a superimposed composite image of the MRI image, the robot-display image, and the procedure-plan image.

In some embodiments of the computer-readable media described herein that have instructions stored thereon for causing one or more of the methods described herein to be executed, the instructions further facilitate the method to be executed on a computer at a location remote from a user, and to be controlled by the user across the internet.

In some embodiments of the computer-controlled apparatus described herein, the apparatus includes a computer at a location remote from a user, wherein the apparatus's limitations include programmed routines that run on the computer and are controlled by the user across the internet.

In some embodiments, the present invention provides a method for fabricating a pantomesh. The method includes providing a plurality of pairs of links, wherein each link has a first end and a second end, wherein each pair of links includes a first link and a second link, and wherein the plurality of pairs of links includes a first pair and a second pair, providing a plurality of revolute joints, including a first revolute joint and a second revolute joint, providing a plurality of spherical joints includes a first spherical joint and a second spherical joint. The method further includes connecting a location between the first end and the second end of the first link of the first pair to a location between the first end and the second end of the second link of the first pair using the first revolute joint, connecting a location between the first end and the second end of the first link of the second pair to a location between the first end and the second end of the second link of the second pair using the second revolute joint, connecting the first end of the first link of the first pair of links to the first end of the second link of the second pair of links using the first spherical joint, and connecting the second end of the second link of the first pair of links to the second end of the first link of the second pair of links using the second spherical joint.

In some embodiments of the method, the providing of the plurality of pairs of links further includes providing a third pair and a fourth pair, the providing the plurality of revolute joints further includes providing a third revolute joint and a fourth revolute joint, and the providing of the plurality of spherical joints further includes providing a third spherical joint. The method further includes: connecting a location between the first end and the second end of the first link of the third pair to a location between the first end and the second end of the second link of the third pair using the third revolute joint, connecting a location between the first end and the second end of the first link of the fourth pair to a location between the first end and the second end of the second link of the fourth pair using the fourth revolute joint, connecting the first end of the first link of the third pair of links to the first end of the second link of the fourth pair of links, using the second spherical joint, and connecting the second end of the second link of the third pair of links to the second end of the first link of the fourth pair of links using the third spherical joint.

In some embodiments, the present invention provides an apparatus that includes a pantomesh 200 which has a plurality of pairs of links, wherein each link has a first end and a second end, wherein each pair of links includes a first link and a second link, and wherein the plurality of pairs of links includes a first pair 210 and a second pair 220; a plurality of revolute joints, including a first revolute joint 213 and a second revolute joint 223, wherein the first revolute joint 213 connects a location between the first end and the second end of the first link 211 of the first pair 210 to a location between the first end and the second end of the second link 212 of the first pair 210, and the second revolute joint 223 connects a location between the first end and the second end of the first link 221 of the second pair 220 to a location between the first end and the second end of the second link 222 of the second pair 220; and a plurality of spherical joints that includes a first spherical joint 216 and a second spherical joint 219, wherein the first spherical joint 216 connects the first end of the first link 211 of the first pair of links 210 to the first end of the second link 222 of the second pair of links 220, and the second spherical joint 219 connects the second end of the second link 212 of the first pair of links 210 to the second end of the first link 221 of the second pair of links 220.

In some embodiments, the plurality of pairs of links further includes a third pair 230 and a fourth pair 240, the plurality of revolute joints further includes a third revolute joint 233 and a fourth revolute joint 243, wherein the third revolute joint 233 connects a location between the first end and the second end of the first link 231 of the third pair 230 to a location between the first end and the second end of the second link 232 of the third pair 230, and the fourth revolute joint 243 connects a location between the first end and the second end of the first link 241 of the fourth pair 240 to a location between the first end and the second end of the second link 242 of the fourth pair 240, and the plurality of spherical joints further includes a third spherical joint 218, a fourth spherical joint 226 and a fifth spherical joint 236. The first spherical 216 joint also connects the first end of the second link 232 of the third pair of links to the first end of the first link 241 of the fourth pair of links, the third spherical joint 218 connects the first end of the first link 231 of the third pair of links to the second end of the second link 212 of the first pair of links 230, the fourth spherical joint 226 connects the first end of the second link 242 of the fourth pair 240 to the second end of the first link 221 of the second pair 220, and the fifth spherical joint 236 connects the second end of the first link 231 of the third pair 230 to the second end of the second link 242 of the fourth pair 240.

Pantomeshes: An Introduction

The pantograph has a long history in kinematics; it is one of the oldest multi-link examples of displacement magnification. Early uses were for transcription, then for collapsible structures, and even for children's toys. Many pantograph-style linkages have been developed using multiple pantograph-like units that obey certain geometric restrictions, but have yet to be described in a general fashion. A pantomesh is an assemblage of multiply-connected pantograph elements, using the most basic of requirements: mobility of the assembled links.

A pantograph is an assembly of links often used for copying or scaling drawings. (The term pantograph is also used for electrical power transmission from overhead lines for electric trains [J. Q. Brown, "Trolley," Jul. 5, 1904. U.S. Pat. No. 764,224 (which is incorporated herein by reference)], but that linkage will not be discussed here.) Typically, four links are arranged in a parallelogram fashion as shown in FIG. 11.1, original drawing of a pantograph [C. Scheiner, *Pantographice seu Ars delineandi res quaslibet per parallelogrammum lineare seu cavum, mechanicum, mobile*. Rome: Ludovico Grigani, 1631]. A pantograph element may be part of this pantograph; here it is defined as a pair of two links joined by a central pivot joint. This pair of links is also referred to as a scissor pair or duplet in related literature [A. Kaveh and A. Davaran, "Analysis of pantograph foldable structures," Computers & Structures, vol. 59, no. 1, p. 131, 1996]. As used herein, a "pantomesh" is an articulated surface created by connecting pantograph elements in a patchwork fashion, using principles of pantograph construction and exhibiting single degree-of-freedom pantograph-like motion (the single degree of freedom is as result of each pair of links in a pantomesh element being joined by revolute joint)

As used herein, a "linkage" contains links connected by joints such as pins or sliders. In three-dimensional space, a link's position and orientation may be specified exactly by six parameters: three positional coordinates (e.g., x, y, and z) and three orientation parameters (e.g., $\theta_x$, $\theta_y$, and $\theta_z$). A completely unconstrained link is said to have six degrees offreedom or DOF [G. N. Sandor and A. G. Erdman, Advanced Mechanism Design: Analysis and Synthesis. Prentice-Hall, Inc, 1984.]. When a link is connected to another with a joint, its motion is constrained (relative to the other link). The concept of degrees of freedom becomes more complex as the number of links increase, as in the case of lazy tongs (see FIG. 11.2, lazy tongs).

The previously mentioned linkages are composed of rigid links and joints. A rigid link is self-explanatory, but a rigid joint is not immobile; rather it is the result of movement between two separate rigid surfaces. This is in contrast to compliant links and joints, which provide mobility by deflection of flexible components [L. L. Howell, Compliant Mechanisms. New York: John Wiley and Sons, 2001].

As used herein, "spatial linkages," as compared with planar linkages, have mobility in three dimensions. Naturally, spatial mechanisms may contain any combination of rigid and compliant links and joints. It is through spatial mechanisms that complex three-dimensional motion may be achieved.

As used herein, a pantomesh has the following distinguishing characteristics as compared previous work discussed in the following section. First, all of the pantograph elements are connected to each other by spherical joints, which allow three rotational degrees of freedom and of which a ball-and-socket joint is a common example. This allows a varying angle between pantograph elements and greater shape changing during actuation. Secondly, the mobility of the entire pantomesh is calculated using individual pantograph loops, rather than other restrictive methods. Finally, the pantograph elements may contain straight or bent links, planar or skew endpoints, and normal or angled pivots. This creates a wide design space for many shapes and motions.

Previous work on pantomeshes has focused on two areas: constant-curvature bent-link pantomeshes and simple straight-link pantomeshes with isosceles trapezoidal elements:

| Description | Dimensions | # Links Min | # Links Max | Topology | Connecting Joint | Mobility Criterion |
|---|---|---|---|---|---|---|
| Kempe | Planar | | | bent-link | revolute | |
| Hoberman's doubly-curved | Compound Planar | 4 | ∞ | bent-link | gusset | Half-Angle |
| GAE | Planar | | | bent-link | gusset | Parallelogram |
| Wohlhart | Spatial | 4 | ∞ | bent-link | gusset | |
| General Pantomesh | Spatial | 4 | ∞ | any | spherical | multiple |

Those areas, their early planar forbears, and closely related linkages, are detailed below.

Conventional Planar Pantomeshes

One of the earliest examples of a planar pantomesh was developed by Kempe (A. B. Kempe, "On conjugate four-piece linkages," Proceedings of the London Mathematical Society, vol. s1-9, pp. 133-149, Nov. 1, 1877) as an examination of mobile eight-bar linkage. See FIG. 11.3, Kempe's eight-bar linkage. The pantograph elements, of which there are four here, are connected by pin joints. Another form of a planar pantomesh was developed by Hoberman.

Close relatives to planar pantomeshes are general constant-curvature pantomeshes. Much like a flat membrane stretched over a ball, these linkages maintain their basic shape during their motion; only a linear scaling is increased. Each of the pantograph elements are connected by a gusset joint, or two revolute joints whose axes intersect. Constant-curvature pantomeshes have constant angles between their constituent pantograph elements, and therefore do not require spherical joints between them as variable-curvature pantomeshes do.

The topology of these linkages is simple: each pantograph element is joined by a revolute joint in the center of each link. A bracket connects the revolute joints for the bases of each link pair and for the summits of each link pair, until the last link pair connects with the first. All points collapse to the same axis at the same rate, given the midpoint location of the pin joint in each pantograph element. At the same time, the height of the chair grows along this axis. For an example, see FIG. 11.4, a camp stool with a four link-pair collapsible mechanism.

These scissor-pair units have been stacked to create deployable antenna mechanisms [Z. You, "Deployable structures for masts and reflector antennas," 1994, G. R. Luckey, "Nesting three dimensional lazy tong structure," 1972. U.S. Pat. No. 3,672,104 (which is incorporated herein by reference)] as shown in FIG. 11.5, Deployable antenna mast. As with the camp stool, the deployable antenna uses a fixed-angle bracket to join pantograph elements at their base and summit. In FIG. 11.5, the fixed angle is 120° for a three-sided device, while the chair in FIG. 11.4 has 90° for a four-sided device. The antenna stacks units by joining the pin joints of the summit of one level to the base pin joints of the next level, similar to lazy tongs. As opposed to the chair design, the antenna is intended to collapse downward to a plane when not in use, rather than collapsing radially to an axis. FIG. 11.5A shows a deployable antenna mast. FIG. 11.5B shows a single module of the antenna mast. FIG. 11.5C shows a pantograph element contained a module of the mast. FIG. 11.5D is a top view of the antenna mast.

Other examples include the Mongolian yurt, a collapsible dwelling that has rounded wall made of an expandable lattice.

One special application of planar pantomeshes is the Hoberman Sphere [C. Hoberman, "Reversibly expandable doubly-curved truss structure," Jul. 24, 1990. U.S. Pat. No. 4,942,700 (which is incorporated herein by reference)] as shown in FIG. 11.6, collapsible toy based on Hoberman's expandable truss patent [C. Hoberman, "Hoberman designs, home page," 2006]. FIG. 11.6A shows the toy collapsed; FIG. 11B shows the toy expanded. This linkage has many links joined in radially-collapsing pantograph elements that are arranged so that they move toward a common point. See FIG. 11.7, radial collapsing of link pairs FIG. 11.7A shows the pantograph expanded; FIG. 11.7B shows the pantograph collapsed.) In fact, it consists of several planar great circle linkages that are connected at their intersections. This creates a three-dimensional shape with multiple planar pantomeshes. Although the overall linkage is spatial, the combination of planar pantomeshes makes this a compound pantomesh, which will not be discussed in further detail. All of the revolute joint axes remain orthogonal to the radial lines of symmetry going through the center point. Each pantograph element can be represented as two joined links that slide along prismatic joints (or sliders) at the ends, A, C, D, and E, as shown in FIG. 11.8, kinematic interpretations of Hoberman's angulated element. Each link is part of a prismatic-revolute-revolute-prismatic (PRRP) linkage, and the pantograph elements are joined at their respective coupler points. The angle α remains constant so that the symmetry lines $OP_1$ and $OP_2$ remain stationary throughout the movement of the linkage. FIG. 11.8A shows a pair of general PRRP linkages sharing a common coupler point B. FIG. 11.8E shows a single PRRP linkage and its coupler point.

This mechanism is has a single degree of freedom for collapsing and expanding. The notion of a retractable roof using straight-link pantograph elements was first discussed by Pinero [E. P. Pinero, "Materia-estructa-form a," Hogar y arquitectura, vol. 40, pp. 24-30, 1962]. Critically, Escrig discovered early uses of expandable element.systems for space structures [F. Escrig, "Expandable space structures," Space Structures, vol. 1, pp. 79-91, 1985]. Both of these designs use compound planar pantomeshes.

Variable-Curvature Pantomeshes

U.S. Pat. No. 3,124,387 to O. F. Maclaren, "Seating structures," 1964 (which is incorporated herein by reference) is a similar linkage to the basis camp stool, although the pantograph elements are not joined at their centers with angled supports (see FIG. 11.9A and FIG. 19B of the present application, which are from U.S. Pat. No. 3,124,387; wherein FIG. 11.9A of the present application shows a perspective view and FIG. 11.9B shows a rear view). This system is similar to this invention, where offset revolute axes create different rates of collapsing. The kinematics of this design are not explicitly expressed in the patent literature. In brief, the offset pin joint in the front and rear pantograph elements cause the top of the chair to collapse faster than the bottom. The side pantograph elements have the pin joint at the link midpoints, therefore allowing the front and back of the chair to collapse simultaneously. The primary advantage of the offset pin joint arrangement is that the base of the chair is not as wide as the top of the chair when deployed. This chair design is not in common use, probably because it is less stable than wider-base chairs.

Several umbrellas also appear to use offset-axis pantograph elements (T. Hermanson, "Umbrella canopy frame and staff construction," 1980. U.S. Pat. No. 4,193,415 (which is incorporated herein by reference), L. K. Selden, "Umbrella,"

1859. U.S. Pat. No. 23,503 (which is incorporated herein by reference)), although the exact nature of the link dimensions is not specified. The umbrella in FIG. 11.10, example of umbrella from U.S. Pat. No. 4,193,415 uses pantograph elements that have a pivot slightly closer to the top of the umbrella, thereby allowing the outer part to expand faster than the inner part when deployed. FIG. 11.10 shows an umbrella in an expanded state, and a second umbrella in a collapsed state. However, the patent specification and claims describe pivots at the link midpoints. Additionally, all joints are claimed to be pin joints, but the angle between link pairs varies during deployment.

Both the umbrella and angled-support chair have designs similar to that patented by Atake (Atake, "Framework structure," Jun. 9, 1998 1986. U.S. Pat. No. 5,761,871 (which is incorporated herein by reference)). Each pantograph element has a perimeter defined by an isosceles trapezoid. Because the relative angle of pantograph element planes changes during actuation, they must be connected by multiple revolute joints.

Bent-Link Pantograph Elements

A popular example of a collapsible mechanism is the expandable dome. See FIG. 11.11, expandable dome. FIG. 11.11 shows domes in varying degrees of expansion. Hoberman does make use of several linkages that qualify as bent-link pantomeshes, such as the expandable dome [C. Hoberman, "Radial expansion/retraction truss structures," Jun. 18, 1991. U.S. Pat. No. 5,024,031].

Scope

This description details single degree-of-freedom spatial linkages defined as pantomeshes. As used herein, "pantomeshes" are class of mechanisms that provide a meaningful radial force or define a shape in general and in one embodiment, a breast stabilization device for cancer-related interventions.

Degrees of Freedom

The number of degrees of freedom (DOF) of a mechanism can be calculated using the Gruebler-Kutzbach equation (Equation (1.1)) [M. Grübler, Getriebelehre: eine Theorie des Zwanglaufes und der ebenen Mechanismen. Berlin: Springer, 1917, K. Kutzbach, "Mechanische leitungsverzweigung, ihre gesetze und anwendungen," Maschinenbau, der Betrieb, vol. 8, pp. 710-716, 1929].

$$M = 6(N-1) - 5f_1 - 4f_2 - 3f_3 - 2f_4 - f_5 \quad (1.1)$$

where M is the mobility or number of degrees of freedom, N is the number of links, $f_1$ is the number of $f_1$ joints, or joints that allow one degree of freedom such as revolute or slider joints. $f_2$ joints allow two DOF, $f_3$ joints allow three DOF, and so on. Spherical joints are $j_3$ joints because they allow rotations in three orthogonal axes but restrict any translational motion.

By examining a basic n×m pantomesh, the number of links is 2 nm, the number of revolute ($f_1$) joints is nm, and the number of spherical joints is 2 m+3(n-1)m. Therefore, according to the Gruebler-Kutzbach equation:

$$M = 6(2nm - 1) - 5(nm) - 4(2m + 3(n-1)m) \quad (1.2)$$
$$= -5nm + 4m - 6$$

Therefore, according to Equation (1.2), a closed pantomesh is never mobile. In practice, this has been proven incorrect.

FURTHER DESCRIPTION: This description details pantograph elements and their assembly into closed chains. By properly assembling closed chains in two or more rows, a single degree of-freedom linkage is created. This description also details the mobility of closed pantograph element chains, including criteria for achieving many, one, or zero degrees of freedom based on geometry. This description further shows how to synthesize such linkages for various tasks. The complexity of a large, multiple-pantograph-element chain requires a significant manufacturing and assembly effort when rigid joints are used. Therefore, a multi-link compliant spherical joint is presented for use in a compliant version of a closed pantograph element chain. In some embodiments, this compliant linkage is manufactured with vacuum forming; in other embodiments, this compliant linage is manufactured with rapid prototyping; and in other embodiments, this compliant linage is manufactured with molding techniques. Finally, this description details the design of a new mechanism to provide circumferential stabilization pressure for the purpose of stabilizing the human breast during cancer-related interventions.

Planar Straight-Link Pantomeshes

This chapter describes the basic kinematics of pantomeshes and, in particular, the constituent elements of pantomeshes the pantograph element. As used herein, a "pantograph element" is a pair of two links joined by a central pivot joint. Assuming that each link is also joined to other pantograph elements at both endpoints, each is a tertiary link in conventional linkage theory.

First, the assembly of axisymmetric pantomeshes is detailed as an introduction to a basic closed mesh. Then a more general approach to assembly is briefly presented. As used herein, a "planar pantograph element" is one where the four endpoints of the links are coplanar; otherwise they are skew. A "planar straight-link pantograph element" is one where the pivot joint is on the line between the endpoints for both links. Planar pantograph elements with the pivot joint offset from the line between link endpoints is referred to as "bent-link pantograph elements."

The primary kinematic concern of the pantograph element is the relative motion of the link endpoints. This description begins by defining nomenclature and general kinematics of planar straight pantograph elements. Next, the mobility of assembled pantomeshes are examined. Then, the assembly of axisymmetric pantomeshes is detailed as an introduction to a basic closed mesh. Then a more general approach to assembly is briefly presented.

Kinematics of Pantograph Elements

A straight-link pantograph element is one where the pivot joint is on the line between the endpoints for both links. A diagram of such a pantograph element is shown in FIG. 12.1.

Within a connected pantomesh, a pantograph element in row A and column 1 is defined by four link endpoints: $P_{A1}$, $P_{A2}$, $P_{B1}$, and $P_{B2}$. Each point is defined by three variables in space: $P_i = (x_i; y_i; z_i)$. The length of one link is $L_{A1}$ and the other is $M_{A1}$, as shown. The distance from $P_{A1}$ to the center pivot is $e_{A1}$, and from the center pivot to $P_{B2}$ is $f_{A1}$. Similarly, the distance from $P_{A2}$ to the center pivot is $g_{A1}$, and from the center pivot to $P_{B1}$ is $h_{A1}$. In the case of straight-line pantograph elements, $L_{A1} = e_{A1} + f_{A1}$ and $M_{A1} = g_{A1} + h_{A1}$, as shown in FIG. 12.1.

Further, the exterior dimensions of the pantograph element perimeter, or bounding quadrilateral, are defined as $j_{A1}$, $k_{A1}$, $j_{B1}$, and $k_{A2}$ are the "south," "west," "north," and "east," respectively, as shown in FIG. 12.1. Many pantograph elements may be classified as to this bounding simple quadrilateral formed by the traced perimder throughout its range of motion.

Axisymmetric Pantomeshes
Nomenclature Closed Pantograph Element Chains

Pantograph elements may be joined together at their ends via spherical joints to form a closed chain, such as the single-row one in FIG. 12.3(a). Such closed chains may also be stacked in rows, such as the example in FIG. 12.3(b). Using a row-column nomenclature, as used herein, the example in FIG. 12.3(b) will be referred to as a 2×6 configuration: six pantograph elements in a column in a closed loop stacked in two rows that are open on their ends. The linkage in 12.3(a) is a 1×5 pantograph element chain. More complex arrangements will be discussed in later.

Rectangular and Parallelogram Pantograph Elements

A "rectangular pantograph element", as used herein, has two straight links that meet in their exact centers (i.e. $e_{A1}=f_{A1}=g_{A1}=h_{A1}$). As shown in FIG. 12.2(a). Most lazytongs devices use rectangular pantograph elements joined by revolute joints to create a large extension with little input. The basic camp stool [J. B. Fenby, "Camp stool," 1881. U.S. Pat. No. 244,215. O. F. Maclaren, "Seating structures," 1964. U.S. Pat. No. 3,124,387] and deployable antenna [Z. You, "Deployable structures for masts and reflector antennas," 1994] are examples of meshes with rectangular pantograph elements.

With $j_{B1}=j_{A1}$ and $k_{A2}=k_{A1}$, only the following kinematic equations for a rectangular pantograph elements are necessary:

$$k_{A1}^2 = L_{A1}^2 - j_{A1}^2 \qquad (2.1)$$

$$k_{A2} = k_{A1} \qquad (2.2)$$

$$j_{B1} = j_{A1} \qquad (2.3)$$

Another simple example is a parallelogram pantograph element (see FIG. 12.2(b)). As used herein, a "parallelogram pantograph element" has diagonals that always meet at their midpoints [E. W. Weisstein, CRC Concise Encyclopedia of Mathematics. CRC Press, 2002], and therefore $e_{A1}=f_{A1}$ and $g_{A1}=h_{A1}$ like the rectangular pantograph element. The parallelogram pantograph element also has opposing sides that are equal. The link lengths (quadrilateral diagonals) are different (i.e. $L_{A1} \neq M_{A1}$). Therefore, the relations of adjacent sides of a parallelogram pantograph element are shown in Equation (2.4).

$$k_{A1}^2 = \frac{L_{A1}^2}{2} + \frac{M_{A1}^2}{2} - j_{A1}^2 \qquad (2.4)$$

$$k_{A2} = k_{A1} \qquad (2.5)$$

$$j_{B1} = j_{A1} \qquad (2.6)$$

Rectangular Pantograph Element Chains
Isosceles Trapezoidal Pantograph Elements

If the pivot does not meet at the exact midpoint of the diagonals but at equal ratios (i.e. $e_{A1}=g_{A1}$ and $f_{A1}=h_{A1}$, but $e_{A1} \neq f_{A1}$), a straight-line isosceles trapezoidal pantograph element is formed. For convenience, these may also be referred to as symmetric straight-line pantograph elements, because each link is a mirror-image of the other. See FIG. 12.4. The pantograph element is defined by four link endpoints: $P_{A1}$, $P_{A2}$, $P_{B1}$, and $P_{B2}$.

The left and right sides of the bounding trapezoid ($k_{A1}$ and $k_{A2}$) are equal, and the top side ($j_{B1}$) is a simple function of the bottom side ($j_{A1}$), as shown in Equations. (2.7) and (2.8). Examples of symmetric straight-line pantomeshes are shown in FIG. 12.3.

$$k_{A2} = L_{A1}^2 - \left(\frac{f_{A1}}{e_{A1}}\right) j_{A1}^2 \qquad (2.7)$$

$$k_{A1} = k_{A2} \qquad (2.8)$$

The top side of the bounding quadrilateral may be found using similar triangles to obtain Equation (2.9).

$$j_{B1} = \left(\frac{f_{A1}}{e_{A1}}\right) j_{A1} \qquad (2.9)$$

Two Row Pantograph Element Chains

Isosceles trapezoidal pantograph elements are relatively easy to use in closed chains and provide interesting characteristics. The following is a thorough investigation of the assembly of a chain of isosceles trapezoidal pantograph elements, beginning with two pairs in an open scissor chain as shown in FIG. 12.5 to be extended to a two-row, six-column closed (2×6) chain.

To orient the linkage in space, the following constraints are specified.

$$x_{A1}=y_{A1}=z_{A1}=0 \qquad (2.10)$$

$$y_{A2}z_{A2}=0 \qquad (2.11)$$

$$z_{A3}=0 \qquad (2.12)$$

The distance between the bottom points, $j_{A1}$, may be selected as a free choice; the variable that determines the dimensions of each pantograph element in the chain. In this case, each pantograph element on a level is the same. With a 2×2 open scissor chain, the following unknowns remain: $x_{A3}$, $y_{A3}$ (coordinates of $P_{A3}$), $P_{B1}$, $P_{B2}$, and $P_{B3}$. The base distance, $j_{A1}$, is the same for each pantograph element in a level so $j_{Ai}=j_A$ for all i. Therefore, the standard distance equation can be used to relate $x_{A3}$ and $y_{A3}$ to known variables. The distance between points $P_i$ and $P_j$ will be represented as $\{P_i;P_j\}$.

$$(\{(\{P_{A2}, P_{A3}\})^2\})^2 = (x_{A3}-x_{A2})^2 + (y_{A3}-y_{A2})^2 + (z_{A3}-z_{A2})^2 \qquad (2.13)$$

$$(\{(\{P_{A2}, P_{A3}\})^2\})^2 = j_{A2}^2 = j_A^2 \qquad (2.14)$$

$$x_{A3}^2 + y_{A3}^2 = 2j_A x_{A3} \qquad (2.15)$$

Now $P_{B2}$ may be determined using three distance equations govern the position of this point:

$$(\{(\{P_{A1}, P_{B2}\})^2\})^2 = L_{A1}^2 = L_A^2 \qquad (2.16)$$

$$(\{(\{P_{A3}, P_{B2}\})^2\})^2 = L_{A2}^2 = L_A^2 \qquad (2.17)$$

$$(\{(\{P_{A2}, P_{B2}\})^2\})^2 = k_{A2}^2 = k_A^2 \qquad (2.18)$$

$$k_A^2 = L_B^2 - \lambda_B j_B^2 \qquad (2.19)$$

Combining Eqn. (2.16) and Eqn. (2.17):

$$(\{(\{P_{A1}, P_{B2}\})^2\})^2 = (\{(\{P_{A3}, P_{B2}\})^2\})^2 \qquad (2.20)$$

$$x_{B2}^2 - y_{B2}^2 + z_{B2}^2 = (x_{B2}-x_{A3})^2 + (y_{B2}-y_{A3})^2 + (z_{B2}-z_{A3})^2 \qquad (2.21)$$

$$2x_{A3}x_{B2} + 2y_{A3}y_{B2} = x_{A3}^2 + y_{A3}^2 \qquad (2.22)$$

Substituting Eqn. (2.15) for $x_{A3}^2+y_{A3}^2$ and rearranging:

$$y_{B2} = \left(\frac{x_{A3}}{y_{A3}}\right)(j_A - x_{B2}) \tag{2.23}$$

Equations (2.16) and (2.18) can be subtracted to obtain $$\{(x_{B2} - x_{A1}^0)^2 + (y_{B2} - y_{A1}^0)^2 + (z_{B2} - z_{A1}^0)^2 = L_{A1}^2\} \tag{2.24}$$

$$-\{(x_{B2} - x_{A2})^2 + (y_{B2} - y_{A2}^0)^2 + (z_{B2} - z_{A2}^0)^2 = k_{A1}^2 = L_{A1}^2 - \lambda_A j_{A1}^2\}$$

$$-2j_A x_{B2} - j_A^2 = \lambda_A j_A^2$$

$$x_{B2} = \frac{1}{2}(1 + \lambda_A)j_A$$

Substituting into Eqn. (2.23), $y_{B2}$ can be found:

$$y_{B2} = \left(\frac{x_{A3}}{y_{A3}}\right)\frac{1}{2}(1 + \lambda_A)j_A \tag{2.25}$$

Note: neither $x_{B2}$ nor $y_{B2}$ depend on the specific link lengths; only the relative position of the revolute joints and the position other variables.

Finally, $z_{B2}$ can be most easily found using Eqn. (2.16):

$$z_{B2}^2 = L_{A1}^2 - x_{B2}^2 - y_{B2}^2 \tag{2.26}$$

$$z_{B2}^2 = L_{A1}^2 - \frac{1}{4}(1+\lambda_A)^2 j_A^2 - \frac{1}{4}\left(\frac{x_{A3}}{y_{A3}}\right)^2(1+\lambda_A)j_A^2$$

$$z_{B2}^2 = L_{A1}^2 - \frac{1}{4}(1+\lambda_A)^2\left(1 + \left(\frac{x_{A3}}{y_{A3}}\right)^2\right) j_A^2$$

Synthesis of Pantograph Meshes

The method for synthesizing a pantograph mesh to satisfy desired specifications is described here.

Shape Synthesis

For a column-closed mesh with m rows and n columns, the total number of unknown variables is 4 mn for straight link pantographs and 6mn for bent link pantographs. This is easily calculated: each straight link has two variables, its length and the location of the revolute joint. For bent links, an extra variable is required to define an angle.

To synthesize a mesh based on constraints, basic geometric rules may be followed as shown in the table below. The link lengths and ratios are the desired output variables that remain the same throughout the motion of the mesh. To fit geometric constraints, position in space must also be considered—three coordinate variables for each pantograph endpoint. These points may be solved for different positions or shape configurations, the total number of shapes being s. A shape configuration is analogous to a precision point in standard kinematic synthesis [A. G. Erdman and G. N. Sandor, Mechanism Design: Analysis and Synthesis, vol. 1. Prentice-Hall, Inc, 1991, p. 491]

| Variables | Straight-Link Pantograph | Bent-Link Pantograph |
|---|---|---|
| Link Lengths & Ratios (L, M, λ, μ, etc.) | 4mn | 6mn |
| Pantograph End Points (x, y, z) | 3(m + 1)ns | 3(m + 1)ns |

To have a solvable system, the number of equations (see table below) must equal the number of variables. First, the link lengths and ratios are related to the pantograph endpoints using basic distance equations.

| Geometry Equations | | Constraint Equations | |
|---|---|---|---|
| Link Lengths & Ratios | 4mns | Fixed point | 3p |
| Pantograph Planarity | mns | Point-on-curve | 2p |
| Mobility | (m − 1)n? | Point-on-surface | p |

Next, the planarity of each pantograph must be established.

To synthesize a shape, several constraints may be placed on points, perhaps in different shape configurations. Point-on-curve constraints consist of two equations, while point-on-surface constraints consist of one equation. Points may also be fixed relative for a shape configuration.

One option for determining the best fit is to use the conjugate gradient search method. This algorithm is as follows:

1. Guess the values of $t_i$ for all 3n points that satisfy the geometric constraints.
2. Calculate the sources of error e, such as the pantograph gap, which should be zero if they are planar, and the difference from "perfect mobility" for each pantograph. Other errors may be added to coerce the solver to stay within certain boundaries, to avoid overlap, etc.
3. Simulate the gradient of the error relative to guesses.
4. Search along the negative gradient (steepest descent) for the lowest total error.
5. Calculate the error and its gradient.
6. Calculate the search direction based on the current and previous gradient.
7. Search along the search direction for the lowest total error.
8. Compare the error value to the lowest acceptable value and/or the lowest acceptable change in value. If the criteria have not been satisfied, go back to operation 5.

Example: One Position, Three Point-on-Curve Constraints

Given three curves in space, an articulating straight-line pantograph mesh may be synthesized so that the endpoints of each pantograph lie on those curves. Using the terms from the tables above, the number of equations and variables is matched exactly for this two-row, n-column mesh:

$$\text{Variables} \quad \text{Equations} \tag{8.1}$$

$$4mn + 3(m + 1)ns = 4mns + mns + (m − 1)n + 2(3n)$$

$$4(2)n + 3(2 + 1)n(1) = 4(2)n(1) + (2)n(1) + (2 − 1)n + 6n$$

$$8n + 9n = 8n + 2n + n + 6n$$

$$17n = 17n$$

The pantograph endpoints may be represented using a dummy variable, t, to follow point-on-curve constraints as shown in Equation (8.2).

$$x_A = p_A \cos t; \quad y_A = q_A \sin t; \quad z_A = 0 \tag{8.2}$$

$$x_B = p_B \cos t; \quad y_B = q_B \sin t; \quad z_B = z_B \quad (const)$$

$$x_C = p_C \cos t; \quad y_C = q_C \sin t; \quad z_C = z_C \quad (const)$$

These are the iteration variables for the solver. The link lengths are calculated with a basic distance formula:

$$L_{i,j}^2 = (x_{i+1,j+1} - x_{i,j})^2 + (y_{i+1,j+1} - y_{i,j})^2 + (z_{i+1,j+1} - z_{i,j})^2 \qquad (8.3)$$

$$M_{i,j}^2 = (x_{i,j+1} - x_{i+1,j})^2 + (y_{i,j+1} - y_{i+1,j})^2 + (z_{i,j+1} - z_{i+1,j})^2 \qquad (8.4)$$

The remainder of the variables are measured against their desired values. For the pantograph gap d, the desired value is zero for each pantograph to force planar pantographs. Those equations may be expanded to calculate the link ratios λ and μ. First, a new pantograph bottom distance $j_{trans}$ is calculated by transposing the vector $P_{A2}$ the distance d (which may not be zero for this set of t's) as shown in Equation (8.5). The subsequent equations calculate the link ratios A and μ using vector algebra.

$$\vec{j_{trans}} = \vec{P}_{A2} + d\hat{n} - \vec{P}_{A1} \qquad (8.5)$$

$$\left(\frac{f}{e}\right) = \frac{\|\vec{L} \times \vec{M}\|}{(\vec{j_{trans}} \times \vec{M}) \cdot (\vec{L} \times \vec{M}) - 1} \qquad (8.6)$$

$$\left(\frac{h}{g}\right) = \frac{\|\vec{M} \times \vec{L}\|}{(-\vec{j_{trans}} \times \vec{L}) \cdot (\vec{M} \times \vec{L}) - 1} \qquad (8.7)$$

After the link ratios are calculated, the mobility error is calculated using the mobility criteria from Eqn. (2.99), rearranged to obtain zero error for a mobile linkage:

$$e = \left(\frac{f_{B1}}{e_{B1}}\right)\left(\frac{h_{A1}}{g_{A1}}\right) - \left(\frac{h_{B2}}{g_{B2}}\right)\left(\frac{f_{A2}}{e_{A2}}\right). \qquad (8.8)$$

The total error, represented by the 2-norm of the error vector, then becomes the factor to be minimized in the optimization algorithm. Successive iterations involve minimizing the error by altering values for the t's representing pantograph endpoints on each curve. See FIG. 13.1, a solution for a two-row, six-column straight-line pantograph mesh.

Example: Three Rows, One Position

A more complex example of straight-line pantograph synthesis is a one position, three rows, and n columns specification. Once three rows of endpoints are given point-on-line constraints, only n equations are required to specify the problem. Therefore, the remaining row of endpoints can allow a point-on-surface constraint. One method for defining a surface is a NURBS (non-uniform rational B-spline) surface [Piegl and W. Tiller, The NURBS book, Berlin: Springer-Verlag, 1995].

$$x_A = p_A \cos t; \ y_A = q_A \sin t; \ z_A = 0 \qquad (8.9)$$

$$x_B = p_B \cos t; \ y_B = q_B \sin t; \ z_B = z_B(const) \qquad (8.10)$$

$$x_D = p_D \cos t; \ y_D = q_D \sin t; \ z_D = z_D(const) \qquad (8.11)$$

$$x_C = \sum_{i=1,j=1}^{m,n} (x_{patch(i,j)} B_i(u) B_j(v)) \qquad (8.12)$$

$$y_C = \sum_{i=1,j=1}^{m,n} (y_{patch(i,j)} B_i(u) B_j(v)) \qquad (8.13)$$

$$z_C = \sum_{i=1,j=1}^{m,n} (z_{patch(i,j)} B_i(u) B_j(v)) \qquad (8.14)$$

The Berstein polynomial functions B(u) are used to weight the control points ($x_{patch(i,j)}$; $y_{patch(i,j)}$; $z_{patch(i,j)}$) appropriately for that position on the patch.

With the addition of variables, more processing time is required, but the result is similar.

Example: Three Rows, Two Positions

A NURBS patch is used to define each of the k positions:

$$\{x_C\}_k = \sum_{i=1}^{m}\sum_{j=1}^{n} (x_{patch(i,j,k)} \{B_i(u)\}_k \{B_j(v)\}_k) \qquad (8.15)$$

$$\{y_C\}_k = \sum_{i=1}^{m}\sum_{j=1}^{n} (y_{patch(i,j,k)} \{B_i(u)\}_k \{B_j(v)\}_k) \qquad (8.16)$$

$$\{z_C\}_k = \sum_{i=1}^{m}\sum_{j=1}^{n} (z_{patch(i,j,k)} \{B_i(u)\}_k \{B_j(v)\}_k) \qquad (8.17)$$

Rather than defining additional curves, the point-on-curve constraints may be defined by adding additional constraints, such as v=const. The following specifications are given to solve.

By specifying more than one desired shape, many more constraint equations are introduced. Therefore, bent-link pantographs are synthesized; adding two more variables for each pantograph. In fact, bent-link pantographs cannot be synthesized with a single shape specification only. When given only a single set of end-points only the intersection of $\vec{L}$ and $\vec{M}$ may be found.

See FIG. 13.2A, which shows a solution for two specified shapes in the first position, wider and shorter. See FIG. 13.2B, which shows a solution for two specified shapes in the second position, thinner and taller.

Example: Two Position, Symmetry Constraints

Another approach for pantograph mesh synthesis is to use symmetry constraints. The approach in the table below is to use an open m×n pantograph mesh with a symmetry plane. That symmetry plane will require point-on-line constraints for points on the symmetry plane.

| | Variables |
|---|---|
| Link Lengths & Ratios | 6mn |
| Pantograph End Points | 3(m + 1)(n + 1)s = 6mn + 6m + 6n + 6 |
| TOTAL | 12mn + 6m + 6n + 6 |
| | Equations |
| Link Lengths & Ratios | 4mns = 8mn |
| Pantograph Gap | mns = 2mn |
| Mobility | (m − 1)(n − 1) = mn − m − n + 1 |
| Point-on-point (3p) | 24 |
| Point-on-line (2p) | 2(2(n − 1) + 2(m − 1)) = 4m + 4n − 8 |
| Point-on-surface (p) | 2((m − 1)(n − 1)) = 2mn − 2m − 2n + 2 |
| TOTAL | 13mn + m + n + 19 |

In some embodiments, the appropriate number of rows and columns for a mobile pantograph mesh is found by setting the number of variables equal to the number of equations, so mn−5m−5n+13=0. The whole numbers that can match this ratio is: m=1; n=2.

Collapsibility $j_{A1,MIN}$, $j_{A1,MAX}$, $k_{A1,MAX}$, $k_{A1,MIN}$ which is calculated from the assembly. There will be two $j_{B1,MIN}$'s for a two-row mesh. They will have corresponding $k_{MAX}$'s Maybe go column-by-column, continuing to revise the $j_{MIN,MAX}$ as each pantograph is encountered.

Planar Instant Centers

An instant center is the point in space where the relative velocity between two links is zero [G. N. Sandor and A. G. Erdman, Advanced Mechanism Design: Analysis and Synthesis. Prentice-Hall, Inc, 1984]. The examination of instant centers of the links of a pantograph element can aid in the synthesis of certain scissor chains, as shown in FIG. 13.3. The lower left point, $P_{A1}$, is arbitrarily constrained to rotate about a fixed point. The lower right point, $P_{A2}$, is arbitrarily constrained to move horizontally to make a single degree-of-freedom, four-bar system. These links are labeled 1 through 4 as shown. The instant centers are shown as parenthetical pairs, i.e. (1,2) is the point where the relative velocity between link 1 (which is the fixed ground link) and link 2 is zero. Therefore, (1,2) coincides $P_{A1}$. Because the slider block moves along a straight line, the instant center (1,4) is located at infinity at either the top or bottom of the image. (2,3) coincides with the pin joint connecting links 2 and 3. In addition, (3,4) coincides with the pin joint connecting links 3 and 4. The location of other instant centers may be of use during synthesis.

The instant center between two links may also be found using the other instant centers using Kennedy's theorem [8, 27], which states that three instant centers shared by three rigid bodies in relative planar motion to another all lie on the same straight line. For instance, the instant center (1,3) is located on the line that goes through (1,4) and (3,4), or, in shorthand, $\overline{(1,4)\text{-}(3,4)}$ as shown in FIG. 8.3. (1,3) will also lie on $\overline{(1,2)\text{-}(2,3)}$. Similarly, (2,4) is located at the intersection of $\overline{(1,2)\text{-}(1,4)}$ and $\overline{(2,3)\text{-}(3,4)}$.

Proof: A Rectangular Pantograph Element Must be Straight-Line

Instant centers may be used to prove certain properties of pantograph elements to aid in synthesis of useful linkages. For instance, a rectangular pantograph element must consist of straight-line links; offset links will not result in a rectangular bounding perimeter throughout the range of motion. The proof is as follows:

First, place points $P_{A1}$, $P_{A2}$, $P_{B1}$, and $P_{B2}$ at four corners of an arbitrary rectangle. The locations of (1,2), (1,4), and (3,4) are known ($P_{A1}$, $\pm\infty\mathbf{1}$, $P_{A2}$). The locations of (2,4) and (1,3) are restricted to the vertical lines through (1,2) and (3,4), respectively (see FIG. 13.5(a)). Next, note that $P_{B1}$ must travel vertically with respect to link 1 (i.e. ground), and therefore (1,3) must be located on a horizontal line through $P_{B1}$. Therefore, (1,3) will coincide with $P_{B2}$. Similarly, (2,4) must coincide with $P_B\mathbf{1}$. The location of (2,3) must be at the intersection of (2,4)-(3,4) and (1,2)-(1,3), which are also the diagonals of the bounding rectangle. Therefore, the pivot (2,3) must be located at the intersection of the diagonals, thereby creating two straight-line links in the pantograph element.

Proof: A Right-Angle Trapezoidal Pantograph Element is not Possible

When attempting to achieve certain shapes in pantograph elements, it is useful to determine their feasibility without resorting to excessive equation manipulation. In some embodiments of this invention, a right-angled trapezoidal pantograph element might be useful in some instances, such as the building-like structure in FIG. 13.4. A right-angled trapezoid has one side that is perpendicular to the two parallel sides but not parallel to its opposite. The structure in FIG. 13.4 has right-angled trapezoidal pantograph elements in its upper corners. If the quadrilaterals were replaced with pantograph elements, would the resulting chain of pantograph elements be collapsible?

As in the previous example, place points $P_{A1}$, $P_{A2}$, $P_{B1}$, and $P_{B2}$ at four corners of an arbitrary right-angle trapezoid. The locations of (1,2), (1,4), and (3,4) are known, and (2,4) and (1,3) are restricted as always. As with the rectangular example, $P_{B1}$ must travel vertically with respect to link 1, and therefore (1,3) must be located on a horizontal line through $P_{B1}$. $P_{B2}$ must travel vertically with respect to link 4, and therefore (2,4) must coincide with $P_{B1}$. As with the rectangular example, the location of (2,3) must be at the intersection of (2,4)-(3,4) and (1,2)-(1,3).

To maintain a trapezoidal shape, the point $P_{B2}$ must rise vertically at the same rate at (1,3). The speed of $P_{B2}$ is less than (1,3) if it is toward the left as shown in FIG. 13.5(b). In addition, the velocity vector of $P_{B2}$ is more horizontal than the velocity of (1,3). The opposite is true if $P_{B2}$ is to the right of (1,3). It is impossible for the vertical velocities of these points to be equal unless it $P_{B2}$ and (1,3) coincide, thereby forming a rectangular pantograph element. Therefore, a right-angled trapezoidal pantograph element is not possible.

Example: A Symmetric, Fixed-Angle Pantograph Element

The initial position is specified as in FIG. 13.6. As in the general case, (1,3) and (2,4) must be located along the vertical lines that go through $P_{A2}$ and $P_{A1}$, respectively (see FIG. 13.6(a)). To fix the angle between the bounding sides, the velocities of $P_{B1}$ and $P_{B2}$ must be at that fixed angle relative to each other. On the right side, (1,3) must be along a line going through PB1 and perpendicular to a line connecting $P_{A1}$ and $P_{B1}$. Therefore, (1,3) is at the intersection between this line and the vertical line running through $P_{A2}$ (see FIG. 13.6(b)). Similarly, (2,4) must be at the intersection between the vertical line through $P_{A1}$ and a line going through $P_{B2}$ and perpendicular to a line connecting $P_{A2}$ and $P_{B2}$. From there, the location of (2,3) is simply the intersection of a line going through (1,2) and (1,3) and a line going through (3,4) and (2,4) (see FIG. 13.6(c)). In the symmetric case, this point is known to be equidistant from $P_{A1}$ and $P_{A2}$. Therefore, the Hoberman element solution [C. Hoberman, "Radial expansion/retraction truss structures," Jun. 18, 1991. U.S. Pat. No. 5,024,031, C. Hoberman, "Reversibly expandable doubly-curved truss structure," Jul. 24, 1990. U.S. Pat. No. 4,942, 700] has been obtained as shown in FIG. 13.6(d).

Opposite-Side Intersections

An opposite-side intersection is the point where opposing sides of the bounding quadrilateral intersect, assuming those bounding line segments are extended until they intersect (see FIG. 13.7). Opposite-side intersections play an important factor in the closing of pantograph element chains.

This point, $K_A$, is the same for each identical pantograph element that are connected at those sides. That is, $K_{A1}$ and $K_{A2}$ coincide, as do $K_{B1}$ and $K_{B2}$. The location of these two points, succinctly referred to as $\vec{K}_A = K[A_x], K[A_y], K[A_z])$ and $\vec{K}_B = (K[B_x], K[B_y], K[B_z])$. Using vector algebra to find this intersection point:

$$\vec{K}_A = \vec{P}_{A1} + (\vec{P}_{B1} - \vec{P}_{A1})t \qquad (8.18)$$

$$\vec{K}_A = \vec{P}_{A2} + (\vec{P}_{B2} - \vec{P}_{A2})s \qquad (8.19)$$

where t and s are dummy variables that extend the lines $P_{A1}P_{B1}$ and $P_{A2}P_{B2}$ to meet at $K_A$. The vectors may be taken in their component form because they are simply multiplied by scalars. Setting Equation (8.18) equal to Equation (8.19) for the z-components, $$-z_{A1}^0 + (z_{B1} - z_{A1}^0)t = -z_{A1}^0 + (z_{B2} - z_{A1}^0)s \qquad (8.20)$$

$$t = \left(\frac{z_{B2}}{z_{B1}}\right)s$$

$$t = s$$

Knowing that t=s, equations (8.18) and (8.19) can be combined to solve for $K_{Ax}$ using the x-components:

$$t = \frac{\mathcal{K}_{Ax} - x_{A1}}{x_{B1} - x_{A1}} = \frac{\mathcal{K}_{Ax} - x_{A2}}{x_{B2} - x_{A2}} \qquad (8.21)$$

$$(x_{B2} - x_{A2})\mathcal{K}_{Ax} = x_{B1}(\mathcal{K}_{Ax} - x_{A2})$$

$$\mathcal{K}_{Ax} = \frac{x_{A2} x_{B1}}{x_{A2} + x_{B1} - x_{B2}}$$

$$\mathcal{K}_{Ax} = \frac{\frac{1}{2}(1 - \lambda_A)x_{A2}^2}{(1 - \lambda_A)x_{A2}}$$

$$\mathcal{K}_{Ax} = \frac{1}{2}x_{A2}$$

Therefore, the variable t may be solved for:

$$t = \frac{\mathcal{K}_{Ax} - x_{A1}}{x_{B1} - x_{A1}} \qquad (8.22)$$

$$= \frac{\frac{1}{2}x_{A2}}{\frac{1}{2}(1 - \lambda_A)x_{A2}}$$

$$= \frac{1}{1 - \lambda_A}$$

Note that t does not depend on $x_{A2}$ and that if $\lambda=1$ then t is at infinity. The practical result is a rectangular pantograph element.

The remaining coordinates can now be found.

$$\mathcal{K}_{Ay} = -y_{A1}^0 + (y_{B1} - y_{A1}^0)t \qquad (8.23)$$

$$= \frac{\frac{1}{2}\left(\frac{x_{A3}}{y_{A3}}\right)(1 - \lambda_A)x_{A2}}{1 - \lambda_A}$$

$$= \frac{1}{2}\left(\frac{x_{A3}}{y_{A3}}\right)x_{A2}$$

Note that $k_{Ay}$ also does not depend on $\lambda_A$.

$$\mathcal{K}_{Az} = -z_{A1}^0 + (z_{B1} - z_{A1}^0)t \qquad (8.24)$$

$$= \frac{z_{B1}}{(1 - \lambda_A)}$$

In a similar fashion, we can find $K_B$. Logically, $t_B = s_B$.

$$t_B = \frac{\mathcal{K}_{Bx} - x_{B1}}{x_{C1} - x_{B1}} = \frac{\mathcal{K}_{Bx} - x_{B2}}{x_{C2} - x_{B2}} \qquad (8.25)$$

$$\mathcal{K}_{Bx} = \frac{x_{B1}(x_{C2} - x_{B2}) - x_{B2}(x_{C1} - x_{B1})}{x_{C2} - x_{C1} - (x_{B2} - x_{B1})}$$

$$\mathcal{K}_{Bx} = \frac{\frac{1}{2}(1 - \lambda_A)x_{A2}\left(\frac{1}{2}(\lambda_A\lambda_B - \lambda_A)\right)x_{A2} - \frac{1}{2}(1 + \lambda_A)x_{A2}\left(\frac{1}{2}(\lambda_A - \lambda_A\lambda_B)\right)x_{A2}}{\lambda_A\lambda_B x_{A2} - \lambda_A x_{A2}}$$

$$\mathcal{K}_{Bx} = \frac{(1 - \lambda_A)(\lambda_B - 1)\lambda_A + (1 + \lambda_A)(\lambda_B - 1)\lambda_A}{4(\lambda_B - 1)\lambda_A} x_{A2}$$

$$\mathcal{K}_{Bx} = \frac{1}{2}x_{A2}$$

$$\mathcal{K}_{Bx} = \mathcal{K}_{Ax} \qquad (8.26)$$

The other coordinates of the pivot focus may be found in a similar manner:

$$\mathcal{K}_{By} = y_{B1} + (y_{C1} - y_{B1})t_B \qquad (8.27)$$

$$= \frac{1}{2}\left(\frac{x_{A3}}{y_{A3}}\right)(1 - \lambda_A)x_{A2} + \frac{y_{C1} - \frac{1}{2}\left(\frac{x_{A3}}{y_{A3}}\right)(1 - \lambda_A)x_{A2}}{1 - \lambda_A}$$

In some embodiments, the present invention provides a method for fabricating a pantomesh. This method includes providing a plurality of pairs of links, wherein each link has a first end and a second end, wherein each pair of links includes a first link and a second link, and wherein the plurality of pairs of links includes a first pair and a second pair; providing a plurality of revolute joints, including a first revolute joint and a second revolute joint; providing a plurality of spherical joints including a first spherical joint and a second spherical joint; connecting a location between the first end and the second end of the first link of the first pair to a location between the first end and the second end of the second link of the first pair using the first revolute joint; connecting a location between the first end and the second end of the first link of the second pair to a location between the first end and the second end of the second link of the second pair using the second revolute joint; connecting the first end of the first link of the first pair of links to the first end of the second link of the second pair of links using the first spherical joint; and connecting the second end of the second link of the first pair of links to the second end of the first link of the second pair of links using the second spherical joint, wherein a first line that extends through the first spherical joint and the third spherical joint of the first pantomesh element forms a first variable angle with a second line that extends through the second spherical joint and the fourth spherical joint of the first pantomesh element, and wherein the first variable angle changes as a distance between the first and third spherical joints increases, and wherein the first pantomesh element is not an isosceles trapezoid such that: if a line that extends through the first spherical joint and the second spherical joint of the first pantomesh element is parallel to a line that extends through the third spherical joint and the fourth spherical joint of the first pantomesh element, then a distance between the first spherical joint and the third spherical joint of the first pantomesh element is different than a distance between the second spherical joint and the fourth spherical joint of the first pantomesh element.

In some embodiments of this fabrication method, the providing of the plurality of pairs of links further includes providing a third pair and a fourth pair; the providing the plurality of revolute joints further includes providing a third revolute joint and a fourth revolute joint; the providing of the plurality of spherical joints further includes providing a third spherical joint, a fourth spherical joint and a fifth spherical joint; and the method further includes connecting a location between the first end and the second end of the first link of the third pair to a location between the first end and the second end of the second link of the third pair using the third revolute joint; connecting a location between the first end and the second end of the first link of the fourth pair to a location between the first end and the second end of the second link of the fourth pair using the fourth revolute joint; connecting the first end of the second link of the third pair of links to the first end of the first link of the fourth pair of links, using the second spherical joint; connecting the second end of the second link of the first pair of links to the first end of the first link of the third pair of links using the third spherical joint, connecting the first end of the second link of the fourth pair of links to the second end of the first link of the second pair of links using the fourth spherical join, and connecting the second end of the first link of the third pair of spherical joints to the second end of the second link of the fourth pair of spherical joints using the fifth spherical joint.

In some embodiments of this fabrication method, the providing of the plurality of pairs of links further includes providing a fifth pair and a sixth pair; the providing of the plurality of revolute joints further includes providing a fifth revolute joint and a sixth revolute joint; the providing of the plurality of spherical joints further includes a fifth spherical joint, a sixth spherical joint, a seventh spherical joint, and an eighth spherical joint; and the method further includes: connecting a location between the first end and the second end of the first link of the fifth pair to a location between the first end and the second end of the second link of the fifth pair using the fifth revolute joint; connecting a location between the first end and the second end of the first link of the sixth pair to a location between the first end and the second end of the second link of the sixth pair using the sixth revolute joint; connecting the first end of the second link of the second pair of links to the first end of the first link of the fifth pair of links using the fifth spherical joint; connecting the second end of the first link of the second pair of links to the second end of the second link of the fifth pair of links using the sixth spherical joint; connecting the first end of the second link of the fifth pair of links to the first end of the first link of the sixth pair of links using the seventh spherical joint; and connecting the second end of the first link of the fifth pair of joints to the second end of the second link of the sixth pair of joints using the eighth spherical joint.

In some embodiments of this fabrication method, the providing of the plurality of pairs of links further includes providing a third pair, fourth pair, a fifth pair, a sixth pair, a seventh pair and an eighth pair; the providing of the plurality of revolute joints further includes providing a fifth revolute joint, a sixth revolute joint, a seventh revolute joint and an eighth revolute joint; the providing of the plurality of spherical joints further includes a fifth spherical joint, a sixth spherical joint, a seventh spherical joint, and an eighth spherical joint; and the method further includes: connecting a location between the first end and the second end of the first link of the fifth pair to a location between the first end and the second end of the second link of the fifth pair using the fifth revolute joint; connecting a location between the first end and the second end of the first link of the sixth pair to a location between the first end and the second end of the second link of the sixth pair using the sixth revolute joint; connecting the first end of the second link of the second pair of links to the first end of the first link of the fifth pair of links using the fifth spherical joint; connecting the second end of the first link of the second pair of links to the second end of the second link of the fifth pair of links using the sixth spherical joint; connecting the first end of the second link of the fifth pair of links to the first end of the first link of the sixth pair of links using the seventh spherical joint; and connecting the second end of the first link of the fifth pair of joints to the second end of the second link of the sixth pair of joints using the eighth spherical joint.

In some embodiments of this fabrication method, the providing of the plurality of spherical joints further includes a ninth spherical joint and a tenth spherical joint; and the method further includes: connecting the first end of the first link of the first pair of links to the first end of the second link of the sixth pair of links using the ninth spherical joint; connecting the second end of the second link of the first pair of links to the second end of the first link of the sixth pair of links using the tenth spherical joint; constructing the links from a magnetic-resonance imaging (MRI) safe material, (in some such embodiments, a material such as nitinol or the like); and manipulating the apparatus to compress and steady biological tissue, such as a human breast, to facilitate a medical procedure, such a biopsy, during an MRI.

In some embodiments, the present invention provides a second method for fabricating a pantomesh, the second method including: providing a plurality of pairs of links, wherein each link has a first end and a second end, wherein each pair of links includes a first link and a second link, and wherein the plurality of pairs of links includes a first pair and a second pair; providing a plurality of revolute joints, including a first revolute joint and a second revolute joint; providing a plurality of spherical joints, including a first spherical joint and a second spherical joint; connecting the ends of at least two links to one another using spherical joints; connecting pairs of links using revolute joints wherein the revolute joints and links are configured (that is, locations of the revolute joints relative to ends of the links, angles of the revolute joints relative to the links that the revolute joints connect, and a distance between links at each revolute joint (the revolute joints' heights)) to restrict the pantomesh links to moving in a fixed manner relative to each other.

In some embodiments, the present invention provides a third method for fabricating a pantomesh, the third method including: providing a plurality of pairs of links, wherein each link has a first end and a second end, wherein each pair of links includes a first link and a second link, and wherein the plurality of pairs of links includes a first pair and a second pair; providing a plurality of revolute joints, including a first revolute joint and a second revolute joint; providing a plurality of spherical joints, including a first spherical joint and a second spherical joint; connecting the ends of at least two links to one another using spherical joints; connecting pairs of links using revolute joints wherein the revolute joints and links are configured (that is, locations of the revolute joints relative to ends of the links, angles of the revolute joints relative to the links that the revolute joints connect, and a distance between links at each revolute joint (the revolute joints' heights)) to restrict the pantomesh links to moving in a fixed manner relative to each other.

In some embodiments, the present invention provides a computer-readable medium having instructions stored thereon for causing a suitably programmed information processor to execute a designing method that comprises: (a) determining an error set that includes at least one error, wherein the error-set value indicates at least one of an error in a distance between two links of at least one of the pantomesh elements, a mobility error of the pantomesh, a bent-link bend angle, and a link-length error; (b) receiving a solution set of a plurality of variables describing a pantomesh; (c) computing a new value of the error set at the solution set; (d) comparing at least one of (i) the new value of the error set relative to an acceptable value of the error set and (ii) a change in the new value of the error set relative to an acceptable amount of change in value of the error set; and (e) if one or more criteria of the compare have been met, outputting the solution set, (f) else: calculating a gradient of the error set at the solution set, calculating a new search direction based on a current and a previous gradient, and searching in the calculated new search direction to determine a new solution set having a new lowest total error along the new search direction and iteratively going (e.g., branching or the like) to (c).

In some embodiments, the computer-readable medium further includes instructions to cause the designing method to include controlling a computer numerically controlled (CNC) machine to fabricate elements of for the pantomesh.

In some embodiments, the computer-readable medium further includes instructions to cause the method to include inputting data based on the outputted solution set to a fabrication system that fabricates parts used in making the pantomesh.

In some embodiments, the computer-readable medium further includes instructions to cause the method to be executed on a computer at a location remote from a user, and to be controlled by the user across the interne. For example, in some such embodiments, the method is executed to provide an internet-based design service that facilitates design and/or fabrication of a pantomesh that meets a user's desires or requirements.

In some embodiments, the present invention provides an apparatus that includes a pantomesh that has a first plurality of pantomesh elements including a first pantomesh element, a second pantomesh element and an Nth pantomesh element, where N is an integer larger than 2, and wherein each one of the first plurality of pantomesh elements includes: a pair of links including a first link and a second link, wherein each link of the pair of links has a first end and a second end; a revolute joint wherein the revolute joint connects a location between the first end and the second end of the first link to a location between the first end and the second end of the second link; and a plurality of spherical joints that includes a first spherical joint, a second spherical joint, a third spherical joint, and a fourth spherical joint, wherein the first spherical joint is attached to the first end of the first link, the second spherical joint is attached to the second end of the first link, the third spherical joint is attached to the first end of the second link, and the fourth spherical joint is attached to the second end of the second link; wherein the first and third spherical joints of the first pantomesh element connect to the second and fourth spherical joints, respectively, of the second pantomesh element of a first row of the first plurality of pantomesh elements, and the second and fourth spherical joints of the first pantomesh element connect to the first and third spherical joints, respectively, of the Nth pantomesh element of the first row; and wherein a first line that extends through the first spherical joint and the third spherical joint of the first pantomesh element forms a first variable angle with a second line that extends through the second spherical joint and the fourth spherical joint of the first pantomesh element, and wherein the first variable angle changes as a distance between the first and third spherical joints increases, and wherein the first pantomesh element is not an isosceles trapezoid such that: if a line that extends through the first spherical joint and the second spherical joint of the first pantomesh element is parallel to a line that extends through the third spherical joint and the fourth spherical joint of the first pantomesh element, then a distance between the first spherical joint and the third spherical joint of the first pantomesh element is different than a distance between the second spherical joint and the fourth spherical joint of the first pantomesh element.

In some embodiments of the apparatus, the first and third spherical joints of the second pantomesh element are successively connected through one or more other pantomesh elements of the first row until the first and third spherical joints of an N–1$^{st}$ pantomesh element of the first row further connect to the second and fourth spherical joints, respectively, of the N$^{th}$ pantomesh element of the first row, forming a closed pantomesh row or circular chain. In other embodiments, the first and third spherical joints of the second pantomesh element are successively connected through one or more other pantomesh elements of the first row until the first and second spherical joints of an N–1$^{st}$ pantomesh element of the first row further connect to the third and fourth spherical joints, respectively, of the N$^{th}$ pantomesh element of the first row, forming a closed helically connected pantomesh row or helical chain.

In some embodiments of the apparatus, a plurality of pantomesh element rows, including the first row, a second row and an M$^{th}$ row, where M is an integer larger than 2, are further connected wherein the first and second spherical joints of the first pantomesh element of the first row connect to the third and fourth spherical joints, respectively, of the first pantomesh element of the second row, the first and second spherical joints of the second pantomesh element of the first row connect to the third and fourth spherical joints, respectively, of the second pantomesh element of the second row, and the first and second spherical joints of the N$^{th}$ pantomesh element of the first row connect to the third and fourth spherical joints, respectively, of the N$^{th}$ pantomesh element of the second row; and wherein the third and fourth spherical joints of the first pantomesh element of the first row connect to the first and second spherical joints, respectively, of the first pantomesh element of the M$^{th}$ row, the third and fourth spherical joints of the second pantomesh element of the first row connect to the first and second spherical joints, respectively, of the second pantomesh element of the M$^{th}$ row, and the third and fourth spherical joints of the N$^{th}$ pantomesh element of the first row connect to the first and second spherical joints, respectively, of the Nth pantomesh element of the M$^{th}$ row.

In some embodiments, the plurality of pantomesh rows are further connected wherein the first and third spherical joints of the second pantomesh element of the first row connect to the second and fourth spherical joints, respectively, of the N$^{th}$ pantomesh element of the first row, the first and third spherical joints of the second pantomesh element of the second row connect to the second and fourth spherical joints, respectively, of the N$^{th}$ pantomesh element of the second row, and the first and third spherical joints of the second pantomesh element of the M$^{th}$ row connect to the second and fourth spherical joints, respectively, of the Nth pantomesh element of the M$^{th}$ row.

In some embodiments of the apparatus, the angle formed by a first line drawn through the two spherical joints connecting a first pantomesh element to a second pantomesh element on the first side of the first pantomesh element, and a second line drawn through the two spherical joints connecting the first pantomesh element to a third pantomesh element of the opposite side of the first pantomesh element intersect at an angle that varies as the pantomesh is expanded or collapsed.

In some embodiments of the apparatus, the links, revolute joints and spherical joints comprising the pantomesh are constructed of a magnetic-resonance imaging (MRI)-safe material (e.g., nitinol or polymer or other compatible material); and the pantomesh is configured to be moved to constrict and steady biological tissue (such as a human breast) to facilitate an in vivo medical procedure (such as a breast biopsy) during an MRI procedure. Some such embodiments further include one or more MRI-compatible remotely controlled actuators each coupled to one of the plurality of links and configured to move its link to constrain and steady the biological tissue.

In some embodiments, the present invention provides an apparatus that includes a pantomesh that in turn includes: a plurality of pairs of links, each pair of links including a first link and a second link; a plurality of revolute joints, each one of the plurality of revolute joints used to connect the first link to the second link of a corresponding one of the plurality of pairs of links; and a plurality of spherical joints used to connect ends of at least two links to one another, wherein the revolute joints and links are configured (that is, locations of the revolute joints relative to ends of the links, angles of the revolute joints relative to the links that the revolute joints connect, and a distance between links at each revolute joint (the revolute joints' heights)) to restrict the pantomesh links to move in a fixed manner relative to each other.

In some embodiments, the present invention provides an apparatus that includes a pantomesh; an insertion tube providing access to a body cavity, such as a stomach or an abdominal cavity; an insertion device to push the pantomesh through the insertion tube into the body cavity; and one or more handles attached to the pantomesh allowing it to be positioned within the body cavity and expanded, providing a rigid framework of predetermined shape within the body cavity.

In some embodiments, the present invention provides an apparatus that includes a pantomesh that in turn includes: a plurality of pairs of links, wherein each link has a first end and a second end, wherein each pair of links includes a first link and a second link, and wherein the plurality of pairs of links includes a first pair and a second pair; a plurality of revolute joints, including a first revolute joint and a second revolute joint, wherein the first revolute joint connects a location between the first end and the second end of the first link of the first pair to a location between the first end and the second end of the second link of the first pair, and the second revolute joint connects a location between the first end and the second end of the first link of the second pair to a location between the first end and the second end of the second link of the second pair; a plurality of spherical joints that includes a first spherical joint and a second spherical joint, wherein the first spherical joint connects the first end of the first link of the first pair of links to the first end of the second link of the second pair of links, and the second spherical joint connects the second end of the second link of the first pair of links to the second end of the first link of the second pair of links. In some such embodiments, each of a plurality of the pantomesh elements is not an isosceles trapazoid.

In some embodiments of the apparatus, the plurality of pairs of links further includes a third pair and a fourth pair; wherein the plurality of revolute joints further includes a third revolute joint and a fourth revolute joint, wherein the third revolute joint connects a location between the first end and the second end of the first link of the third pair to a location between the first end and the second end of the second link of the third pair, and the fourth revolute joint connects a location between the first end and the second end of the first link of the fourth pair to a location between the first end and the second end of the second link of the fourth pair; and wherein the plurality of spherical joints further includes a third spherical joint, a fourth spherical joint and a fifth spherical joint wherein the second spherical joint also connects the first end of the first link of the third pair of links to the first end of the second link of the fourth pair of links, the third spherical joint connects the first end of the first link of the third pair of links to the second end of the second link of the first pair of links, the fourth spherical joint connects the first end of the second link of the fourth pair to the second end of the first link of the second pair, and the fifth spherical joint connects the second end of the first link of the third pair to the second end of the second link of the fourth pair.

In some embodiments of the apparatus, the plurality of pairs of links further includes a fifth pair and a sixth pair; wherein the plurality of revolute joints further includes a fifth revolute joint and a sixth revolute joint, wherein the fifth revolute joint connects a location between the first end and the second end of the first link of the fifth pair to a location between the first end and the second end of the second link of the fifth pair, and the sixth revolute joint connects a location between the first end and the second end of the first link of the sixth pair to a location between the first end and the second end of the second link of the sixth pair; wherein the plurality of spherical joints further includes a fifth spherical joint, a sixth spherical joint, a seventh spherical joint and an eighth spherical joint, wherein the fifth spherical joint connects the first end of the second link of the second pair of links to the first end of the first link of the fifth pair of links, the sixth spherical joint connects the second end of the first link of the second pair of links to the second end of the second link of the fifth pair of links, the seventh spherical joint connects the first end of the second link of the fifth pair of links to the first end of the first link of the sixth pair of links, and the eighth spherical joint connect the second end of the first link of the fifth pair of joints to the second end of the second link of the sixth pair of joints In some embodiments of the apparatus, the plurality of spherical joints further includes a ninth spherical joint and a tenth spherical joint, wherein the ninth spherical joint connects the first end of the first link of the first pair of links to the first end of the second link of the sixth pair of links, and the tenth spherical joint connects the second end of the second link of the first pair of links to the second end of the first link of the sixth pair of links; wherein the links are constructed of an MRI-safe material; and wherein the apparatus is manipulated to compress and steady biological tissue such as a human breast to facilitate a medical procedure such a biopsy during an MRI.

In some embodiments, the present invention provides a pantomesh that includes a plurality of pairs of links, each pair of links including a first link and a second link; a plurality of revolute joints, each one of the plurality of revolute joints used to connect the first link to the second link of a corresponding one of the plurality of pairs of links; and a plurality of spherical joints used to connect ends of at least two links to one another, wherein the revolute joints and links are configured (that is, locations of the revolute joints relative to ends of the links, angles of the revolute joints relative to the links that the revolute joints connect, and a distance between links at each revolute joint (the revolute joints' heights) to restrict the pantomesh links to move in a fixed manner relative to each other.

In some embodiments, the present invention provides an apparatus that includes a pantomesh; an insertion tube providing access to a body cavity, such as a stomach or an abdominal cavity; an insertion device to push the pantomesh through the insertion tube into the body cavity; and one or more handles attached to the pantomesh allowing it to be positioned within the body cavity and expanded, providing a rigid framework of predetermined shape within the body cavity.

In some embodiments, the plurality of pairs of links further includes a third pair and a fourth pair: a plurality of interconnected links that is configured such that its overall shape is alterable by moving the ends of selected links.

In some embodiments, the present invention provides an apparatus that has a plurality of links; a plurality of spherical joints connecting the ends of four links; and a plurality of revolute joints operably connecting between pairs of links where their locations relative to the links, their angles relative to the links, and the height of the joint (distance between the links) restrict the pantomesh elements to moving in a predetermined fixed manner relative to each other so that as the pantomesh is manipulated, it expands and collapses in a continuous predetermined manner (e.g., a series of shapes). The predetermined motion occurs if the links and joints are constructed such that they conform to the design equations described herein.

In some embodiments, the pantomesh is a closed pantomesh cradle constructed of one or more materials with minimal deformation and safe for use within a high-magnetic-field active magnetic-resonance imaging (MRI) device. In some such embodiments, the pantomesh forms a collapsible constraint mechanism, having a plurality of openings, that is opened to a relatively open configuration to allow positioning of a patient's breast tissue within the cradle, and then closed to firmly hold the breast tissue in a fixed orientation relative to other structures in the MRI device such that the plurality of openings allow multiple access paths to tissue in the constrained breast for medical procedures such as obtaining tissue for a biopsy or other medical interventions (e.g., placement of chemical and/or radiation material in a lesion, or removal of the lesion) while the patient is in the MRI device and being imaged. Unlike conventional devices that use bilateral compression of the breast tissue and have computer-controlled (e.g., robotic) mechanisms that are in a fixed orientation relative to the bilateral compression plates, the radially-moving breast-compression cradle of the present invention allows computer-controlled (e.g., robotic) mechanisms to be moved (e.g., rotated) to any one of a large number of positions and orientations around the breast-compression cradle and have access through any of a plurality of the openings in the breast-compression cradle, thus providing unprecedented access and flexibility for medical procedures on the patient while they are in the MRI device.

In some embodiments, the present invention provides an apparatus that includes a pantomesh; a plurality of actuators (e.g., electronically controlled piezo-electric and MRI-compatible manipulation devices) connected to pantomesh link ends that are configured to expand and contract the pantomesh; and a mounting device operably connected to the pantomesh and actuators providing a fixed platform to control the contraction of the pantomesh so that it can hold and position body tissue, such as a human breast, in a substantially fixed relative orientation for medical procedures.

In some embodiments, the apparatus includes a computer at a location remote from a user (e.g., a physician), wherein the apparatus includes a computer and one or more programmed routines that run on the computer and are controlled by the user across the internet.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An apparatus for stabilizing tissue during an in vivo magnetic-resonance-imaging (MRI) procedure, the apparatus comprising:

a pantomesh that includes:

a first plurality of pantomesh elements including a first pantomesh element, a second pantomesh element and an $N^{th}$ pantomesh element, where N is an integer larger than 2, and wherein each one of the first plurality of pantomesh elements includes:

a pair of links including a first link and a second link, wherein each link of the pair of links has a first end and a second end;

a revolute joint wherein the revolute joint connects a location between the first end and the second end of the first link to a location between the first end and the second end of the second link; and a plurality of spherical joints that includes a first spherical joint, a second spherical joint, a third spherical joint, and a fourth spherical joint, wherein the first spherical joint is attached to the first end of the first link, the second spherical joint is attached to the second end of the first link, the third spherical joint is attached to the first end of the second link, and the fourth spherical joint is attached to the second end of the second link;

wherein the first and fourth spherical joints of the first pantomesh element are the third and second spherical joints, respectively, of the second pantomesh element of a first row of the first plurality of pantomesh elements, and the third and second spherical joints of the first pantomesh element are the first and fourth spherical joints, respectively, of the $N^{th}$ pantomesh element of the first row, wherein a first line that extends through the first spherical joint and the fourth spherical joint of the first pantomesh element forms a first variable angle with a second line that extends through the second spherical joint and the third spherical joint of the first pantomesh element, and wherein the first variable angle changes as a distance between the first and third spherical joints increases, and wherein the first pantomesh element is configured such that:

a first ratio of the first pantomesh element is different than a second ratio of the first pantomesh element, wherein the first ratio is of a first distance to a second distance of the first pantomesh element, wherein the second ratio is of a third distance to a fourth distance of the first pantomesh element, wherein the first distance of the first pantomesh element is between the revolute joint and the first spherical joint of the first pantomesh element, wherein the second distance of the first pantomesh element is between the second spherical joint and the first spherical joint of the first pantomesh element, wherein the third distance of the first pantomesh element is between the revolute joint and the third spherical joint of the first pantomesh element, and wherein the fourth distance of the first pantomesh element is between the fourth spherical joint and the third spherical joint of the first pantomesh element, and if a third line that extends through the first spherical joint and the third spherical joint of the first pantomesh element is parallel to a fourth line that extends through the second spherical joint and the fourth spherical joint of the first pantomesh element, then a distance between the first spherical joint and the fourth spherical joint of the first pantomesh element is different than a distance between the second spherical joint and the third spherical joint of the first pantomesh element.

2. The apparatus of claim 1, wherein the first and fourth spherical joints of the second pantomesh element are successively connected through one or more other pantomesh elements of the first row until the first and fourth spherical joints of an N–1$^{st}$ pantomesh element of the first row are the third and second spherical joints, respectively, of the N$^{th}$ pantomesh element of the first row, forming a closed pantomesh row.

3. The apparatus of claim 1, wherein the first and fourth spherical joints of the second pantomesh element are successively connected through one or more other pantomesh elements of the first row until the first and third spherical joints of an N–1$^{st}$ pantomesh element of the first row are the fourth and second spherical joints, respectively, of the N$^{th}$ pantomesh element of the first row, forming a closed helically connected pantomesh row.

4. The apparatus of claim 1, wherein a plurality of pantomesh element rows, including the first row, a second row and an M$^{th}$ row, where M is an integer larger than 2, are further connected such that the first and third spherical joints of the first pantomesh element of the first row are the fourth and second spherical joints, respectively, of the first pantomesh element of the second row, the first and third spherical joints of the second pantomesh element of the first row are the fourth and second spherical joints, respectively, of the second pantomesh element of the second row, and the first and third spherical joints of the N$^{th}$ pantomesh element of the first row are the fourth and second spherical joints, respectively, of the N$^{th}$ pantomesh element of the second row; and wherein the fourth and second spherical joints of the first pantomesh element of the first row are the first and third spherical joints, respectively, of the first pantomesh element of the M$^{th}$ row, the fourth and second spherical joints of the second pantomesh element of the first row are the first and third spherical joints, respectively, of the second pantomesh element of the M$^{th}$ row, and the fourth and second spherical joints of the N$^{th}$ pantomesh element of the first row are the first and third spherical joints, respectively, of the N$^{th}$ pantomesh element of the M$^{th}$ row.

5. The apparatus of claim 4, wherein the plurality of pantomesh rows are further connected wherein the first and fourth spherical joints of the second pantomesh element of the first row are the third and second spherical joints, respectively, of the N$^{th}$ pantomesh element of the first row, the first and fourth spherical joints of the second pantomesh element of the second row are the third and second spherical joints, respectively, of the N$^{th}$ pantomesh element of the second row, and the first and fourth spherical joints of the second pantomesh element of the N$^{th}$ row are the third and second spherical joints, respectively, of the N$^{th}$ pantomesh element of the N$^{th}$ row.

6. The apparatus of claim 2, wherein the links, revolute joints and spherical joints of the pantomesh are constructed of a magnetic-resonance-imaging (MRI)-safe material; and wherein the pantomesh is configured to be moved to constrain and steady biological tissue to facilitate the in vivo MRI procedure.

7. The apparatus of claim 6, further comprising a plurality of MRI-compatible remotely controlled actuators each coupled to one of the plurality of links and configured to move its link to constrain and steady the biological tissue.

8. The apparatus of claim 1, wherein the first and fourth spherical joints of the second pantomesh element are successively connected through one or more other pantomesh elements of the first row until the first and fourth spherical joints of an N–1$^{st}$ pantomesh element of the first row are the third and second spherical joints, respectively, of the N$^{th}$ pantomesh element of the first row to form a closed pantomesh row, wherein the closed pantomesh row of the pantomesh is configured to be moved to constrain and steady biological tissue to facilitate the in vivo MRI procedure; and wherein the apparatus further comprises:

a plurality of MRI-compatible remotely controlled actuators each coupled to one of the plurality of links and configured to move its link to constrain and steady the biological tissue;

a computer configured to receive signals from one or more coils of an MRI machine and to calculate an image representation of the biological tissue; and a computer configured to calculate positions and orientations of the plurality of links during the MRI and to display indicia of the calculated positions and orientations of the plurality of links on a displayed MRI image of the biological tissue based on the image representation during a medical procedure performed in the one or more coils of the MRI machine.

9. The apparatus of claim 8, further comprising a remotely actuated medical-procedure probe, wherein the computer configured to calculate positions and orientations of the plurality of links is further configured to avoid interference of the probe with the plurality of links.

10. The apparatus of claim 8, further comprising the MRI machine, wherein MRI machine includes control logic to obtain, store and display MRI images, and wherein the control logic to obtain, store and display MRI images is interfaced to the computer configured to calculate positions and orientations of the plurality of links.

11. The apparatus of claim 1, wherein a plurality of pantomesh element rows, including the first row, a second row and an M$^{th}$ row, where M is an integer larger than 2, are further connected such that the first and third spherical joints of the first pantomesh element of the first row are the fourth and second spherical joints, respectively, of the first pantomesh element of the second row, the first and third spherical joints of the second pantomesh element of the first row are the fourth and second spherical joints, respectively, of the second pantomesh element of the second row, and the first and third spherical joints of the $N^{th}$ pantomesh element of the first row are the fourth and second spherical joints, respectively, of the $N^{th}$ pantomesh element of the second row.

12. The apparatus of claim 1, wherein a plurality of pantomesh element rows, including the first row and a second row, are further connected such that the first and third spherical joints of the first pantomesh element of the first row are the fourth and second spherical joints, respectively, of the first pantomesh element of the second row, the first and third spherical joints of the second pantomesh element of the first row are the fourth and second spherical joints, respectively, of the second pantomesh element of the second row.

13. An apparatus for stabilizing tissue during an in vivo magnetic-resonance-imaging (MRI) procedure, the apparatus comprising:
a pantomesh that includes:
a first plurality of pantomesh elements including a first pantomesh element, a second pantomesh element and an $N^{th}$ pantomesh element, where N is an integer larger than 2, and wherein each one of the first plurality of pantomesh elements includes:
a pair of links including a first link and a second link, wherein each link of the pair of links has a first end and a second end;
a revolute joint having a revolute joint axis, wherein the revolute joint connects a location between the first end and the second end of the first link to a location between the first end and the second end of the second link; and
a plurality of spherical joints that includes a first spherical joint, a second spherical joint, a third spherical joint, and a fourth spherical joint, wherein the first spherical joint is attached to the first end of the first link, the second spherical joint is attached to the second end of the first link, the third spherical joint is attached to the first end of the second link, and the fourth spherical joint is attached to the second end of the second link;
wherein the first and fourth spherical joints of the first pantomesh element are the third and second spherical joints, respectively, of the second pantomesh element of a first row of the first plurality of pantomesh elements, and the third and second spherical joints of the first pantomesh element are the first and fourth spherical joints, respectively, of the $N^{th}$ pantomesh element of the first row; and
wherein an angle between the first pantomesh link and the second pantomesh link, as measured between a first plane defined by the revolute joint axis and the first spherical joint, and a second plane defined by the revolute joint axis and the third spherical joint, changes as the distance between the first spherical joint and third spherical joint changes, and wherein a first line between the first and second ends of the first link is skew to a second line between the first and second ends of the second link.

14. The apparatus of claim 13,
wherein the first and fourth spherical joints of the second pantomesh element are successively connected through one or more other pantomesh elements of the first row until the first and third spherical joints of an N-1$^{st}$ pantomesh element of the first row are the fourth and second spherical joints, respectively, of the $N^{th}$ pantomesh element of the first row, forming a closed helically connected pantomesh row.

15. The apparatus of claim 13, wherein a plurality of pantomesh element rows, including the first row, a second row and an $M^{th}$ row, where M is an integer larger than 2, are further connected such that:
the first and third spherical joints of the first pantomesh element of the first row are the fourth and second spherical joints, respectively, of the first pantomesh element of the second row,
the first and third spherical joints of the second pantomesh element of the first row are the fourth and second spherical joints, respectively, of the second pantomesh element of the second row, and
the first and third spherical joints of the $N^{th}$ pantomesh element of the first row are the fourth and second spherical joints, respectively, of the $N^{th}$ pantomesh element of the second row,
the fourth and second spherical joints of the first pantomesh element of the first row are the first and third spherical joints, respectively, of the first pantomesh element of the $M^{th}$ row,
the fourth and second spherical joints of the second pantomesh element of the first row are the first and third spherical joints, respectively, of the second pantomesh element of the $M^{th}$ row, and
the fourth and second spherical joints of the $N^{th}$ pantomesh element of the first row are the first and third spherical joints, respectively, of the $N^{th}$ pantomesh element of the $M^{th}$ row.

16. The apparatus of claim 15, wherein the plurality of pantomesh rows are further connected such that:
the first and third spherical joints of the second pantomesh element of the first row are the fourth and second spherical joints, respectively, of the $N^{th}$ pantomesh element of the first row,
the first and third spherical joints of the second pantomesh element of the second row are the fourth and second spherical joints, respectively, of the $N^{th}$ pantomesh element of the second row, and
the first and third spherical joints of the second pantomesh element of the $M^{th}$ row are the fourth and second spherical joints, respectively, of the $N^{th}$ pantomesh element of the $M^{th}$ row.

17. The apparatus of claim 13, wherein
the first and fourth spherical joints of the second pantomesh element are successively connected through one or more other pantomesh elements of the first row until
the first and fourth spherical joints of an N-1$^{st}$ pantomesh element of the first row are the third and second spherical joints, respectively, of the $N^{th}$ pantomesh element of the first row, forming a closed pantomesh row,
wherein the closed pantomesh row of the pantomesh is configured to be moved to constrain and steady biological tissue to facilitate the in vivo MRI procedure; and
wherein the apparatus further comprises:
an MRI machine, wherein MRI machine includes control logic to obtain, store and display MRI images, and wherein the control logic to obtain, store and display MRI images is interfaced to the computer configured to calculate positions and orientations of the plurality of links;
a plurality of MRI-compatible remotely controlled actuators each coupled to one of the plurality of links and configured to move its link to constrain and steady the biological tissue;
a computer configured to receive signals from one or more coils of an MRI machine and to calculate an image representation of the biological tissue;

a computer configured to calculate positions and orientations of the plurality of links during the MRI and to display indicia of the calculated positions and orientations of the plurality of links on a displayed MRI image of the biological tissue based on the image representation during a medical procedure performed in the one or more coils of the MRI machine; and a remotely actuated medical-procedure probe, wherein the computer configured to calculate positions and orientations of the plurality of links is further configured to avoid interference of the probe with the plurality of links.

18. An apparatus for stabilizing tissue during an in vivo magnetic-resonance-imaging (MRI) procedure, the apparatus comprising:

a pantomesh that includes a plurality of pairs of links, wherein each link has a first end and a second end, wherein each pair of links includes a first link and a second link, wherein the plurality of pairs of links includes a first pair of links and a second pair of links;

a first revolute joint that joins the first link of the first pair of links at a location between the first end and the second end of the first link of the first pair of links to a location between the first end and the second end of the second link of the first pair of links;

a second revolute joint that joins the first link of the second pair of links at a location between the first end and the second end of the first link of the second pair of links to the second link at a location between the first end and the second end of the second link of the second pair of links;

a first spherical joint that connects the first end of the first link of the first pair of links to the first end of the second link of the second pair of links;

a second spherical joint that is connected to the second end of the first link of the first pair of links;

a third spherical joint that connects the second end of the second link of the first pair of links to the second end of the first link of the second pair of links; and a fourth spherical joint that is connected to the first end of the second link of the first pair of links, wherein a first line that extends through the first spherical joint and the fourth spherical joint of the first pantomesh element forms a first variable angle with a second line that extends through the second spherical joint and the third spherical joint of the first pantomesh element, and wherein the first variable angle changes as a distance between the first and third spherical joints increases, and wherein the first pantomesh element is configured such that:

a first ratio of the first pantomesh element is different than a second ratio of the first pantomesh element, wherein the first ratio is of a first distance to a second distance of the first pantomesh element, wherein the second ratio is of a third distance to a fourth distance of the first pantomesh element, wherein the first distance of the first pantomesh element is between the revolute joint and the first spherical joint of the first pantomesh element, wherein the second distance of the first pantomesh element is between the second spherical joint and the first spherical joint of the first pantomesh element, wherein the third distance of the first pantomesh element is between the revolute joint and the third spherical joint of the first pantomesh element, and wherein the fourth di stance of the first pantomesh element is between the fourth spherical joint and the third spherical joint of the first pantomesh element, and if a third line that extends through the first spherical joint and the third spherical joint of the first pantomesh element is parallel to a fourth line that extends through the second spherical joint and the fourth spherical joint of the first pantomesh element, then a distance between the first spherical joint and the fourth spherical joint of the first pantomesh element is different than a distance between the second spherical joint and the third spherical joint of the first pantomesh element.

19. The apparatus of claim 18, further comprising:

a third pair of links having a first link and a second link;

a fourth pair of links having a first link and a second link;

a third revolute joint that joins the first link of the third pair of links at a location between a first end and a second end of the first link of the third pair of links to the second link of the third pair of links at a location between a first end and a second end of the second link of the third pair of links;

a fourth revolute joint that joins the first link of the fourth pair of links at a location between a first end and a second end of the first link of the fourth pair of links to the second link of the fourth pair of links at a location between a first end and a second end of the second link of the fourth pair of links, wherein the third spherical joint connects the first end of the first link of the third pair of links to the first end of the first link of the fourth pair of links;

wherein the second spherical joint connects the second end of the first link of the first pair of links to the first end of the second link of the third pair of links;

a fifth spherical joint that connects the first end of the first link of the fourth pair of links to the second end of the second link of the second pair of links; and a sixth spherical joint that connects the second end of the second link of the third pair of spherical joints to the second end of the first link of the fourth pair of links, wherein the second pantomesh element is configured such that a first ratio of the second pantomesh element is different than a second ratio of the second pantomesh element, wherein the first ratio is of a first distance to a second distance of the second pantomesh element, wherein the second ratio is of a third distance to a fourth distance of the second pantomesh element, wherein the first distance of the second pantomesh element is between the revolute joint and the first spherical joint of the second pantomesh element, wherein the second distance of the second pantomesh element is between the second spherical joint and the first spherical joint of the second pantomesh element, wherein the third distance of the second pantomesh element is between the revolute joint and the third spherical joint of the second pantomesh element, and wherein the fourth distance of the second pantomesh element is between the fourth spherical joint and the third spherical joint of the second pantomesh element.

20. The apparatus of claim 18, further comprising:

a third pair of links having a first link and a second link;

a fourth pair of links having a first link and a second link;

a third revolute joint that joins the first link of the third pair of links at a location between a first end and a second end of the first link of the third pair of links to the second link of the third pair of links at a location between a first end and a second end of the second link of the third pair of links;

a fourth revolute joint that joins the first link of the fourth pair of links at a location between a first end and a second end of the first link of the fourth pair of links to the second link of the fourth pair of links at a location between a first end and a second end of the second link of the fourth pair of links, wherein the third spherical joint connects the first end of the first link of the third pair of links to the first end of the first link of the fourth pair of links;

wherein the second spherical joint connects the second end of the first link of the first pair of links to the first end of the second link of the third pair of links;

a fifth spherical joint that connects the first end of the first link of the fourth pair of links to the second end of the second link of the second pair of links;

a sixth spherical joint that connects the second end of the second link of the third pair of spherical joints to the second end of the first link of the fourth pair of links;

a fifth pair of links having a first link and a second link;

a sixth pair of links having a first link and a second link;

a fifth revolute joint that connects a location between the first end and the second end of the first link of the fifth pair of links to a location between the first end and the second end of the second link of the fifth pair of links;

a sixth revolute joint that connects a location between the first end and the second end of the first link of the sixth pair of links to a location between the first end and the second end of the second link of the sixth pair of links;

a sixth spherical joint that connects the first end of the first link of the second pair of links to the first end of the second link of the fifth pair of links;

wherein the fifth spherical joint connects the second end of the second link of the second pair of links to the second end of the first link of the fifth pair of links;

a seventh spherical joint that connects the second end of the second link of the fifth pair of links to the first end of the first link of the sixth pair of links; and an eighth spherical joint that connects the second end of the first link of the sixth pair of links to the second end of the second link of the fourth pair of links.

* * * * *